(12) United States Patent
Knust et al.

(10) Patent No.: US 9,346,786 B2
(45) Date of Patent: *May 24, 2016

(54) PYRROLIDINE COMPOUNDS

(71) Applicant: Hoffmann-La Roche Inc., Nutley, NJ (US)

(72) Inventors: Henner Knust, Rheinfelden (DE); Andreas Koblet, Bottmingen (CH); Matthias Nettekoven, Grenzach-Wyhlen (DE); Hasane Ratni, Habsheim (FR); Claus Riemer, Freiburg (DE); Walter Vifian, Gelterkinden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/798,583

(22) Filed: Mar. 13, 2013

(65) Prior Publication Data

US 2013/0203728 A1 Aug. 8, 2013

Related U.S. Application Data

(63) Continuation of application No. 12/964,769, filed on Dec. 10, 2010, now abandoned.

(30) Foreign Application Priority Data

Dec. 18, 2009 (EP) ..................... 09179797

(51) Int. Cl.
| | | |
|---|---|---|
| *C07D 401/14* | (2006.01) | |
| *C07D 405/14* | (2006.01) | |
| *C07D 207/14* | (2006.01) | |
| *C07D 401/06* | (2006.01) | |

(52) U.S. Cl.
CPC ............ *C07D 401/14* (2013.01); *C07D 207/14* (2013.01); *C07D 401/06* (2013.01); *C07D 405/14* (2013.01)

(58) Field of Classification Search
CPC ............................. C07D 401/14; C07D 405/14
USPC ............... 514/326, 210.02, 252.03, 316, 318; 546/208, 187, 194; 544/238, 332, 405
See application file for complete search history.

(56) References Cited

U.S. PATENT DOCUMENTS

| | | | |
|---|---|---|---|
| 8,022,099 B2 * | 9/2011 | Bissantz et al. | 514/426 |
| 8,404,679 B2 * | 3/2013 | Bissantz et al. | 514/227.8 |
| 8,592,454 B2 * | 11/2013 | Shirai et al. | 514/317 |
| 8,618,303 B2 * | 12/2013 | Knust et al. | 546/208 |
| 2004/0180890 A1 | 9/2004 | Emonds-Alt et al. | |
| 2009/0312327 A1 | 12/2009 | Bissantz et al. | |
| 2011/0144081 A1 * | 6/2011 | Knust et al. | 514/210.02 |
| 2013/0184249 A1 * | 7/2013 | Knust et al. | 514/210.02 |

FOREIGN PATENT DOCUMENTS

| | | |
|---|---|---|
| WO | 2004/056805 | 7/2004 |
| WO | 2005/000247 | 1/2005 |
| WO | 2008/128891 | 10/2008 |
| WO | 2009/024502 | 2/2009 |
| WO | 2009/150110 | 12/2009 |
| WO | 2010/060703 | 6/2010 |
| WO | 2011/085886 | 7/2011 |

OTHER PUBLICATIONS

Zhang et al. "Drug metabolism in drug design and development" p. 1, 23, 24 (2007).*
Gupta "Topics in Heterocyclic Chemistry" p. 2, 182 (2006).*
Zhang et al. "Drug metabolism in drug design and development" p. 1,23, 24 (2007).*
Pyrimidine, Wikipedia p. 1-3 (2014).*
Patani et al. "Bioisosterism: a rational . . . " Chem. Rev. v. 96 p. 3147-3176 (1996).*
March et al. "March's Advanced Organic Chemistry" p. 142-144 (2007).*
Marco et al., "Neuropeptides" 32:481-488 (1998).
Jung et al., "Neuroscience" 74:403-414 ( 1996).
Tooney et al., "Neuroscience Letters" 283:185-188 ( 2000).
Giardina et al., "Exp. Opin. Ther. Patents" 10:939-960 ( 2000).
Kamali, F., "Current Opinion in Investigational Drugs" 2(7):950-956 ( 2001).
(International Search Report PCT/EP2010/069564 Feb. 9, 2011).
The Japanese Office Action, issued on Oct. 22, 2013, in the related Japanese application No. 2012-543671.
The Korean Office Action, issued on Oct. 24, 2013, in the related Korean application No. 2012-7018657.

* cited by examiner

*Primary Examiner* — Celia Chang

(57) ABSTRACT

The present application relates to compounds of formula

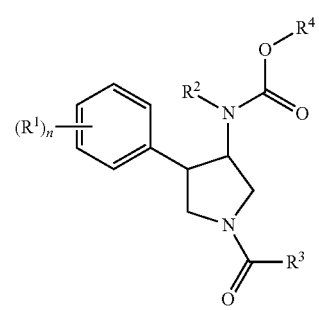

wherein $R^1$, $R^2$, $R^3$, $R^4$, and n are defined herein or to a pharmaceutically active salt thereof. The present compounds are high potential NK-3 receptor antagonists for the treatment of depression, pain, psychosis, Parkinson's disease, schizophrenia, anxiety and attention deficit hyperactivity disorder (ADHD).

15 Claims, No Drawings

PYRROLIDINE COMPOUNDS

PRIORITY TO RELATED APPLICATION(S)

This application is a continuation of application Ser. No. 12/964,769, filed Dec. 10, 2010, now pending, which claims the benefit of European Patent Application No. 09179797.7, filed Dec. 18, 2009, which is hereby incorporated by reference in its entirety.

BACKGROUND OF THE INVENTION

The three main mammalian tachykinins, substance P(SP), neurokinin A (NKA) and neurokinin B (NKB) belong to the family of neuropeptides sharing the common COOH-terminal pentapeptide sequence of Phe-X-Gly-Leu-Met-$NH_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001, 2(7), 950-956 and *Psychiatric Disorders Study* 4, *Schizophrenia,* June 2003, Decision Recources, Inc., Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs,* 2001, 2(7), 950-956 956 and *Psychiatric Disorders Study* 4, *Schizophrenia,* June 2003, Decision Recources, Inc., Waltham, Mass.).

SUMMARY OF THE INVENTION

The present application provides compounds of formula

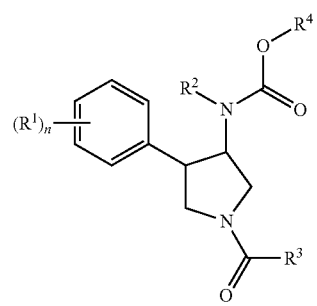

wherein
$R^1$ is hydrogen, halogen, cyano, lower alkyl or lower alkyl substituted by halogen;
n is 1, 2 or 3, wherein when n is 2 or 3, each $R^1$ is the same or different;
$R^2$ is $C_{2-7}$-alkyl or $C_{3-6}$-cycloalkyl;
$R^3$ is the group

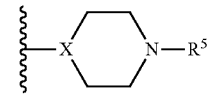

wherein
X is CH or N;
$R^5$ is hydrogen, —C(O)-lower alkyl, —C(O)O-lower alkyl, $S(O)_2$-lower alkyl, —C(O)$CH_2$O-lower alkyl, —C(O)—$CH_2$—CN, or is
—C(O)-cycloalkyl, cycloalkyl, or —$CH_2$-cycloalkyl, wherein the cycloalkyl groups are optionally substituted by lower alkyl, —$CH_2$—O-lower alkyl, lower alkoxy, $CF_3$, halogen or cyano, or is
—C(O)-heterocycloalkyl, heterocycloalkyl, —C(O)-heteroaryl, heteroaryl, —C(O)-aryl or aryl, which heterocycloalkyl, heteroaryl or aryl groups are optionally substituted by halogen, lower alkyl, =O, lower alkoxy, lower alkyl substituted by halogen, lower alkyl substituted by hydroxy, —C(O)—CH$_2$—N(di-lower alkyl), C(O)NH-lower alkyl, C(O)NH$_2$, —O—C(O)-lower alkyl, C(O)-lower alkyl, S(O)$_2$-lower alkyl or cyano;

R$^4$ is aryl, which is optionally substituted by halogen, hydroxy, lower alkyl, lower alkyl substituted by halogen, S(O)$_2$-lower alkyl, cyano or lower alkoxy;

or to a pharmaceutically active salt thereof.

The invention includes all stereoisomeric forms, including individual diastereoisomers and enantiomers of the compound of formula (I) as well as racemic and non-racemic mixtures thereof.

The present invention provides novel compounds of formula I, their manufacture, pharmaceutical compositions containing them and methods for producing such compositions.

The present compounds are high potential NK-3 receptor antagonists for the treatment of depression, pain, bipolar disorders, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

DETAILED DESCRIPTION OF THE INVENTION

The following definitions of the general terms used in the present description apply irrespective of whether the terms in question appear alone or in combination.

As used herein, the terms "lower alkyl" and "C$_{2-7}$-alkyl" denote a straight- or branched-chain hydrocarbon group containing from 2-7 carbon atoms, for example, ethyl, propyl, isopropyl, n-butyl, i-butyl, t-butyl and the like. Preferred lower alkyl groups are groups with 2-4 carbon atoms.

As used herein, the term "lower alkoxy" denotes a lower alkyl group as defined above which is connected with an oxygen atom.

The term "lower alkyl substituted by halogen" denotes a lower alkyl group as defined above, wherein at least one hydrogen atom is replaced by halogen, for example —CF$_3$, —CHF$_2$, —CH$_2$F, —CH$_2$CF$_3$, —C(CH$_3$)$_2$CF$_3$, —CH(CH$_3$)CH$_2$CF$_3$, —CH(CH$_3$)CF$_3$, —CH$_2$CH$_2$CF$_3$, —CH$_2$CH$_2$CH$_2$CF$_3$, —CH$_2$CH$_2$CF$_2$CF$_3$, —CH$_2$CH$_2$CH$_2$CF$_2$CF$_3$, —CH$_2$CF$_2$CF$_3$ and the like. Preferred lower alkyl substituted by halogen groups are groups having 1-5 carbon atoms.

The term "halogen" denotes chlorine, iodine, fluorine and bromine.

The term "lower alkyl substituted by hydroxy" denotes a lower alkyl group as defined above, wherein at least one hydrogen atom is replaced by a hydroxyl group.

The term "cycloalkyl" denotes a saturated carbon ring containing from 3-6 carbon atoms, for example, cyclopropyl, cyclobutyl, cyclopentyl, cyclohexyl, cycloheptyl, and the like.

The term "aryl" denotes a cyclic aromatic hydrocarbon radical consisting of one or more fused rings containing 6-14 carbon atoms in which at least one ring is aromatic in nature, for example phenyl, naphthyl, 1,2,3,4-tetrahydronaphthalenyl or indanyl. Preferred is the phenyl group.

The term "heteroaryl" denotes a cyclic aromatic radical consisting of one or more fused rings containing 5-14 ring atoms, preferably containing 5-10 ring atoms, in which at least one ring is aromatic in nature, and which contains at least one heteroatom, selected from N, O and S, for example quinoxalinyl, dihydroisoquinolinyl, pyrazinyl, pyrazolyl, 2,4-dihydro-pyrazol-3-one, pyridinyl, isoxazolyl, benzo[1,3]dioxol, [1.3.4]thiadiazol, pyridazinyl, pyrimidinyl, benzotriazol-5-yl, benzoimidazol-5-yl, [1,3,4]-oxadiazol-2-yl, [1,2,4]triazol-1-yl, [1,6]naphthyridin-2-yl, imidazo[4,5-b]pyridine-6-yl, tetrazolyl, thiazolyl, thiadiazolyl, thienyl, furyl, imidazol-1-yl, or benzofuranyl. Preferred heteroaryl group is pyridine-2, 3 or 4-yl.

The term "heterocycloalkyl" denotes a cyclic nonaromatic ring, containing one or two heteroatoms selected from N, S and O, for example the following groups: tetrahydropyranyl, 1,1-dioxo-hexahydro-1$\lambda^6$-thiopyranyl, 1,1-dioxo-tetrahydro-1$\lambda^6$-thiophenyl, oxetanyl, morpholinyl, [1,4]diazepam-1-yl, piperazinyl, pyrrolidinyl, piperidinyl, tetrahydrofuranyl, tetrahydrothiophenyl, piperidin-4-yl or 1,1-dioxo-$\lambda^6$-thiomorpholinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

One embodiment of the invention provides compounds of formula Ia

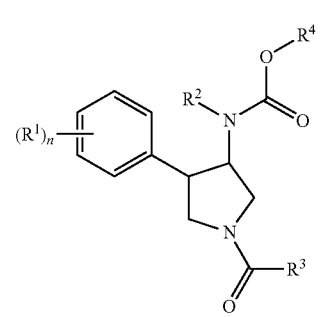

Ia wherein
R$^1$ is halogen;
n is 1, 2 or 3, wherein when n is 2 or 3, each halogen is the same or different;
R$^2$ is C$_{2-7}$-alkyl or C$_{3-6}$-cycloalkyl;
R$^3$ is the group

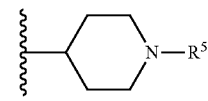

wherein
R$^5$ is hydrogen, —C(O)-lower alkyl, —C(O)O-lower alkyl, S(O)$_2$-lower alkyl, —C(O)—CH$_2$—CN, or is —C(O)-cycloalkyl,
wherein the cycloalkyl groups are optionally substituted by lower alkyl, —CH$_2$—O-lower alkyl, lower alkoxy, CF$_3$, halogen or cyano, or is —C(O)-heterocycloalkyl, —C(O)-heteroaryl, heteroaryl, —C(O)-aryl, which heterocycloalkyl, heteroaryl or aryl groups are optionally substituted by halogen, lower alkyl, =O, lower alkyl substituted by halogen, lower alkyl substituted by hydroxy, —C(O)—CH$_2$—N(di-lower alkyl), C(O)NH$_2$, —O—C(O)-lower alkyl, C(O)-lower alkyl, S(O)$_2$-lower alkyl or cyano;

R$^4$ is aryl, which is optionally substituted by halogen, or a pharmaceutically active salt thereof.

A preferred aryl group is phenyl.

The following compounds are encompassed by the present invention:

rac-{(3S,4R)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester;

rac-{(3S,4R)-4-(3,4-Dichloro-phenyl)-1-[1-(1-methyl-cyclopropanecarbonyl)-piperidine-4-carbonyl]-pyrrolidin-3-yl}-isopropyl-carbamic acid 4-fluoro-phenyl ester;

rac-{(3S,4R)-4-(3,4-Dichloro-phenyl)-1-[1-(1-methyl-cyclopropanecarbonyl)-piperidine-4-carbonyl]-pyrrolidin-3-yl}-isobutyl-carbamic acid 4-fluoro-phenyl ester;

rac-{(3S,4R)-4-(3,4-Dichloro-phenyl)-1-[1-(1-methyl-cyclopropanecarbonyl)-piperidine-4-carbonyl]-pyrrolidin-3-yl}-cyclopropyl-carbamic acid 4-fluoro-phenyl ester;

{(3S,4R)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester;

{(3R,4S)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester;

{(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester;

[(3R,4S)-1-(5'-Acetyl-3,4,5,6-tetrahydro-2H-[1,2']bipyridinyl-4-carbonyl)-4-(4-chloro-phenyl)-pyrrolidin-3-yl]-ethyl-carbamic acid 4-fluoro-phenyl ester;

[(3R,4S)-4-(4-Chloro-phenyl)-1-(4'-cyano-3,4,5,6-tetrahydro-2H-[1,2']bipyridinyl-4-carbonyl)-pyrrolidin-3-yl]-ethyl-carbamic acid 4-fluoro-phenyl ester;

[(3R,4S)-4-(4-Chloro-phenyl)-1-(5'-methanesulfonyl-3,4,5,6-tetrahydro-2H-[1,2']bipyridinyl-4-carbonyl)-pyrrolidin-3-yl]-ethyl-carbamic acid 4-fluoro-phenyl ester;

{(3R,4S)-4-(4-Chloro-phenyl)-1-[1-(5-cyano-pyrazin-2-yl)-piperidine-4-carbonyl]-pyrrolidin-3-yl}-ethyl-carbamic acid 4-fluoro-phenyl ester;

{(3R,4S)-4-(4-Chloro-phenyl)-1-[1-(6-cyano-pyridazin-3-yl)-piperidine-4-carbonyl]-pyrrolidin-3-yl}-ethyl-carbamic acid 4-fluoro-phenyl ester;

{(3S,4R)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester;

[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-ethyl-carbamic acid 4-fluoro-phenyl ester;

[(3S,4R)-4-(4-Chloro-phenyl)-1-(4'-cyano-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-ethyl-carbamic acid 4-fluoro-phenyl ester;

{(3S,4R)-4-(4-Chloro-phenyl)-1-[1-(5-cyano-pyrazin-2-yl)-piperidine-4-carbonyl]-pyrrolidin-3-yl}-ethyl-carbamic acid 4-fluoro-phenyl ester;

{(3S,4R)-4-(4-Chloro-phenyl)-1-[1-(6-cyano-pyridazin-3-yl)-piperidine-4-carbonyl]-pyrrolidin-3-yl}-ethyl-carbamic acid 4-fluoro-phenyl ester;

[(3R,4S)-4-(4-Chloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-ethyl-carbamic acid 4-fluoro-phenyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl] ethyl-carbamic acid 4-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-isopropyl-carbamic acid 4-fluoro-phenyl ester;

[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-isopropyl-carbamic acid 4-fluoro-phenyl ester;

[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-isopropyl-carbamic acid 4-fluoro-phenyl ester;

{(3S,4R)-4-(4-Chloro-phenyl)-1-[1-(6-cyano-pyridazin-3-yl)-piperidine-4-carbonyl]-pyrrolidin-3-yl}-isopropyl-carbamic acid 4-fluoro-phenyl ester;

{(3S,4R)-4-(4-Chloro-phenyl)-1-[1-(5-cyano-pyrazin-2-yl)-piperidine-4-carbonyl]-pyrrolidin-3-yl}-isopropyl-carbamic acid 4-fluoro-phenyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-isopropyl-carbamic acid 4-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-cyclopropyl-carbamic acid 4-fluoro-phenyl ester;

[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-cyclopropyl-carbamic acid 4-fluoro-phenyl ester;

[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-cyclopropyl-carbamic acid 4-fluoro-phenyl ester;

{(3S,4R)-4-(4-Chloro-phenyl)-1-[1-(6-cyano-pyridazin-3-yl)-piperidine-4-carbonyl]-pyrrolidin-3-yl}-cyclopropyl-carbamic acid 4-fluoro-phenyl ester;

{(3S,4R)-4-(4-Chloro-phenyl)-1-[1-(5-cyano-pyrazin-2-yl)-piperidine-4-carbonyl]-pyrrolidin-3-yl}-cyclopropyl-carbamic acid 4-fluoro-phenyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-cyclopropyl-carbamic acid 4-fluoro-phenyl ester;

[(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester;

[(3S,4R)-1-(5'-Chloro-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester;

Ethyl-[(3S,4R)-4-(4-fluoro-phenyl)-1-(5'-methanesulfonyl-3,4,5,6-tetrahydro-2H-[1,2]bipyridinyl-4-carbonyl)-pyrrolidin-3-yl]-carbamic acid 4-fluoro-phenyl ester;

[(3S,4R)-1-(5'-Acetyl-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester;

4-{(3R,4S)-3-(4-Chloro-3-fluoro-phenyl)-4-[ethyl-(4-fluoro-phenoxycarbonyl)-amino]-pyrrolidine-1-carbonyl}-piperidine-1-carboxylic acid tert-butyl ester;

[(3S,4R)-4-(4-Chloro-3-fluoro-phenyl)-1-(5'-cyano-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-3-fluoro-phenyl)-1-(5'-chloro-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-3-fluoro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-3-fluoro-phenyl)-1-(6'-cyano-3,4,5,6-tetrahydro-2H-[1,3']bipyridinyl-4-carbonyl)-pyrrolidin-3-yl]-ethyl-carbamic acid 4-fluoro-phenyl ester;

{(3S,4R)-4-(4-Chloro-3-fluoro-phenyl)-1-[1-(1-methyl-cyclopropanecarbonyl)-piperidine-4-carbonyl]-pyrrolidin-3-yl}-ethyl-carbamic acid 4-fluoro-phenyl ester;

[(3S,4R)-4-(4-Chloro-3-fluoro-phenyl)-1-(4'-cyano-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-3-fluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-3-fluoro-phenyl)-1-(5'-methyl-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-1-(5'-Cyano-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester;

[(3S,4R)-1-(5'-Chloro-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester;

[(3S,4R)-4-(3,4-Difluoro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-1-(6'-Cyano-3,4,5,6-tetrahydro-2H[1,3']bipyridinyl-4-carbonyl)-4-(3,4-difluoro-phenyl)-pyrrolidin-3-yl]-ethyl-carbamic acid 4-fluoro-phenyl ester;

{(3S,4R)-4-(3,4-Difluoro-phenyl)-1-[1-(1-methyl-cyclopropanecarbonyl)-piperidine-4-carbonyl]-pyrrolidin-3-yl}-ethyl-carbamic acid 4-fluoro-phenyl ester;

[(3S,4R)-1-(4'-Cyano-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester;

[(3S,4R)-4-(3,4-Difluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(3,4-Difluoro-phenyl)-1-(5'-methyl-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-3-fluoro-phenyl)-1-(piperidine-4-carbonyl)-pyrrolidin-3-yl]-ethyl-carbamic acid 4-fluoro-phenyl ester;

{(3S,4R)-4-(4-Chloro-3-fluoro-phenyl)-1-[1-(6-cyano-pyridazin-3-yl)-piperidine-4-carbonyl]-pyrrolidin-3-yl}-ethyl-carbamic acid 4-fluoro-phenyl ester;

[(3S,4R)-1-[1-(6-Cyano-pyridazin-3-yl)-piperidine-4-carbonyl]-4-(3,4-difluoro-phenyl)-pyrrolidin-3-yl]-ethyl-carbamic acid 4-fluoro-phenyl ester;

[(3S,4R)-1-(5'-Acetyl-3,4,5,6-tetrahydro-2H-[1,2']bipyridinyl-4-carbonyl)-4-(4-chloro-3-fluoro-phenyl)-pyrrolidin-3-yl]-ethyl-carbamic acid 4-fluoro-phenyl ester;

[(3S,4R)-1-(5'-Acetyl-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester;

{(3S,4R)-4-(4-Chloro-3-fluoro-phenyl)-1-[1-(5-cyano-pyrazin-2-yl)-piperidine-4-carbonyl]-pyrrolidin-3-yl}-ethyl-carbamic acid 4-fluoro-phenyl ester;

[(3S,4R)-1-[1-(5-Cyano-pyrazin-2-yl)-piperidine-4-carbonyl]-4-(3,4-difluoro-phenyl)-pyrrolidin-3-yl]-ethyl-carbamic acid 4-fluoro-phenyl ester;

[(3S,4R)-4-(4-Chloro-3-fluoro-phenyl)-1-(5'-methanesulfonyl-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(3,4-Difluoro-phenyl)-1-(5'-methanesulfonyl-3,4,5,6-tetrahydro-2H-[1,2']bipyridinyl-4-carbonyl)-pyrrolidin-3-yl]-ethyl-carbamic acid 4-fluoro-phenyl ester;

{(3S,4R)-4-(4-Chloro-3-fluoro-phenyl)-1-[1-(3-methyl-oxetane-3-carbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(3,3-difluoro-cyclobutanecarbonyl)-piperidine-4-carbonyl]-pyrrolidin-3-yl}-ethyl-carbamic acid 4-fluoro-phenyl ester;

[(3S,4R)-4-(4-Chloro-3-fluoro-phenyl)-1-(1-cyclobutanecarbonyl-piperidine-4-carbonyl)-pyrrolidin-3-yl]-ethyl-carbamic acid 4-fluoro-phenyl ester;

{(3S,4R)-4-(4-Chloro-3-fluoro-phenyl)-1-[1-(1-trifluoromethyl-cyclobutanecarbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(3-fluoro-cyclobutanecarbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(2,2-difluoro-cyclopropanecarbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(1-trifluoromethyl-cyclopropanecarbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(1-cyano-cyclopropanecarbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(2,2-dimethyl-tetrahydro-pyran-4-carbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(5-trifluoromethyl-pyridine-2-carbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(5-fluoro-pyridine-2-carbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(4-cyano-benzoyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(4-fluoro-benzoyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(5-trifluoromethyl-pyrazine-2-carbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(6-cyano-pyridine-3-carbonyl)-piperidine-4-carbonyl]-pyrrolidin-3-yl}-ethyl-carbamic acid 4-fluoro-phenyl ester;

[(3S,4R)-1-(1-Acetyl-piperidine-4-carbonyl)-4-(4-chloro-3-fluoro-phenyl)-pyrrolidin-3-yl]-ethyl-carbamic acid 4-fluoro-phenyl ester;

[(3S,4R)-4-(4-Chloro-3-fluoro-phenyl)-1-(1-methanesulfonyl-piperidine-4-carbonyl)-pyrrolidin-3-yl]-ethyl-carbamic acid 4-fluoro-phenyl ester;

[(3S,4R)-1-(1-Acetyl-piperidine-4-carbonyl)-4-(4-chloro-phenyl)-pyrrolidin-3-yl]-ethyl-carbamic acid 4-fluoro-phenyl ester;

{(3S,4R)-4-(4-Chloro-3-fluoro-phenyl)-1-[5'-(1-hydroxy-1-methyl-ethyl)-3,4,5,6-tetrahydro-2H-[1,2']bipyridinyl-4-carbonyl]-pyrrolidin-3-yl}-ethyl-carbamic acid 4-fluoro-phenyl ester;

{(3S,4R)-4-(4-Chloro-phenyl)-1-[1-(3-methyl-oxetane-3-carbonyl)-piperidine-4-carbonyl]-pyrrolidin-3-yl}-ethyl-carbamic acid 2-fluoro-phenyl ester;
{(3S,4R)-4-(4-Chloro-phenyl)-1-[1-(1-cyano-cyclopropanecarbonyl)-piperidine-4-carbonyl]-pyrrolidin-3-yl}-ethyl-carbamic acid 2-fluoro-phenyl ester;
{(3S,4R)-4-(4-Chloro-phenyl)-1-[1-(5-trifluoromethyl-pyridine-2-carbonyl)-piperidine-4-carbonyl]-pyrrolidin-3-yl}-ethyl-carbamic acid 2-fluoro-phenyl ester;
[(3S,4R)-4-(4-Chloro-phenyl)-1-(1-cyclobutanecarbonyl-piperidine-4-carbonyl)-pyrrolidin-3-yl]-ethyl-carbamic acid 4-fluoro-phenyl ester;
{(3S,4R)-4-(4-Chloro-phenyl)-1-[1-(3-methyl-oxetane-3-carbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(3-fluoro-cyclobutanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(3,3-difluoro-cyclobutanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(3-methoxy-cyclobutanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(1-trifluoromethyl-cyclobutanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(2-cyano-acetyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(1-cyano-cyclopropanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(1-trifluoromethyl-cyclopropanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(2,2-difluoro-cyclopropanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(tetrahydro-pyran-4-carbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(2,2-dimethyl-tetrahydro-pyran-4-carbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(1-methoxymethyl-cyclopropanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(2,2-dimethyl-cyclopropanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(5-trifluoromethyl-pyridine-2-carbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(5-fluoro-pyridine-2-carbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(6-oxo-piperidine-3-carbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(1-isopropyl-6-oxo-piperidine-3-carbonyl)-piperidine-4-carbonyl]-pyrrolidin-3-yl}-ethyl-carbamic acid 4-fluoro-phenyl ester;
[(3S,4R)-4-(4-Chloro-3-fluoro-phenyl)-1-(1-isopropyl-6-oxo-piperidine-3-carbonyl)-pyrrolidin-3-yl]-ethyl-carbamic acid 4-fluoro-phenyl ester;
{(3S,4R)-4-(3,4-Difluoro-phenyl)-1-[1-((S)-4-oxo-azetidine-2-carbonyl)-piperidine-4-carbonyl]-pyrrolidin-3-yl}-ethyl-carbamic acid 4-fluoro-phenyl ester;
{(3S,4R)-4-(3,4-Difluoro-phenyl)-1-[1-(6-oxo-piperidine-3-carbonyl)-piperidine-4-carbonyl]-pyrrolidin-3-yl}-ethyl-carbamic acid 4-fluoro-phenyl ester;
{(3S,4R)-4-(4-Chloro-phenyl)-1-[5'-(1-hydroxy-ethyl)-3,4,5,6-tetrahydro-2H-[1,2']bipyridinyl-4-carbonyl]-pyrrolidin-3-yl}-ethyl-carbamic acid 4-fluoro-phenyl ester;
[(3S,4R)-1-(5'-Carbamoyl-3,4,5,6-tetrahydro-2H-[1,2']bipyridinyl-4-carbonyl)-4-(4-chloro-3-fluoro-phenyl)-pyrrolidin-3-yl]-ethyl-carbamic acid 4-fluoro-phenyl ester;
[(3S,4R)-4-(4-Chloro-phenyl)-1-(5'-chloro-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-1-(5'-Carbamoyl-3,4,5,6-tetrahydro-2H-[1,2']bipyridinyl-4-carbonyl)-4-(4-chloro-phenyl)-pyrrolidin-3-yl]-ethyl-carbamic acid 4-fluoro-phenyl ester;
[(3S,4R)-4-(3,4-Dichloro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-1-(5'-Chloro-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester;
[(3S,4R)-4-(3,4-Dichloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-1-(5'-Carbamoyl-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester;
[(3S,4R)-1-(5'-Acetyl-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester;
[(3S,4R)-4-(3-Chloro-4-fluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-4-(3-Chloro-4-fluoro-phenyl)-1-(5'-chloro-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-4-(3-Chloro-4-fluoro-phenyl)-(5'-trifluoromethyl-3,4,5,6-tetrahydro-2H-[1,2]bipyridinyl-4-carbonyl)-pyrrolidin-3-yl]-ethyl-carbamic acid 4-fluoro-phenyl ester;
[(3S,4R)-1-(5'-Acetyl-3,4,5,6-tetrahydro-2H-[1,2']bipyridinyl-4-carbonyl)-4-(3-chloro-4-fluoro-phenyl)-pyrrolidin-3-yl]-ethyl-carbamic acid 4-fluoro-phenyl ester;
{(3S,4R)-4-(4-Chloro-phenyl)-1-[1-((S)-4-oxo-azetidine-2-carbonyl)-piperidine-4-carbonyl]-pyrrolidin-3-yl}-ethyl-carbamic acid 4-fluoro-phenyl ester;
[(3S,4R)-1-[5'42-Diethylamino-acetyl)-3,4,5,6-tetrahydro-2H-[1,2']bipyridinyl-4-carbonyl]-4-(4-fluoro-phenyl)-pyrrolidin-3-yl]-ethyl-carbamic acid 4-fluoro-phenyl ester; and acetic acid 4-{(3R,4S)-3-(4-chloro-phenyl)-4-[ethyl-(4-fluoro-phenoxycarbonyl)-amino]-pyrrolidine-1-carbonyl}-3,4,5,6-tetrahydro-2H-[1,2']bipyridinyl-5'-yl ester.

In one embodiment the invention provides the following compounds
rac-{(3S,4R)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester;
{(3S,4R)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester;

[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-ethyl-carbamic acid 4-fluoro-phenyl ester;
[(3S,4R)-4-(4-Chloro-phenyl)-1-(4'-cyano-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-ethyl-carbamic acid 4-fluoro-phenyl ester;
{(3S,4R)-4-(4-Chloro-phenyl)-1-[1-(5-cyano-pyrazin-2-yl)-piperidine-4-carbonyl]-pyrrolidin-3-yl}-ethyl-carbamic acid 4-fluoro-phenyl ester;
{(3S,4R)-4-(4-Chloro-phenyl)-1-[1-(6-cyano-pyridazin-3-yl)-piperidine-4-carbonyl]-pyrrolidin-3-yl}-ethyl-carbamic acid 4-fluoro-phenyl ester;
[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-4-(4-Chloro-phenyl)-1-(5'-cyano-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester;
Ethyl-[(3S,4R)-4-(4-fluoro-phenyl)-1-(5'-methanesulfonyl-3,4,5,6-tetrahydro-2H-[1,2]bipyridinyl-4-carbonyl)-pyrrolidin-3-yl]-carbamic acid 4-fluoro-phenyl ester;
[(3S,4R)-1-(5'-Acetyl-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester;
4-{(3R,4S)-3-(4-Chloro-3-fluoro-phenyl)-4-[ethyl-(4-fluoro-phenoxycarbonyl)-amino]-pyrrolidine-1-carbonyl}-piperidine-1-carboxylic acid tert-butyl ester;
[(3S,4R)-4-(4-Chloro-3-fluoro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester;
{(3S,4R)-4-(4-Chloro-3-fluoro-phenyl)-1-[1-(1-methyl-cyclopropanecarbonyl)-piperidine-4-carbonyl]-pyrrolidin-3-yl}-ethyl-carbamic acid 4-fluoro-phenyl ester;
[(3S,4R)-4-(4-Chloro-3-fluoro-phenyl)-1-(4'-cyano-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-4-(4-Chloro-3-fluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-4-(4-Chloro-3-fluoro-phenyl)-1-(5'-methyl-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-1-(5'-Cyano-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester;
[(3S,4R)-1-(5'-Chloro-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester;
[(3S,4R)-4-(3,4-Difluoro-phenyl)-1-(5'-trifluoromethyl-3,4,5,6-tetrahydro-2H-[1,2']bipyridinyl-4-carbonyl)-pyrrolidin-3-yl]ethyl-carbamic acid 4-fluoro-phenyl ester;
[(3S,4R)-1-(6'-Cyano-3,4,5,6-tetrahydro-2H[1,3']bipyridinyl-4-carbonyl)-4-(3,4-difluoro-phenyl)-pyrrolidin-3-yl]-ethyl-carbamic acid 4-fluoro-phenyl ester;
[(3S,4R)-4-(3,4-Difluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-4-(3,4-Difluoro-phenyl)-1-(5'-methyl-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-1-[1-(6-Cyano-pyridazin-3-yl)-piperidine-4-carbonyl]-4-(3,4-difluoro-phenyl)-pyrrolidin-3-yl]-ethyl-carbamic acid 4-fluoro-phenyl ester;
[(3S,4R)-1-(5'-Acetyl-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester;
[(3S,4R)-1-[1-(5-Cyano-pyrazin-2-yl)-piperidine-4-carbonyl]-4-(3,4-difluoro-phenyl)-pyrrolidin-3-yl]-ethyl-carbamic acid 4-fluoro-phenyl ester;
[(3S,4R)-4-(3,4-Difluoro-phenyl)-1-(5'-methanesulfonyl-3,4,5,6-tetrahydro-2H-[1,2']bipyridinyl-4-carbonyl)-pyrrolidin-3-yl]-ethyl-carbamic acid 4-fluoro-phenyl ester;
{(3S,4R)-4-(4-Chloro-3-fluoro-phenyl)-1-[1-(3-methyl-oxetane-3-carbonyl)-piperidine-4-carbonyl]-pyrrolidin-3-yl}-ethyl-carbamic acid 4-fluoro-phenyl ester;
{(3S,4R)-4-(4-Chloro-3-fluoro-phenyl)-1-[1-(3,3-difluoro-cyclobutanecarbonyl)-piperidine-4-carbonyl]-pyrrolidin-3-yl}-ethyl-carbamic acid 4-fluoro-phenyl ester;
[(3S,4R)-4-(4-Chloro-3-fluoro-phenyl)-1-(1-cyclobutanecarbonyl-piperidine-4-carbonyl)-pyrrolidin-3-yl]-ethyl-carbamic acid 4-fluoro-phenyl ester;
{(3S,4R)-4-(4-Chloro-3-fluoro-phenyl)-1-[1-(1-trifluoromethyl-cyclobutanecarbonyl)-piperidine-4-carbonyl]-pyrrolidin-3-yl}-ethyl-carbamic acid 4-fluoro-phenyl ester;
{(3S,4R)-4-(4-Chloro-3-fluoro-phenyl)-1-[1-(3-fluoro-cyclobutanecarbonyl)-piperidine-4-carbonyl]-pyrrolidin-3-yl}-ethyl-carbamic acid 4-fluoro-phenyl ester;
{(3S,4R)-4-(4-Chloro-3-fluoro-phenyl)-1-[1-(2,2-difluoro-cyclopropanecarbonyl)-piperidine-4-carbonyl]-pyrrolidin-3-yl}-ethyl-carbamic acid 4-fluoro-phenyl ester;
{(3S,4R)-4-(4-Chloro-3-fluoro-phenyl)-1-[1-(1-trifluoromethyl-cyclopropanecarbonyl)-piperidine-4-carbonyl]-pyrrolidin-3-yl}-ethyl-carbamic acid 4-fluoro-phenyl ester;
{(3S,4R)-4-(4-Chloro-3-fluoro-phenyl)-1-[1-(1-cyano-cyclopropanecarbonyl)-piperidine-4-carbonyl]-pyrrolidin-3-yl}-ethyl-carbamic acid 4-fluoro-phenyl ester;
{(3S,4R)-4-(4-Chloro-3-fluoro-phenyl)-1-[1-(2,2-dimethyl-tetrahydro-pyran-4-carbonyl)-piperidine-4-carbonyl]-pyrrolidin-3-yl}-ethyl-carbamic acid 4-fluoro-phenyl ester;
{(3S,4R)-4-(4-Chloro-3-fluoro-phenyl)-1-[1-(5-fluoro-pyridine-2-carbonyl)-piperidine-4-carbonyl]-pyrrolidin-3-yl}-ethyl-carbamic acid 4-fluoro-phenyl ester;
{(3S,4R)-4-(4-Chloro-3-fluoro-phenyl)-1-[1-(4-fluoro-benzoyl)-piperidine-4-carbonyl]-pyrrolidin-3-yl}-ethyl-carbamic acid 4-fluoro-phenyl ester;
{(3S,4R)-4-(4-Chloro-3-fluoro-phenyl)-1-[1-(5-trifluoromethyl-pyrazine-2-carbonyl)-piperidine-4-carbonyl]-pyrrolidin-3-yl}-ethyl-carbamic acid 4-fluoro-phenyl ester;
{(3S,4R)-4-(4-Chloro-3-fluoro-phenyl)-1-[1-(6-cyano-pyridine-3-carbonyl)-piperidine-4-carbonyl]-pyrrolidin-3-yl}-ethyl-carbamic acid 4-fluoro-phenyl ester;
[(3S,4R)-1-(1-Acetyl-piperidine-4-carbonyl)-4-(4-chloro-3-fluoro-phenyl)-pyrrolidin-3-yl]-ethyl-carbamic acid 4-fluoro-phenyl ester;
[(3S,4R)-1-(1-Acetyl-piperidine-4-carbonyl)-4-(4-chloro-phenyl)-pyrrolidin-3-yl]-ethyl-carbamic acid 4-fluoro-phenyl ester;
{(3S,4R)-4-(4-Chloro-3-fluoro-phenyl)-1-[5'-(1-hydroxy-1-methyl-ethyl)-3,4,5,6-tetrahydro-2H-[1,2]bipyridinyl-4-carbonyl]-pyrrolidin-3-yl}-ethyl-carbamic acid 4-fluoro-phenyl ester;
[(3S,4R)-4-(4-Chloro-phenyl)-1-(1-cyclobutanecarbonyl-piperidine-4-carbonyl)-pyrrolidin-3-yl]-ethyl-carbamic acid 4-fluoro-phenyl ester;

{(3S,4R)-4-(4-Chloro-phenyl)-1-[1-(3-methyl-oxetane-3-carbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(3-fluoro-cyclobutanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(3,3-difluoro-cyclobutanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(3-methoxy-cyclobutanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(1-trifluoromethyl-cyclobutanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(2-cyano-acetyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(1-cyano-cyclopropanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(1-trifluoromethyl-cyclopropanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(2,2-difluoro-cyclopropanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(tetrahydro-pyran-4-carbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(2,2-dimethyl-tetrahydro-pyran-4-carbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(1-methoxymethyl-cyclopropanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(2,2-dimethyl-cyclopropanecarbonyl)-piperidine-4-carbonyl]-pyrrolidin-3-yl}-ethyl-carbamic acid 4-fluoro-phenyl ester;
{(3S,4R)-4-(4-Chloro-phenyl)-1-[1-(5-fluoro-pyridine-2-carbonyl)-piperidine-4-carbonyl]-pyrrolidin-3-yl}-ethyl-carbamic acid 4-fluoro-phenyl ester;
{(3S,4R)-4-(4-Chloro-phenyl)-1-[5'-(1-hydroxy-ethyl)-3,4,5,6-tetrahydro-2H-[1,2']bipyridinyl-4-carbonyl]-pyrrolidin-3-yl}-ethyl-carbamic acid 4-fluoro-phenyl ester;
[(3S,4R)-1-(5'-Carbamoyl-3,4,5,6-tetrahydro-2H-[1,2']bipyridinyl-4-carbonyl)-4-(4-chloro-3-fluoro-phenyl)-pyrrolidin-3-yl]-ethyl-carbamic acid 4-fluoro-phenyl ester;
[(3S,4R)-4-(4-Chloro-phenyl)-1-(5'-chloro-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-1-(5'-Carbamoyl-3,4,5,6-tetrahydro-2H-[1,2']bipyridinyl-4-carbonyl)-4-(4-chloro-phenyl)-pyrrolidin-3-yl]-ethyl-carbamic acid 4-fluoro-phenyl ester;
[(3S,4R)-4-(3,4-Dichloro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-1-(5'-Chloro-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester;
[(3S,4R)-4-(3,4-Dichloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-1-(5'-Carbamoyl-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester;
[(3S,4R)-1-(5'-Acetyl-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester;
[(3S,4R)-4-(3-Chloro-4-fluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-4-(3-Chloro-4-fluoro-phenyl)-1-(5'-chloro-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-4-(3-Chloro-4-fluoro-phenyl)-1-(5'-trifluoromethyl-3,4,5,6-tetrahydro-2H-[1,2]bipyridinyl-4-carbonyl)-pyrrolidin-3-yl]-ethyl-carbamic acid 4-fluoro-phenyl ester;
[(3S,4R)-1-(5'-Acetyl-3,4,5,6-tetrahydro-2H-[1,2']bipyridinyl-4-carbonyl)-4-(3-chloro-4-fluoro-phenyl)-pyrrolidin-3-yl]-ethyl-carbamic acid 4-fluoro-phenyl ester; and
Acetic acid 4-{(3R,4S)-3-(4-chloro-phenyl)-4-[ethyl-(4-fluoro-phenoxycarbonyl)-amino]-pyrrolidine-1-carbonyl}-3,4,5,6-tetrahydro-2H-[1,2']bipyridinyl-5'-yl ester.

An embodiment of the invention provides compounds of formula

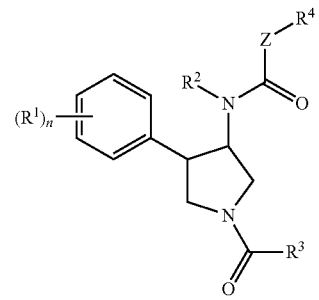

wherein
$R^1$ is hydrogen, halogen, cyano, lower alkyl or lower alkyl substituted by halogen;
n is 1, 2 or 3, wherein when n is 2 or 3, each $R^1$ is the same or different;
$R^2$ is $C_{2-7}$-alkyl or $C_{3-6}$-cycloalkyl;
$R^3$ is a non aromatic heterocyclic group

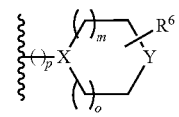

wherein
X is CH;
Y is —N($R^{7'}$)—;
$R^6$ is hydrogen;
o and m are each independently 0, 1 or 2;
p is 0 or 1;
$R^{7'}$ is hydrogen, —C(O)-lower alkyl, —C(O)O-lower alkyl, $S(O)_2$-lower alkyl, —C(O)CH$_2$O-lower alkyl, or is
cycloalkyl, —CH$_2$-cycloalkyl or —C(O)-cycloalkyl,
wherein the cycloalkyl groups are optionally substituted by lower alkyl, CF$_3$, halogen or cyano, or is
—C(O)-heterocycloalkyl, heterocycloalkyl, heteroaryl, —C(O)-heteroaryl,
—C(O)-aryl, or aryl,
which heterocycloalkyl, heteroaryl or aryl groups are optionally substituted by halogen, lower alkyl, lower alkoxy, lower alkyl substituted by halogen, C(O)NH-lower alkyl, C(O)NH$_2$, C(O)-lower alkyl, S(O)$_2$-lower alkyl or cyano;

Z is —O—;

R$^4$ is (CH$_2$)$_q$-aryl or is (CH$_2$)$_q$-heteroaryl, which aryl or heteroaryl rings are optionally substituted by halogen, hydroxy, lower alkyl, lower alkyl substituted by halogen, S(O)$_2$-lower alkyl, cyano or by lower alkoxy;

q is 0 or 1;

or to a pharmaceutically active salt thereof.

The present compounds of formula I and their pharmaceutically acceptable salts can be prepared by processes described below, which process comprises a) coupling a compound of formula II

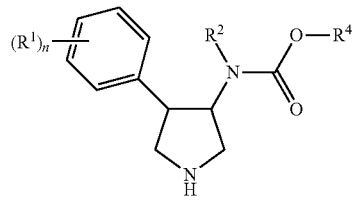

II with a suitable carbamoyl chloride, acid chloride or carboxylic acid to afford a compound of formula I

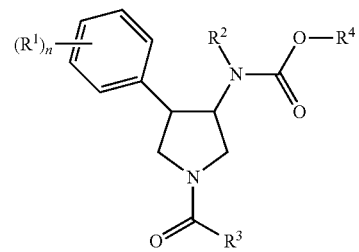

I wherein the substituents R$^1$, R$^2$, R$^3$ and R$^4$ are as defined above and if desired, converting the compounds obtained into pharmaceutically acceptable acid addition salts;

or b) coupling a compound with formula III

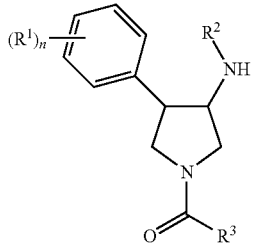

III with a corresponding chloroformate, acid anhydride or a mixture of triphosgene and corresponding alcohol or amine to afford a compound of formula I

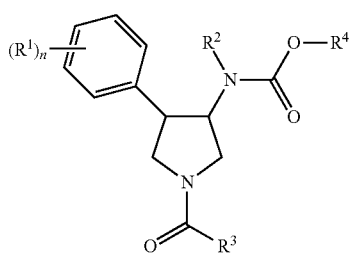

I wherein the substituents R$^1$, R$^2$, R$^3$ and R$^4$ are as defined above and if desired, converting the compounds obtained into pharmaceutically acceptable acid addition salts.

The following schemes 1 and 2 describe the processes for the preparation of compounds of formula I in more detail. The starting material of formula II is a known compound and can be prepared according to methods known in the art.

Scheme 1

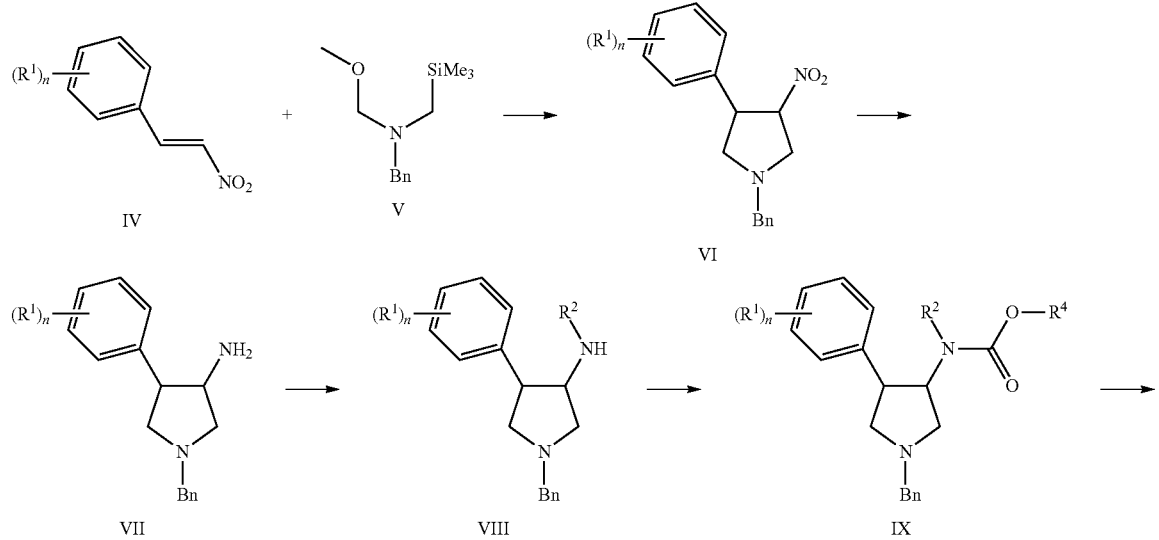

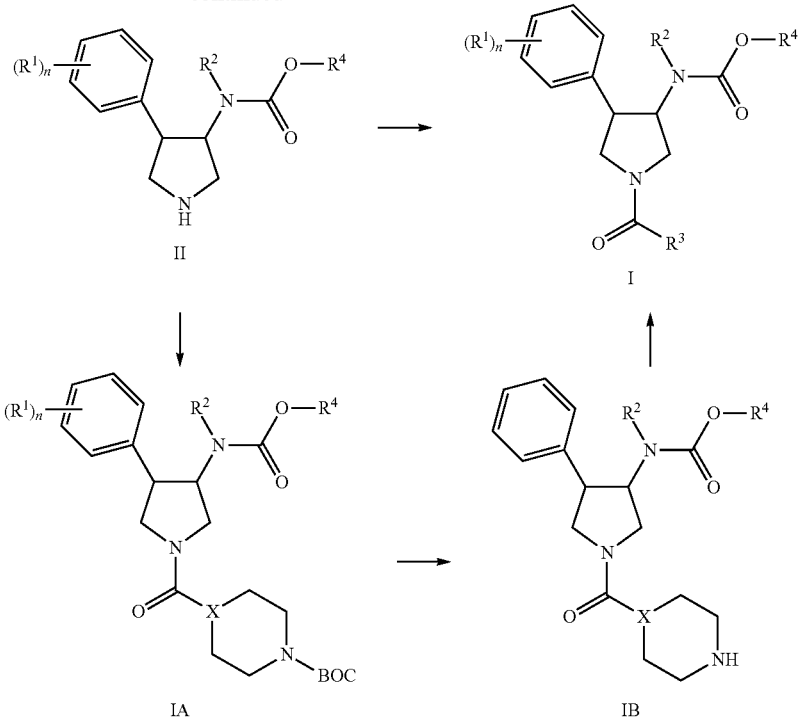

where in the substituents $R^1$, $R^2$, $R^3$ and $R^4$ and X are as defined above According to scheme 1, the 3,4-disubstituted pyrrolidine VI is prepared via a stereo specific 1,3-dipolar cycloaddition between the 2-nitrostyrene compound IV and the azomethine ylide generated in situ from the N-(methoxymethyl)-N-(phenylmethyl)-N-(trimethylsilyl)methylamine V in the presence of a catalytic amount of acid, such as TFA. Reduction of the nitro moiety of VI using standard conditions for example $SnCl_2·H_2O$ yields VII. The amino moiety of VII is subsequently alkylated to produce VIII. Reaction of VIII with an acid anhydride, chloroformate or a mixture of triphosgene and an alcohol or amine in the presence of a base affords IX. Selective N-debenzylation is then carried out using several known procedures which are compatible with the substitution patterns of the aromatic rings to afford II. Finally, compounds I are prepared via a coupling with a suitable carbamoyl chloride, acid chloride or carboxylic acide. Alternatively, pyrrolidine II is coupled with the corresponding acid to afford a compound of formula IA which can be deprotected to afford the piperidine of formula IB which might be further derivatised to obtain final compounds of formula I.

Scheme 2

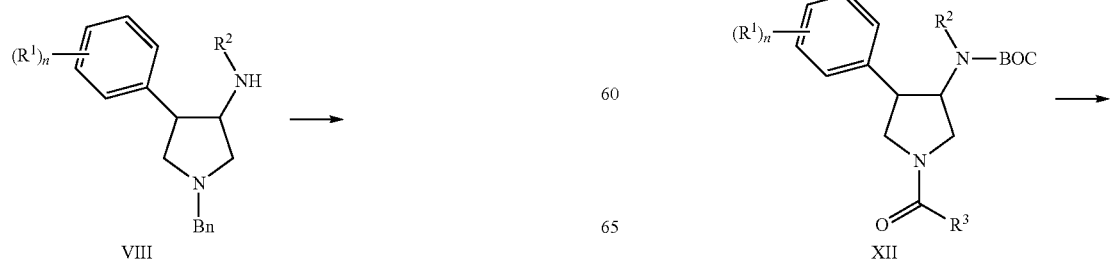

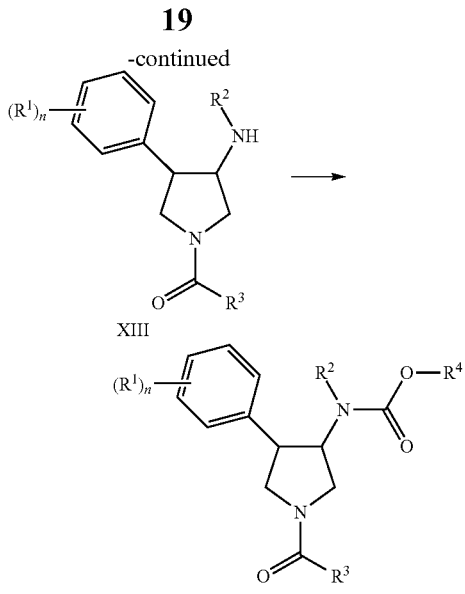

wherein the substituents $R^1$, $R^2$, $R^3$ and $R^4$ are as defined above

According to scheme 2, the secondary amine of the intermediates VII can be protected, for instance with a Boc group to afford a compound of formula X, followed by a selective debenzylation to produce XI. Then a coupling with a suitable carbamoyl chloride, acid chloride or carboxylic acid gives XII. Deprotection with TFA affords the free amine XIII, which after reaction with an acid anhydride, chloroformate or a mixture of triphosgene and an alcohol or amine in the presence of a base affords compounds of formula I.

Example 1 rac-{(3S,4R)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester

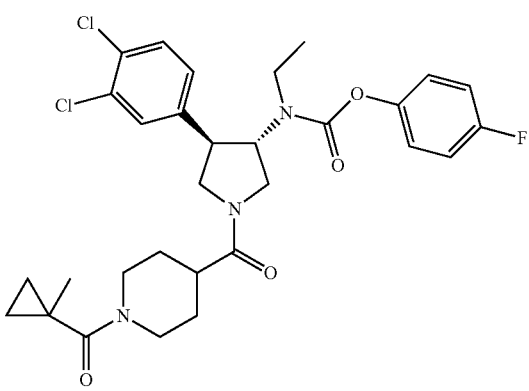 [SMILES: CCN(C(=O)Oc1ccc(F)cc1)[C@@H]1CN(C(=O)C2CCN(C(=O)C3(C)CC3)CC2)C[C@H]1c1ccc(Cl)c(Cl)c1]

a) rac-(3R,4S)-1-Benzyl-3-(3,4-dichloro-phenyl)-4-nitro-pyrrolidine

A solution of N-(methoxymethyl)-N-(phenylmethyl)-N-(trimethylsilyl)methylamine (32.50 g, 0.135 mol) in $CH_2Cl_2$ (70 mL) was added drop wise, over a 30 minutes period, to a stirred solution of 1,2-dichloro-4-((E)-2-nitro-vinyl)-benzene (19.60 g, 0.09 mol) and trifluoroacetic acid (1.54 mL, 0.013 mol) in $CH_2Cl_2$ (160 mL) at 0° C. The ice bath was removed, and the solution was stirred at 25° C. for an additional 48 h. It was then concentrated and purification by flash chromatography ($SiO_2$, EtOAc/H 1:6) afforded 25.0 g (79%) of the title compound as a yellow oil. MS m/e: 351.0 (M+H+).

b) rac-(3S,4R)-1-Benzyl-4-(3,4-dichloro-phenyl)-pyrrolidin-3-ylamine

To a stirred solution of rac-(3R,4S)-1-benzyl-3-(3,4-dichloro-phenyl)-4-nitro-pyrrolidine (11.60 g, 33.0 mmol) in EtOAc (200 mL) was added in one portion $SnCl_2.2H_2O$ (37.26 g, 0.165 mol). The reaction mixture was then heated at reflux for 4 hours, cooled down to ambient temperature and a saturated aqueous solution of $NaHCO_3$ was added. The salts were filtered off and the product extracted with EtOAc. The organic phases were then dried over $Na_2SO_4$, and concentration under vacuum gave 5.7 g (54%) of rac-(3S,4R)-1-benzyl-4-(3,4-dichloro-phenyl)-pyrrolidin-3-ylamine as a yellow oil. The product was then used in the next step without further purification. ES-MS m/e: 321.2 (M+H+).

c) rac-(3S,4R)-[1-Benzyl-4-(3,4-dichloro-phenyl)-pyrrolidin-3-yl]-carbamic acid tert-butyl ester To a solution of rac-(3S,4R)-1-benzyl-4-(3,4-dichloro-phenyl)-pyrrolidin-3-ylamine (30.64 g, 0.095 mol) in dichloromethane (300 mL) was added N,N-diisopropylamine (32.65 mL, 0.191 mol) and 4-dimethylaminopyridine (1.17 g, 0.01 mol). The reaction mixture was cooled to 0° C. and di-tert-butyl-dicarbonate (24.98 g, 0.114 mol) was added. After stirring for 2 h at 0° C. and at ambient temperature for 18 h it was concentrated. Purification by flash chromatography ($SiO_2$, EtOAc/Heptane 1:3) afforded 5.82 g (14%) of the title compound as a light yellow solid. ES-MS m/e: 421.1 (M+H+).

d) rac-(3S,4R)-[4-(3,4-Dichloro-phenyl)-pyrrolidin-3-yl]-carbamic acid tert-butyl ester To a solution of rac-(3S,4R)-[1-benzyl-4-(3,4-dichloro-phenyl)-pyrrolidin-3-yl]-carbamic acid tert-butyl ester (5.59 g, 0.013 mol) and N,N-diisopropylamine (6.81 mL, 0.017 mol) in toluene (60 mL) was added at ambient temperature 1-chloroethyl formate (1.88 mL, 0.017 mol) and the reaction mixture was stirred for 24 h. It was concentrated and the resulting residue was diluted in methanol (60 mL) and stirred for 3 h at ambient temperature. Concentration afforded the crude title compound (6.59 g, 67% purity) as a light brown solid which was directly used without further purification.

e) rac-(3S,4R)-{4-(3,4-Dichloro-phenyl)-1-[1-(1-methyl-cyclopropanecarbonyl)-piperidine-4-carbonyl]-pyrrolidin-3-yl}-carbamic acid tert-butyl ester To a solution of 1-(1-methyl-cyclopropanecarbonyl)-piperidine-4-carboxylic acid (4.48 g, 0.02 mol) in DMF (40 ml) was added O-(7-azabenzotriazol-1-yl)-N,N,N',N'-tetramethyluronium hexafluorophosphate (9.54 g, 0.03 mol). After stirring for 10 min at ambient temperature N,N-diisopropyl ethyl amine (19.82 ml, 0.116 mol) and a solution of rac-(3S,4R)-[4-(3,4-dichloro-phenyl)-pyrrolidin-3-yl]-carbamic acid tert-butyl ester (6.39 g, 67% purity, 0.013 mol) in DMF (45 ml) were added and the reaction mixture was stirred for 19 h at this temperature. It was diluted with ethyl acetate (80 mL) and the organic layer was washed with water (80 mL), aqueous sodium carbonate (1M, 40 mL) and brine (40 mL). The aqueous layers were extracted with ethyl acetate (160 mL). the combined organic layers were dried over sodium sulfate and concentrated. Purification by flash chromatography ($SiO_2$, EtOAc/methanol 100:0 to 80:20) afforded 5.84 g (87%) of the title compound as a light brown foam. ES-MS m/e: 524.1 (M+H+).

f) rac-(3S,4R)-[3-Amino-4-(3,4-dichloro-phenyl)-pyrrolidin-1-yl]-[1-(1-methyl-cyclopropanecarbonyl)-piperidin-4-yl]-methanone To a solution of rac-(3S,4R)-{4-(3,4-dichloro-phenyl)-1-[1-(1-methyl-cyclopropanecarbonyl)-piperidine-4-carbonyl]-pyrrolidin-3-yl}-carbamic acid tert-butyl ester (5.747 g, 0.011 mol) in dichloromethane (55 mL) was added trifluoroacetic acid (8.39 mL, 0.110 mol) and the reaction mixture was stirred for 4 h at ambient temperature. The reaction mixture was basified by addition of aqueous sodium carbonate (1M, 10 mL). The organic layers were washed with water (8 mL) and the aqueous layers were extracted with dichloromethane (10 mL). The combined org. layers were dried over sodium sulfate and concentration afforded 4.30 g (92%) of the title compound as a light brown foam. ES-MS m/e: 524.2 (M+H$^+$).

g) rac-[(3R,4S)-3-(3,4-Dichloro-phenyl)-4-ethylamino-pyrrolidin-1-yl]-[1-(1-methyl-cyclopropanecarbonyl)-piperidin-4-yl]-methanone To a solution of rac-(3S,4R)-[3-Amino-4-(3,4-dichloro-phenyl)-pyrrolidin-1-yl]-[1-(1-methyl-cyclopropanecarbonyl)-piperidin-4-yl]-methanone (50 mg, 0.12 mmol) in ethanol (0.3 mL) were added acetaldehyde (10 uL, 0.18 mmol) and sodiumcyanoborohydride (15 mg, 0.24 mmol) and the reaction mixture was stirred at ambient temperature for 3 h. It was concentrated and the residue separated between water and ethylacetate. The organic layer was dried over sodium sulfate and concentrated. Purification by chromatography (SiO$_2$, dichloromethane:methanol=100:0 to 95:5) afforded the title compound (30 mg, 56%) as a light yellow oil. MS m/e: 452.3 [M]$^+$.

h) rac-{(3S,4R)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester To a solution of rac-[(3R,4S)-3-(3,4-dichloro-phenyl)-4-ethylamino-pyrrolidin-1-yl]-[1-(1-methyl-cyclopropanecarbonyl)-piperidin-4-yl]-methanone (25 mg, 0.06 mmol) in dichloromethane (1 mL) was added N,N-diisopropylethylamine (10 uL, 0.06 mmol). It was cooled to 0° C. and 4-fluorophenyl chloroformate (8 uL, 0.06 mmol) was added and the reaction mixture was stirred for 30 min at this temperature and then 2 h at ambient temperature. Concentration and purification by chromatography (SiO$_2$, ethyl acetate) afforded the title compound (17 mg, 52%) as a colorless foam. MS m/e: 590.4 [M]$^+$.

Example 2 rac-{(3S,4R)-4-(3,4-Dichloro-phenyl)-1-[1-(1-methyl-cyclopropanecarbonyl)-piperidine-4-carbonyl]-pyrrolidin-3-yl}-isopropyl-carbamic acid 4-fluoro-phenyl ester

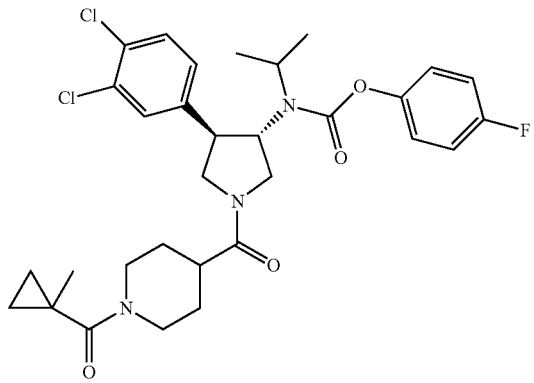 [SMILES: CC(C)N(C(=O)Oc1ccc(F)cc1)[C@@H]1CN(C(=O)C2CCN(C(=O)C3(C)CC3)CC2)C[C@H]1c1ccc(Cl)c(Cl)c1]

a) rac-[(3R,4S)-3-(3,4-Dichloro-phenyl)-4-isopropylamino-pyrrolidin-1-yl]-[1-(1-methyl-cyclopropanecarbonyl)-piperidin-4-yl]-methanone To a solution of rac-(3S,4R)-[3-Amino-4-(3,4-dichloro-phenyl)-pyrrolidin-1-yl]-[1-(1-methyl-cyclopropanecarbonyl)-piperidin-4-yl]-methanone (120 mg, 0.28 mmol) in dichloromethane (1 mL) were added acetone (21 uL, 0.28 mmol) and sodiumtriacetoxy-borohydride (72 mg, 0.34 mmol) and acetic acid (16 uL, 0.28 mmol) and the reaction mixture was stirred at ambient temperature for 3 h. It was diluted with dichloromethane and washed with aqueous sodiumhydrogenecarbonate (1M). The organic layer was dried over sodium sulfate and concentrated affording the title compound (95 mg, 72%) as a light yellow foam. MS m/e: 466.3 [M]$^+$.

b) rac-{(3S,4R)-4-(3,4-Dichloro-phenyl)-1-[1-(1-methyl-cyclopropanecarbonyl)-piperidine-4-carbonyl]-pyrrolidin-3-yl}-isopropyl-carbamic acid 4-fluoro-phenyl ester In analogy to the procedure described for the synthesis of example 1 (step h), the title compound rac-{(3S,4R)-4-(3,4-dichloro-phenyl)-1-[1-(1-methyl-cyclopropanecarbonyl)-piperidine-4-carbonyl]-pyrrolidin-3-yl}-isopropyl-carbamic acid 4-fluoro-phenyl ester was prepared from rac-[(3R,4S)-3-(3,4-Dichloro-phenyl)-4-isopropylamino-pyrrolidin-1-yl]-[1-(1-methyl-cyclopropanecarbonyl)-piperidin-4-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4-fluorophenyl chloroformate and was obtained as a colorless foam. MS m/e: 604.3 [M]$^+$.

Example 3 rac-{(3S,4R)-4-(3,4-Dichloro-phenyl)-1-[1-(1-methyl-cyclopropanecarbonyl)-piperidine-4-carbonyl]-pyrrolidin-3-yl}-isobutyl-carbamic acid 4-fluoro-phenyl ester

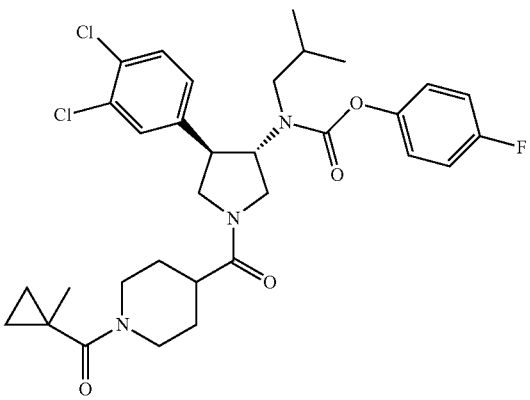 [SMILES: CC(C)CN(C(=O)Oc1ccc(F)cc1)[C@@H]1CN(C(=O)C2CCN(C(=O)C3(C)CC3)CC2)C[C@H]1c1ccc(Cl)c(Cl)c1]

a) rac-[(3R,4S)-3-(3,4-Dichloro-phenyl)-4-isobutylamino-pyrrolidin-1-yl]-[1-(1-methyl-cyclopropanecarbonyl)-piperidin-4-yl]-methanone To a solution of rac-(3S,4R)-[3-Amino-4-(3,4-dichloro-phenyl)-pyrrolidin-1-yl]-[1-(1-methyl-cyclopropanecarbonyl)-piperidin-4-yl]-methanone (150 mg, 0.35 mmol) in dichloromethane (1 mL) were added isobutylaldehyde (39 uL, 0.42 mmol) and sodiumcyanoborohydride (27 mg, 0.42 mmol) and acetic acid (51 uL, 0.88 mmol) and the reaction mixture was stirred at ambient temperature for 3 h. It was diluted with dichloromethane and washed with aqueous sodiumhydrogenecarbonate (1M). The organic layer was dried over sodium sulfate and concentrated affording the title compound (140 mg, 82%) as a light yellow oil. MS m/e: 480.3 [M]+.

b) rac-[(3S,4R)-4-(3,4-Dichloro-phenyl)-1-[1-(1-methyl-cyclopropanecarbonyl)-piperidine-4-carbonyl]-pyrrolidin-3-yl]-isobutyl-carbamic acid 4-fluoro-phenyl ester In analogy to the procedure described for the synthesis of example 1 (step h), the title compound rac-{(3S,4R)-4-(3,4-dichloro-phenyl)-1-[1-(1-methyl cyclopropanecarbonyl)-piperidine-4-carbonyl]-pyrrolidin-3-yl}-isobutyl-carbamic acid 4-fluoro-phenyl ester was prepared from rac-[(3R,4S)-3-(3,4-Dichloro-phenyl)-4-isobutylamino-pyrrolidin-1-yl]-[1-(1-methyl-cyclopropanecarbonyl)-piperidin-4-yl]-methanone instead of rac-{4-[(3S,4R)-3-(3,4-dichloro-phenyl)-4-methylamino-pyrrolidine-1-carbonyl]piperidin-1-yl}-(1-methyl-cyclopropyl)-methanone using 4-fluorophenyl chloroformate and was obtained as a colorless foam. MS m/e: 618.5 [M]+.

Example 4 rac-{(3S,4R)-4-(3,4-Dichloro-phenyl)-1-[1-(1-methyl-cyclopropanecarbonyl)-piperidine-4-carbonyl]-pyrrolidin-3-yl}-cyclopropyl-carbamic acid 4-fluoro-phenyl ester

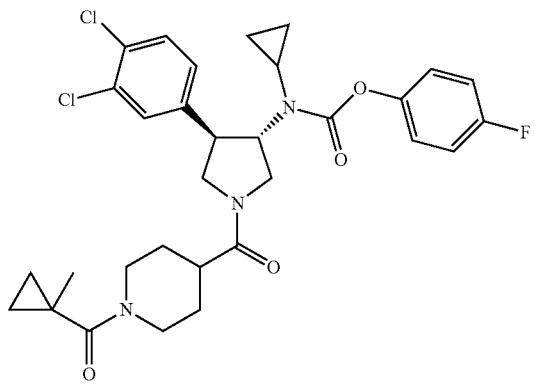 [SMILES: CC1(C(=O)N2CCC(C(=O)N3C[C@@H](N(C(=O)Oc4ccc(F)cc4)C4CC4)[C@H](c4ccc(Cl)c(Cl)c4)C3)CC2)CC1]

a) rac-[(3R,4S)-3-(3,4-Dichloro-phenyl)-4-cyclopropylamino-pyrrolidin-1-yl]-[1-(1-methyl-cyclopropanecarbonyl)-piperidin-4-yl]-methanone To a solution of rac-(3S,4R)-[3-Amino-4-(3,4-dichloro-phenyl)-pyrrolidin-1-yl]-[1-(1-methyl-cyclopropanecarbonyl)-piperidin-4-yl]-methanone (150 mg, 0.35 mmol) in dichloromethane (1 mL) were added ((1-ethoxycyclopropyl)oxy)trimethylsilan (62 uL, 0.35 mmol) and sodiumtrisacetoxyborohydride (90 mg, 0.42 mmol) and acetic acid (20 uL, 0.35 mmol) and the reaction mixture was stirred at ambient temperature for 20 h. It was diluted with dichloromethane and washed with aqueous sodiumhydrogenecarbonate (1M). The organic layer was dried over sodium sulfate and concentrated. Purification by chromatography (SiO2, dichloromethane:methanol=100:0 to 95:5) afforded the title compound (30 mg, 18%) as a light yellow oil. MS m/e: 464.3 [M]+.

b) rac-{(3S,4R)-4-(3,4-Dichloro-phenyl)-1-[1-(1-methyl-cyclopropanecarbonyl)-piperidine-4-carbonyl]-pyrrolidin-3-yl}-cyclopropyl-carbamic acid 4-fluoro-phenyl ester In analogy to the procedure described for the synthesis of example 1 (step h), the title compound rac-{(3S,4R)-4-(3,4-dichloro-phenyl)-1-[1-(1-methyl cyclopropanecarbonyl)-piperidine-4-carbonyl]-pyrrolidin-3-yl}-cyclopropyl-carbamic acid 4-fluoro-phenyl ester was prepared from rac-[(3R,4S)-3-(3,4-Dichloro-phenyl)-4-cyclopropylamino-pyrrolidin-1-yl]-[1-(1-methyl-cyclopropanecarbonyl)-piperidin-4-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4-fluorophenyl chloroformate and was obtained as a colorless foam. MS m/e: 602.3 [M]+.

Example 5

{(3S,4R)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester

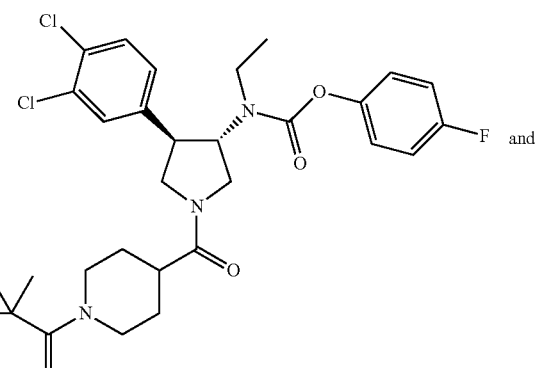

and

Example 6

{(3R,4S)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester

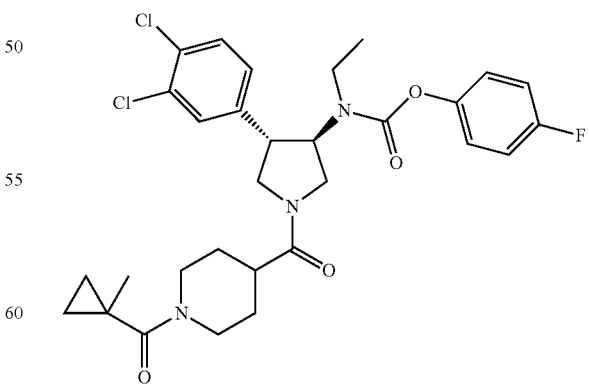

rac-{(3S,4R)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester was subjected to column chromatography on chiral phase to yield {(3S,4R)-4-(3,4-dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester (MS (m/e): 590.3 [M]$^+$) as a colorless foam {(3R,4S)-4-(3,4-dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester (MS (m/e): 590.3 [M]$^+$) as a colorless foam.

Example 7

{(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester

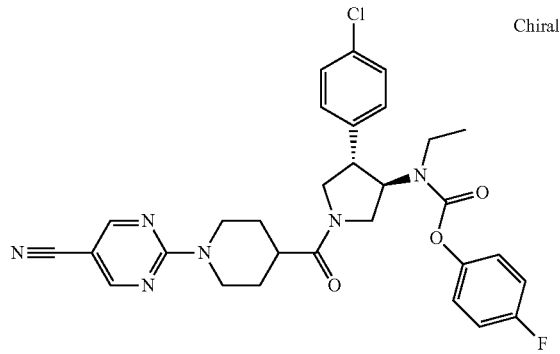 [SMILES: CCN(C(=O)Oc1ccc(F)cc1)[C@H]1CN(C(=O)C2CCN(c3ncc(C#N)cn3)CC2)C[C@@H]1c1ccc(Cl)cc1]

Chiral a) rac-(3R,4S)-1-benzyl-3-(4-chloro-phenyl)-4-nitro-pyrrolidine

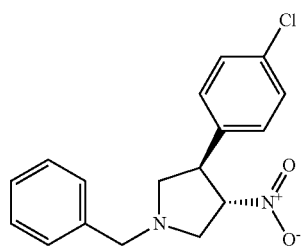 [SMILES: O=[N+]([O-])[C@@H]1CN(Cc2ccccc2)C[C@H]1c1ccc(Cl)cc1]

In analogy to the procedure described for the synthesis of rac-(3R,4S)-1-Benzyl-3-(3,4-dichloro-phenyl)-4-nitro-pyrrolidine (example 1, step a) the title compound was prepared from (E)-1-chloro-4-(2-nitrovinyl)benzene and N-(methoxymethyl)-N-(phenylmethyl)-N-(trimethylsilyl)methylamine as light yellow viscous oil. MS m/e: 317.1 [M+H]$^+$.

b) rac-(3S,4R)-1-benzyl-4-(4-chloro-phenyl)-pyrrolidin-3-ylamine

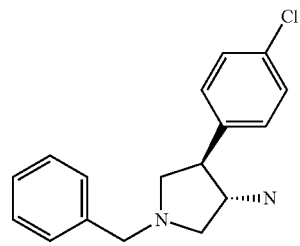 [SMILES: N[C@@H]1CN(Cc2ccccc2)C[C@H]1c1ccc(Cl)cc1]

In analogy to the procedure describe for the synthesis of rac-(3S,4R)-1-Benzyl-4-(3,4-dichloro-phenyl)-pyrrolidin-3-ylamine (example 1, step b) the title compound was prepared from rac-(3R,4S)-1-benzyl-3-(4-chloro-phenyl)-4-nitro-pyrrolidine through reduction with SnCl$_2$ as brown oil. MS m/e: 287.1 [M+H]$^+$.

c) rac-[(3S,4R)-1-Benzyl-4-(4-chloro-phenyl)-pyrrolidin-3-yl]-ethyl-carbamic acid 4-fluoro-phenyl ester

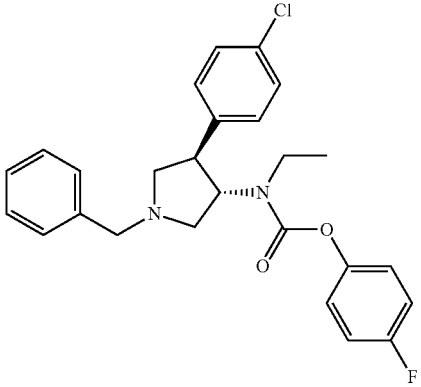 [SMILES: CCN(C(=O)Oc1ccc(F)cc1)[C@@H]1CN(Cc2ccccc2)C[C@H]1c1ccc(Cl)cc1]

A mixture of 2.14 g (7.09 mmol) rac-(3S,4R)-1-benzyl-4-(4-chlorophenyl)-pyrrolidin-3-amine, 540 uL (9.5 mmol) acetaldehyde, 609 uL (10.6 mmol) acetic acid and 2.25 g (10.6 mmol) sodium triacetoxyborohydride was stirred at 20° C. over night. Water and Na$_2$CO$_3$ aq. was added and the mixture was extracted with ethyl acetate. The combined organic layers were dried with Na$_2$SO$_4$ and evaporated to dryness. The residue was taken up in 60 mL DCM. 1.15 g DIPEA (8.86 mmol) and 43.3 mg DMAP (354 μmol) was added. The brownish solution was cooled with an ice-bath. A solution of 1.48 g (8.51 mmol) 4-fluorophenyl chloroformate in 15 mL DCM was added drop-wise and the mixture was stirred at 0-5° C. for 1 h. Na$_2$CO$_3$ aq. was added and the mixture was extracted with DCM. The combined organic layers were washed with brine, dried with Na$_2$SO$_4$ and evaporated to dryness. The residue was purified by flash column chromatography on silica eluting with a gradient formed from TBDME and heptane to yield after evaporation of the product containing fractions 1.62 g (50%) of the title compound as yellow oil. MS m/e: 453.3 [M+H]$^+$.

d) rac-4-{(3R,4S)-3-(4-Chloro-phenyl)-4-[ethyl-(4-fluoro-phenoxycarbonyl)-amino]-pyrrolidine-1-carbonyl}-piperidine-1-carboxylic acid tert-butyl ester

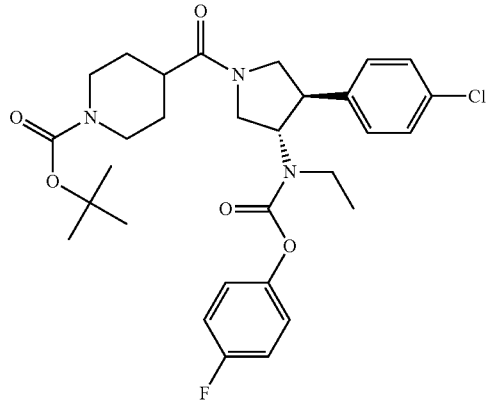 [SMILES: CCN(C(=O)Oc1ccc(F)cc1)[C@@H]1CN(C(=O)C2CCN(C(=O)OC(C)(C)C)CC2)C[C@H]1c1ccc(Cl)cc1]

A mixture of 1.62 g (3.58 mmol) rac-4-fluorophenyl (3S,4R)-1-benzyl-4-(4-chlorophenyl) pyrrolidin-3-yl(ethyl)carbamate and 624 mg (4.83 mmol) DIPEA in 25 mL toluene was cooled to 0-5° C. 690 mg (4.83 mmol) 1-chloroethyl chloroformate was added and the mixture was stirred over night at ambient temperature and evaporated to dryness. The residue was dried under high vacuum at 60-70° C. to yield rac-[(3S,4R)-4-(4-Chloro-phenyl)-pyrrolidin-3-yl]-ethyl-carbamic acid 4-fluoro-phenyl ester. The residue was dissolved in 25 mL methanol, stirred for 90 min and evaporated to dryness. The residue was taken up in 25 mL DMF and 2.5 g (19.3 mmol) DIPEA was added. A solution of 738 mg (3.22 mmol) 1-(tert-butoxycarbonyl)piperidine-4-carboxylic acid and 1.35 g (3.54 mmol) HATU in 25 mL DMF was added and the mixture was stirred for 30 min at room temperature and evaporated under high vacuum. The residue was dissolved in ethyl acetate and washed with 10% aq.Na$_2$CO$_3$ and brine. The aqueous layers were extracted with ethyl acetate and the combined organic layers were dried over Na$_2$SO$_4$, filtered off and concentrated under vacuum. The residue was purified by column chromatography over silica eluting with a gradient formed from ethyl acetate and heptane to yield after evaporation of the product containing fractions 1.8 g (97%) of the title compound as light brown foam. MS m/e: 574.2 [M+H]$^+$.

e) 4-{(3R,4S)-3-(4-Chloro-phenyl)-4-[ethyl-(4-fluoro-phenoxycarbonyl)-amino]-pyrrolidine-1-carbonyl}-piperidine-1-carboxylic acid tert-butyl ester

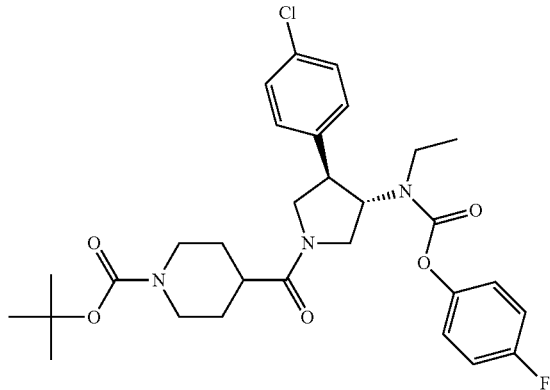 [SMILES: CCN(C(=O)Oc1ccc(F)cc1)[C@@H]1CN(C(=O)C2CCN(C(=O)OC(C)(C)C)CC2)C[C@H]1c1ccc(Cl)cc1]

rac-4-{(3R,4S)-3-(4-Chloro-phenyl)-4-[ethyl-(4-fluoro-phenoxycarbonyl)-amino]-pyrrolidine-1-carbonyl}-piperidine-1-carboxylic acid tert-butyl ester was subjected to separation by chiral HPLC eluting with i-propanol/heptane. After evaporation of the product containing fractions the title compound was obtained as yellow viscous oil. MS m/e: 474.3 [M-Boc]$^+$.
And 4-{(3S,4R)-3-(4-Chloro-phenyl)-4-[ethyl-(4-fluoro-phenoxycarbonyl)-amino]-pyrrolidine-1-carbonyl}-piperidine-1-carboxylic acid tert-butyl ester

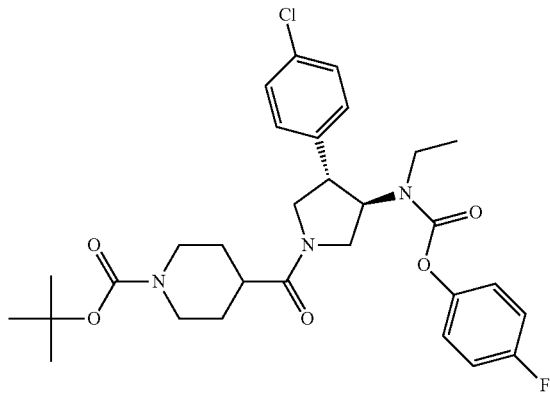 [SMILES: CCN(C(=O)Oc1ccc(F)cc1)[C@H]1CN(C(=O)C2CCN(C(=O)OC(C)(C)C)CC2)C[C@@H]1c1ccc(Cl)cc1]

rac-4-{(3R,4S)-3-(4-Chloro-phenyl)-4-[ethyl-(4-fluoro-phenoxycarbonyl)-amino]-pyrrolidine-1-carbonyl}-piperidine-1-carboxylic acid tert-butyl ester was subjected to separation by chiral HPLC eluting with i-propanol/heptane. After evaporation of the product containing fractions the title compound was obtained as yellow viscous oil. MS m/e: 474.3 [M-Boc]$^+$.

f) [(3R,4S)-4-(4-Chloro-phenyl)-1-(piperidine-4-carbonyl)-pyrrolidin-3-yl]-ethyl-carbamic acid 4-fluoro-phenyl ester

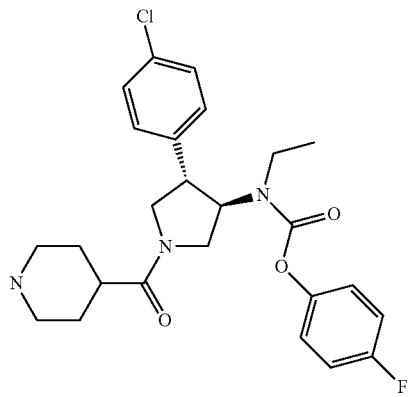 [SMILES: CCN(C(=O)Oc1ccc(F)cc1)[C@H]1CN(C(=O)C2CCNCC2)C[C@@H]1c1ccc(Cl)cc1]

A mixture of 804 mg (1.4 mmol) 4-{(3S,4R)-3-(4-Chloro-phenyl)-4-[ethyl-(4-fluoro-phenoxycarbonyl)-amino]-pyrrolidine-1-carbonyl}-piperidine-1-carboxylic acid tert-butyl ester and 1.6 g (14 mmol) TFA in 25 mL DCM was stirred for 5 h at room temperature. Water and 2N NaOH aq. was added and the mixture was extracted with DCM. The combined organic layers were dried over Na$_2$SO$_4$, filtered off and evaporated to yield 577 mg (87%) of the title compound as yellow foam. MS m/e: 474.3 [M+H]$^+$.

g) {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester A mixture of 94.7 mg (0.2 mmol)[(3R,4S)-4-(4-Chloro-phenyl)-1-(piperidine-4-carbonyl)-pyrrolidin-3-yl]-ethyl-carbamic acid 4-fluoro-phenyl ester, 83.7 mg (0.3 mmol) 2-chloropyrimidine-5-carbonitrile and 129 mg (1 mmol) DIPEA in 2.5 mL DMF was shaken a for 22 h at 65° C. The mixture was subjected to preparative HPLC purification on reversed phase eluting with a gradient formed from acetonitrile, water and NEt$_3$. The product containing fraction were evaporated to access 58 mg (51%) of the title compound as off-white solid. MS m/e: 577.3 [M+H]$^+$.

Example 8

[(3R,4S)-1-(5'-Acetyl-3,4,5,6-tetrahydro-2H-[1,2']bipyridinyl-4-carbonyl)-4-(4-chloro-phenyl)-pyrrolidin-3-yl]-ethyl-carbamic acid 4-fluoro-phenyl ester

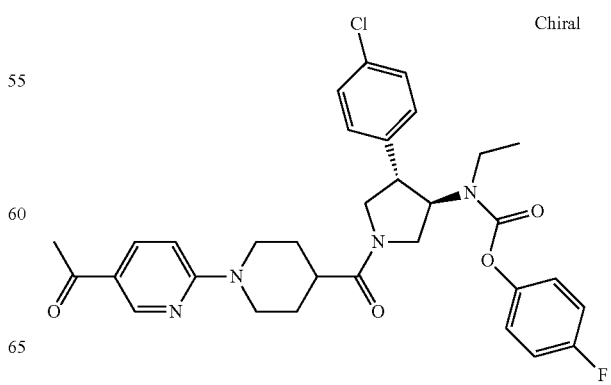

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3R,4S)-4-(4-Chloro-phenyl)-1-(piperidine-4-carbonyl)-pyrrolidin-3-yl]-ethyl-carbamic acid 4-fluoro-phenyl ester and 1-(6-bromopyridin-3-yl)ethanone as off-white solid. MS m/e: 593.4 [M+H]+.

Example 9

[(3R,4S)-4-(4-Chloro-phenyl)-1-(4'-cyano-3,4,5,6-tetrahydro-2H-[1,2']bipyridinyl-4-carbonyl)-pyrrolidin-3-yl]-ethyl-carbamic acid 4-fluoro-phenyl ester

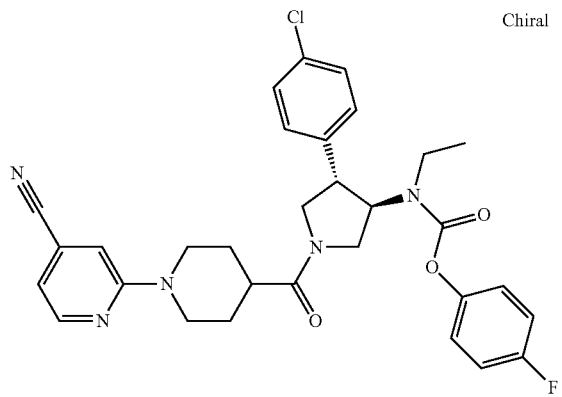 [SMILES: CCN(C(=O)Oc1ccc(F)cc1)[C@H]1CN(C(=O)C2CCN(c3cc(C#N)ccn3)CC2)C[C@@H]1c1ccc(Cl)cc1]

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3R,4S)-4-(4-Chloro-phenyl)-1-(piperidine-4-carbonyl)-pyrrolidin-3-yl]-ethyl-carbamic acid 4-fluoro-phenyl ester and 2-bromoisonicotinonitrile as off-white solid. MS m/e: 576.3 [M+H]+.

Example 10

[(3R,4S)-4-(4-Chloro-phenyl)-1-(5'-methanesulfonyl-3,4,5,6-tetrahydro-2H-[1,2']bipyridinyl-4-carbonyl)-pyrrolidin-3-yl]-ethyl-carbamic acid 4-fluoro-phenyl ester

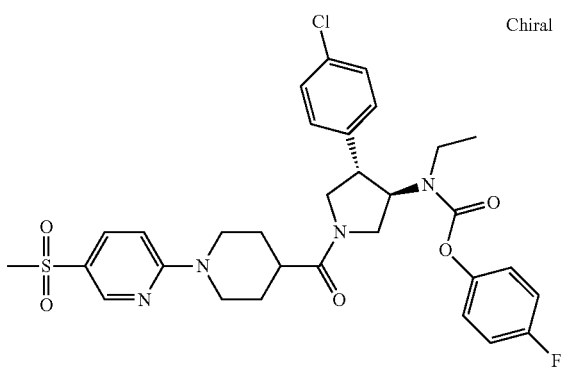 [SMILES: CCN(C(=O)Oc1ccc(F)cc1)[C@H]1CN(C(=O)C2CCN(c3ccc(S(C)(=O)=O)cn3)CC2)C[C@@H]1c1ccc(Cl)cc1]

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3R,4S)-4-(4-Chloro-phenyl)-1-(piperidine-4-carbonyl)-pyrrolidin-3-yl]-ethyl-carbamic acid 4-fluoro-phenyl ester and 2-bromo-5-(methylsulfonyl)pyridine as off-white solid. MS m/e: 629.3 [M+H]+.

Example 11

{(3R,4S)-4-(4-Chloro-phenyl)-1-[1-(5-cyano-pyrazin-2-yl)-piperidine-4-carbonyl]-pyrrolidin-3-yl}-ethyl-carbamic acid 4-fluoro-phenyl ester

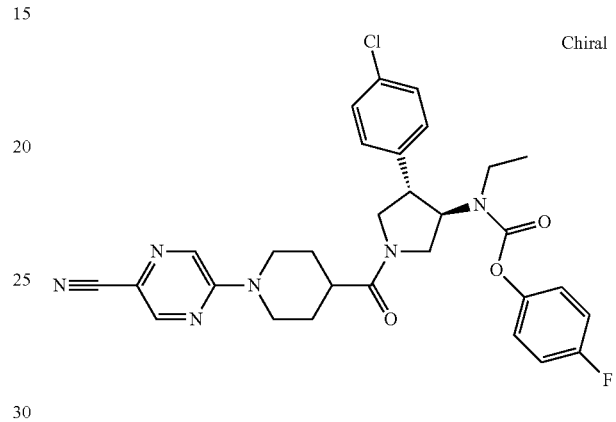

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3R,4S)-4-(4-Chloro-phenyl)-1-(piperidine-4-carbonyl)-pyrrolidin-3-yl]-ethyl-carbamic acid 4-fluoro-phenyl ester and 5-bromopyrazine-2-carbonitrile as off-white solid. MS m/e: 577.3 [M+H]+.

Example 12

{(3R,4S)-4-(4-Chloro-phenyl)-1-[1-(6-cyano-pyridazin-3-yl)-piperidine-4-carbonyl]-pyrrolidin-3-yl}-ethyl-carbamic acid 4-fluoro-phenyl ester

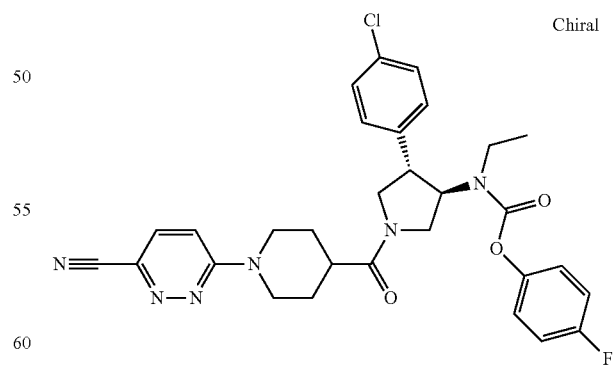

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3R,4S)-4-(4-Chloro-phenyl)-1-(piperidine-4-carbonyl)-pyrrolidin-3-yl]-ethyl-carbamic acid 4-fluoro-phenyl ester and 6-chloropyridazine-3-carbonitrile as off-white solid. MS m/e: 577.3 [M+H]+.

Example 13

{(3S,4R)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester

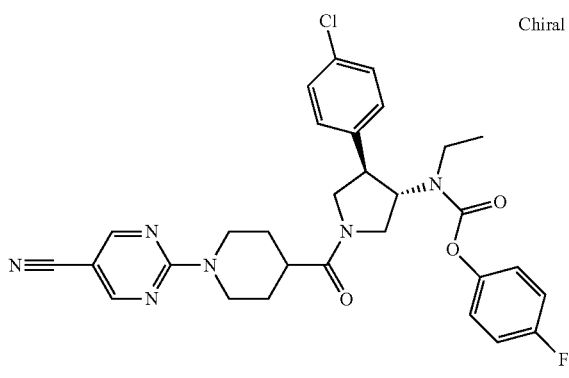 [SMILES: CCN(C(=O)Oc1ccc(F)cc1)[C@@H]1CN(C(=O)C2CCN(c3ncc(C#N)cn3)CC2)C[C@H]1c1ccc(Cl)cc1]

a) [(3S,4R)-4-(4-Chloro-phenyl)-1-(piperidine-4-carbonyl)-pyrrolidin-3-yl]-ethyl-carbamic acid 4-fluoro-phenyl ester

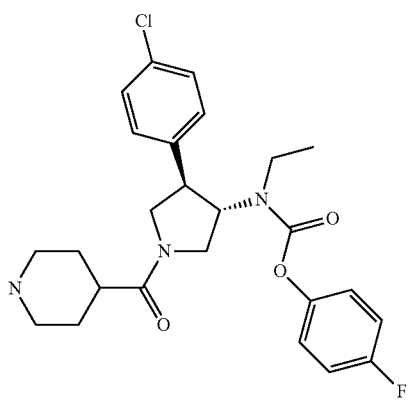 [SMILES: CCN(C(=O)Oc1ccc(F)cc1)[C@@H]1CN(C(=O)C2CCNCC2)C[C@H]1c1ccc(Cl)cc1]

In analogy to the procedure described for the synthesis of [(3R,4S)-4-(4-Chloro-phenyl)-1-(piperidine-4-carbonyl)-pyrrolidin-3-yl]-ethyl-carbamic acid 4-fluoro-phenyl ester the title compound was prepared from 4-{(3R,4S)-3-(4-Chloro-phenyl)-4-[ethyl-(4-fluoro-phenoxycarbonyl)-amino]-pyrrolidine-1-carbonyl}-piperidine-1-carboxylic acid tert-butyl ester through cleavage of the protecting group with TFA. The title compound was obtained as yellow foam. MS m/e: 474.3 [M+H]+.

b) {(3S,4R)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from) [(3S,4R)-4-(4-Chloro-phenyl)-1-(piperidine-4-carbonyl)-pyrrolidin-3-yl]-ethyl-carbamic acid 4-fluoro-phenyl ester and 6-chloropyridazine-3-carbonitrile as off-white solid. MS m/e: 577.3 [M+H]+.

Example 14

[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-ethyl-carbamic acid 4-fluoro-phenyl ester

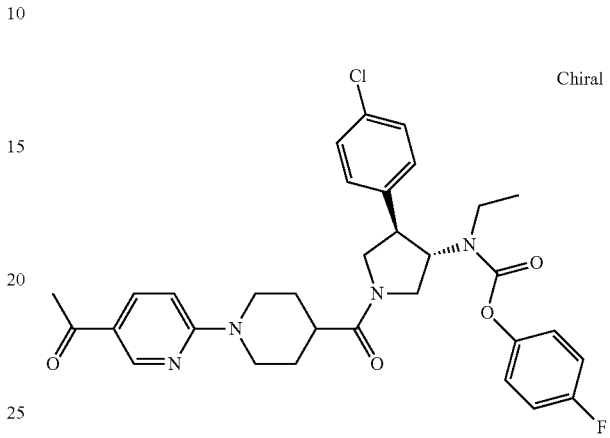

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from)[3S,4R)-4-(4-Chloro-phenyl)-1-(piperidine-4-carbonyl)-pyrrolidin-3-yl]-ethyl-carbamic acid 4-fluoro-phenyl ester and 1-(6-bromopyridin-3-yl)ethanone as off-white solid. MS m/e: 593.4 [M+H]+.

Example 15

[(3S,4R)-4-(4-Chloro-phenyl)-1-(4'-cyano-3,4,5,6-tetrahydro-2H-[1,2']bipyridinyl-4-carbonyl)-pyrrolidin-3-yl]-ethyl-carbamic acid 4-fluoro-phenyl ester

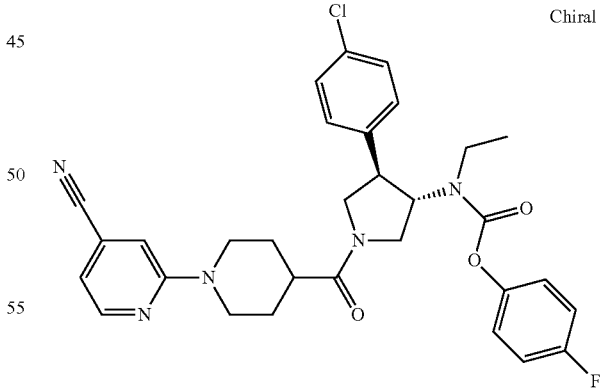

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from) [(3S,4R)-4-(4-Chloro-phenyl)-1-(piperidine-4-carbonyl)-pyrrolidin-3-yl]ethyl-carbamic acid 4-fluoro-phenyl ester and 2-bromoisonicotinonitrile as off-white solid. MS m/e: 576.3 [M+H]+.

Example 16

[(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-ethyl-carbamic acid 4-fluoro-phenyl ester

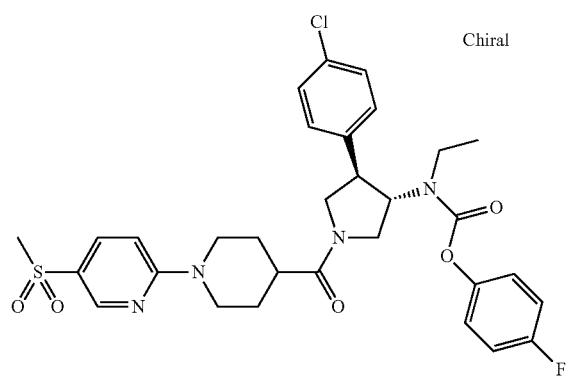 [SMILES: CCN(C(=O)Oc1ccc(F)cc1)[C@@H]1CN(C(=O)C2CCN(c3ccc(S(C)(=O)=O)cn3)CC2)C[C@H]1c1ccc(Cl)cc1]

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from) [(3S,4R)-4-(4-Chloro-phenyl)-1-(piperidine-4-carbonyl)-pyrrolidin-3-yl]-ethyl-carbamic acid 4-fluoro-phenyl ester and 2-bromo-5-(methylsulfonyl)pyridine as off-white solid. MS m/e: 629.3 [M+H]$^+$.

Example 17

{(3S,4R)-4-(4-Chloro-phenyl)-1-[1-(5-cyano-pyrazin-2-yl)-piperidine-4-carbonyl]-pyrrolidin-3-yl}-ethyl-carbamic acid 4-fluoro-phenyl ester

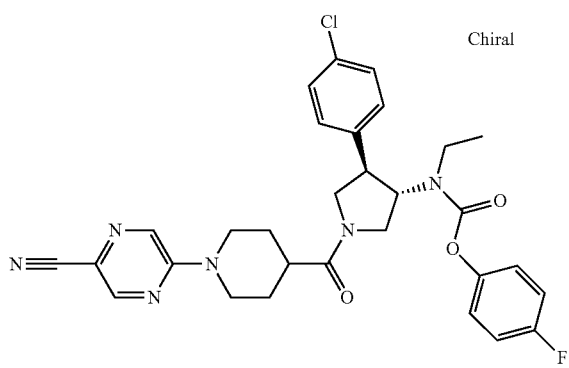 [SMILES: CCN(C(=O)Oc1ccc(F)cc1)[C@@H]1CN(C(=O)C2CCN(c3cnc(C#N)cn3)CC2)C[C@H]1c1ccc(Cl)cc1]

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from) [(3S,4R)-4-(4-Chloro-phenyl)-1-(piperidine-4-carbonyl)-pyrrolidin-3-yl]-ethyl-carbamic acid 4-fluoro-phenyl ester and 5-bromopyrazine-2-carbonitrile as off-white solid. MS m/e: 577.3 [M+H]$^+$.

Example 18

{(3S,4R)-4-(4-Chloro-phenyl)-1-[1-(6-cyano-pyridazin-3-yl)-piperidine-4-carbonyl]-pyrrolidin-3-yl}-ethyl-carbamic acid 4-fluoro-phenyl ester

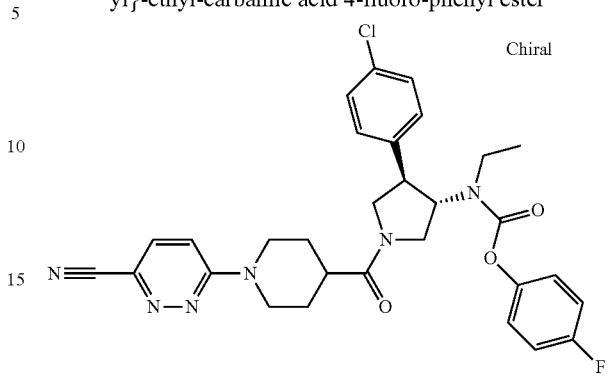

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 6-chloropyridazine-3-carbonitrile as off-white solid. MS m/e: 577.3 [M+H]$^+$.

Example 19

[(3R,4S)-4-(4-Chloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester

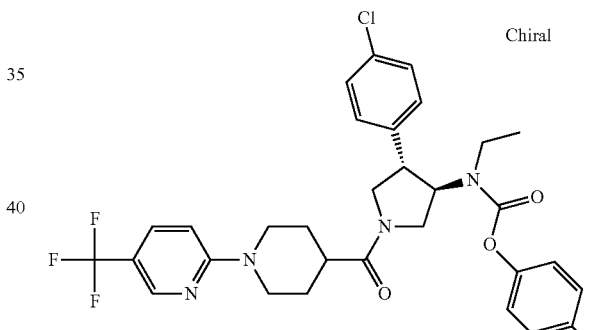

and

Example 20

[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester

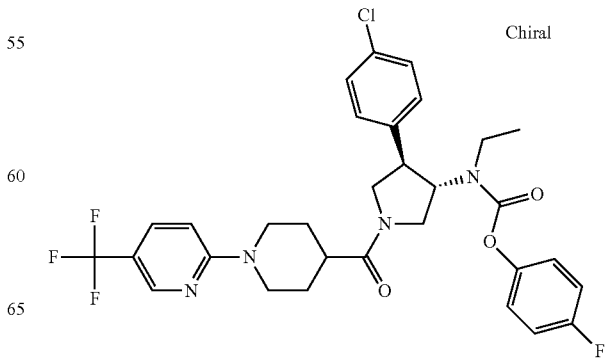

a) rac-[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester A mixture of 125 mg (0.456 mmol) rac-[(3S,4R)-4-(4-Chloro-phenyl)-pyrrolidin-3-yl]-ethyl-carbamic acid 4-fluoro-phenyl ester, 198 mg (0.547 mmol) 1-(5-(trifluoromethyl)pyridin-2-yl)piperidine-4-carboxylic acid, 208 mg (0.547 mmol) HATU and 353 mg (2.73 mmol) DIPEA in 10 mL DMF and stirred for 1 h ar room temperature. The mixture was concentrated and DMF and DIPEA was added and subjected to purification by preparative HPLC on reversed phase eluting with a gradient formed from acetonitrile, water and NEt₃. The product containing fractions were evaporated to yield 187 mg (66%) of the title compound as light brown viscous oil. MS m/e: 619.4 [M+H]⁺.

The racemic material was subjected to separation on CHIRALPAK AD eluting with i-propanol/heptane. [(3R,4S)-4-(4-Chloro-phenyl)-1-(5'-trifluoromethyl-3,4,5,6-tetrahydro-2H-[1,2]bipyridinyl-4-carbonyl)-pyrrolidin-3-yl]-ethyl-carbamic acid 4-fluoro-phenyl ester was obtained as light yellow solid. MS m/e: 619.4 [M+H]⁺ and [(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester was obtained as light yellow solid. MS m/e: 619.4 [M+H]⁺

Example 21

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-ethyl-carbamic acid 4-fluoro-phenyl ester

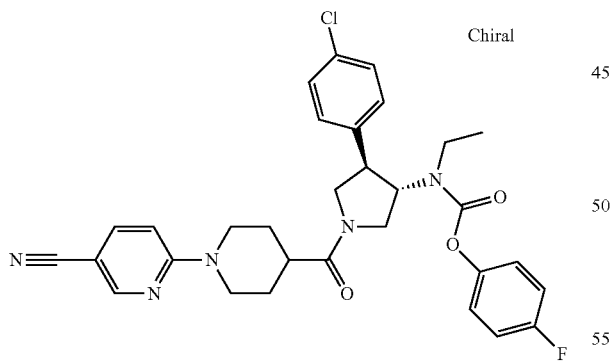

In analogy to the procedure described for the synthesis of [(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester the title compound was prepared from rac-[(3S,4R)-4-(4-Chloro-phenyl)-pyrrolidin-3-yl]-ethyl-carbamic acid 4-fluoro-phenyl ester and 1-(5-cyanopyridin-2-yl)piperidine-4-carboxylic acid with subsequent separation via chiral chromatography on Chiralpak AD as off-white solid. MS m/e: 576.3 [M+H]⁺

Example 22

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-ethyl-carbamic acid 4-fluoro-phenyl ester

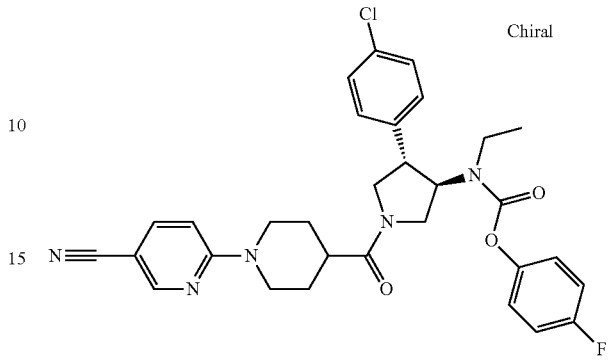

In analogy to the procedure described for the synthesis of [(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester the title compound was prepared from rac-[(3S,4R)-4-(4-Chloro-phenyl)-pyrrolidin-3-yl]-ethyl-carbamic acid 4-fluoro-phenyl ester and 1-(5-cyanopyridin-2-yl)piperidine-4-carboxylic acid with subsequent separation via chiral chromatography on Chiralpak AD as off-white solid. MS m/e: 576.3 [M+H]⁺

Example 23

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-isopropyl-carbamic acid 4-fluoro-phenyl ester

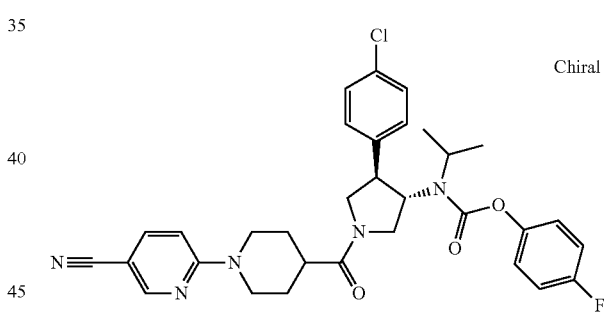

a) rac-[(3S,4R)-1-Benzyl-4-(4-chloro-phenyl)-pyrrolidin-3-yl]-isopropyl-carbamic acid 4-fluoro-phenyl ester

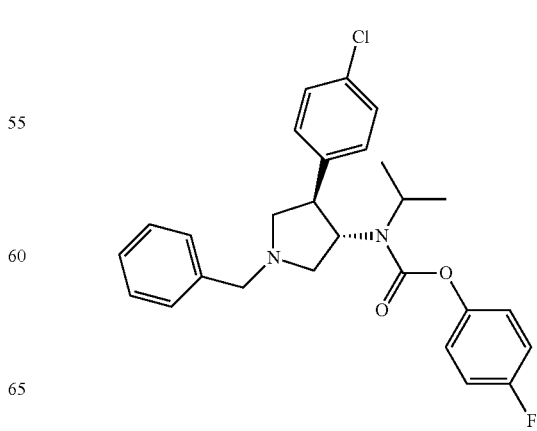

A mixture of 3.1 g (10.8 mmol) rac-(3S,4R)-1-benzyl-4-(4-chlorophenyl)pyrrolidin-3-amine, 785 mg (13.5 mmol) acetone, 974 mg (16.2 mmol) acetic acid and 3.44 g (16.2 mmol) sodium triacteoxyborohydride in 50 mL THF was stirred for 4 h at room temperature. Water and $Na_2CO_3$ aq. was added and the mixture was extracted with ethyl acetate. The organic layer was washed with brine, dried with $Na_2SO_4$, filtered off and evaporated to dryness. The residue was dissolved in 50 mL DCM and 1.75 g (13.5 mmol) DIPEA and 13.2 mg (0.1 mmol) DMAP was added. The mixture was cooled to 0-5° C. and 2.08 g (11.9 mmol) 4-fluorophenyl chloroformate in 20 mL DCM was added. The mixture was stirred at room temperature over night and evaporated to dryness. The residue was purified by flash column chromatography on silica eluting with a gradient formed from TBME and heptane. The product containing fractions were evaporated to yield 3.1 g (61%) of the title compound as light yellow viscous oil. MS m/e: 467.2 $[M+H]^+$ b) 4-{(3R,4S)-3-(4-Chloro-phenyl)-4-[(4-fluoro-phenoxycarbonyl)-isopropyl-amino]-pyrrolidine-1-carbonyl}-piperidine-1-carboxylic acid tert-butyl ester

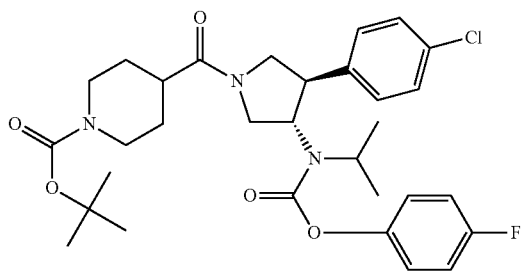 [SMILES: CC(C)N(C(=O)Oc1ccc(F)cc1)[C@@H]1CN(C(=O)C2CCN(C(=O)OC(C)(C)C)CC2)C[C@H]1c1ccc(Cl)cc1]

and

4-{(3S,4R)-3-(4-Chloro-phenyl)-4-[(4-fluoro-phenoxycarbonyl)-isopropyl-amino]-pyrrolidine-1-carbonyl}-piperidine-1-carboxylic acid tert-butyl ester

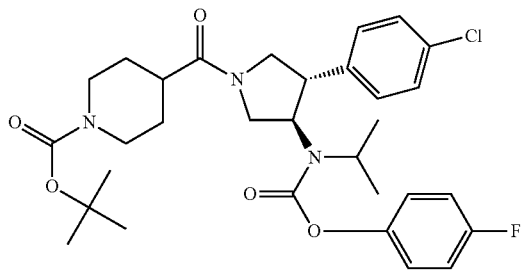 [SMILES: CC(C)N(C(=O)Oc1ccc(F)cc1)[C@H]1CN(C(=O)C2CCN(C(=O)OC(C)(C)C)CC2)C[C@@H]1c1ccc(Cl)cc1]

In analogy to the procedure described for the synthesis of rac-4-{(3R,4S)-3-(4-Chloro-phenyl)-4-[ethyl-(4-fluoro-phenoxycarbonyl)-amino]-pyrrolidine-1-carbonyl}-piperidine-1-carboxylic acid tert-butyl ester the title compounds were prepared from rac-[(3S,4R)-1-Benzyl-4-(4-chloro-phenyl)-pyrrolidin-3-yl]-isopropyl-carbamic acid 4-fluoro-phenyl ester by cleavage of the benzyl group and subsequent coupling with 1-(tert-butoxycarbonyl)piperidine-4-carboxylic acid. The resulting rac-4-{(3S,4R)-3-(4-Chloro-phenyl)-4-[(4-fluoro-phenoxycarbonyl)-isopropyl-amino]-pyrrolidine-1-carbonyl}-piperidine-1-carboxylic acid tert-butyl ester was subjected to separation by chiral HPLC on CHIRALPAK AD eluting with i-propanol/heptane. After evaporation of the product containing fractions 4-{(3S,4R)-3-(4-Chloro-phenyl)-4-[(4-fluoro-phenoxycarbonyl)-isopropyl-amino]-pyrrolidine-1-carboxylic acid tert-butyl ester was obtained as yellow viscous oil. MS m/e: 588.3 $[M+H]^+$. 4-{(3R,4S)-3-(4-Chloro-phenyl)-4-[(4-fluoro-phenoxycarbonyl)-isopropyl-amino]-pyrrolidine-1-carbonyl}-piperidine-1-carboxylic acid tert-butyl ester was obtained as yellow viscous oil. MS m/e: 588.3 $[M+H]^+$.

c) [(3S,4R)-4-(4-Chloro-phenyl)-1-(piperidine-4-carbonyl)-pyrrolidin-3-yl]-isopropyl-carbamic acid 4-fluoro-phenyl ester

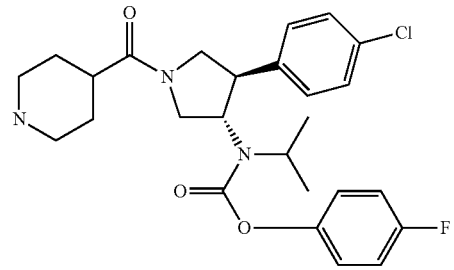 [SMILES: CC(C)N(C(=O)Oc1ccc(F)cc1)[C@@H]1CN(C(=O)C2CCNCC2)C[C@H]1c1ccc(Cl)cc1]

In analogy to the procedure described for the synthesis of [(3R,4S)-4-(4-Chloro-phenyl)-1-(piperidine-4-carbonyl)-pyrrolidin-3-yl]-ethyl-carbamic acid 4-fluoro-phenyl ester the title compound was prepared from 4-{(3R,4S)-3-(4-Chloro-phenyl)-4-[(4-fluoro-phenoxycarbonyl)-isopropyl-amino]-pyrrolidine-1-carbonyl}-piperidine-1-carboxylic acid tert-butyl ester through cleavage of the protecting group with TFA. The title compound was obtained as off-white foam. MS m/e: 488.3 $[M+H]^+$.

d) [(3S,4R)-4-(4-Chloro-phenyl)-1-(5'-cyano-3,4,5,6-tetrahydro-2H-[1,2']bipyridinyl-4-carbonyl)-pyrrolidin-3-yl]-isopropyl-carbamic acid 4-fluoro-phenyl ester In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3S,4R)-4-(4-Chloro-phenyl)-1-(piperidine-4-carbonyl)-pyrrolidin-3-yl]-isopropyl-carbamic acid 4-fluoro-phenyl ester and 6-bromonicotinonitrile as off-white solid. MS m/e: 590.4 $[M+H]^+$.

Example 24

[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-isopropyl-carbamic acid 4-fluoro-phenyl ester

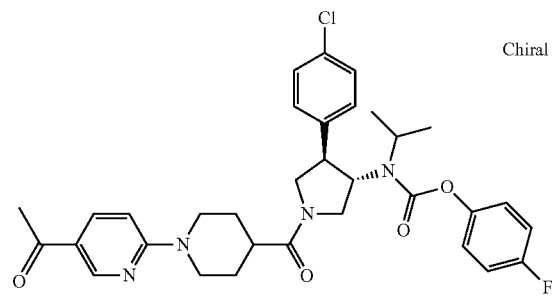 [SMILES: CC(=O)c1ccc(N2CCC(C(=O)N3C[C@@H](N(C(=O)Oc4ccc(F)cc4)C(C)C)[C@H](c4ccc(Cl)cc4)C3)CC2)nc1]

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from {(3S,4R)-4-(4-Chloro-phenyl)-1-(piperidine-4-carbonyl)-pyrrolidin-3-yl}-isopropyl-carbamic acid 4-fluoro-phenyl ester and 1-(6-bromopyridin-3-yl)ethanone as off-white solid. MS m/e: 607.3 [M+H]+.

Example 25

[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-isopropyl-carbamic acid 4-fluoro-phenyl ester

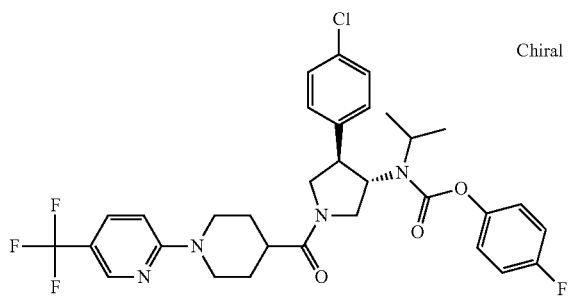 [SMILES: CC(C)N(C(=O)Oc1ccc(F)cc1)[C@@H]1CN(C(=O)C2CCN(c3ccc(C(F)(F)F)cn3)CC2)C[C@H]1c1ccc(Cl)cc1]

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3S,4R)-4-(4-Chloro-phenyl)-1-(piperidine-4-carbonyl)-pyrrolidin-3-yl]-isopropyl-carbamic acid 4-fluoro-phenyl ester and 2-bromo-5-(trifluoromethyl)pyridine as off-white solid. MS m/e: 633.4 [M+H]+.

Example 26

{(3S,4R)-4-(4-Chloro-phenyl)-1-[1-(6-cyano-pyridazin-3-yl)-piperidine-4-carbonyl]-pyrrolidin-3-yl}-isopropyl-carbamic acid 4-fluoro-phenyl ester

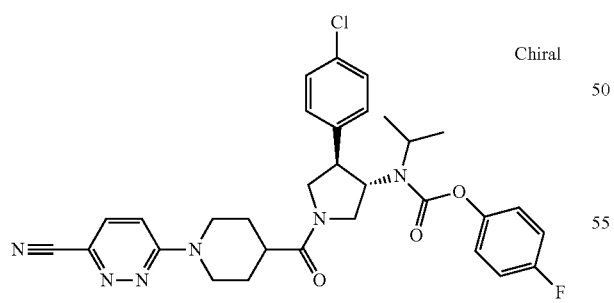

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3S,4R)-4-(4-Chloro-phenyl)-1-(piperidine-4-carbonyl)-pyrrolidin-3-yl]-isopropyl-carbamic acid 4-fluoro-phenyl ester and 6-chloropyridazine-3-carbonitrile as light brown solid. MS m/e: 591.3 [M+H]+.

Example 27

{(3S,4R)-4-(4-Chloro-phenyl)-1-[1-(5-cyano-pyrazin-2-yl)-piperidine-4-carbonyl]-pyrrolidin-3-yl}-isopropyl-carbamic acid 4-fluoro-phenyl ester

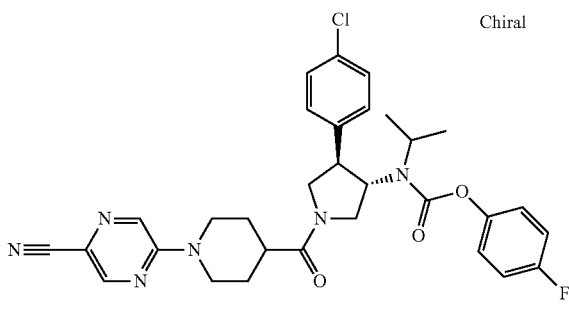 [SMILES: CC(C)N(C(=O)Oc1ccc(F)cc1)[C@@H]1CN(C(=O)C2CCN(c3cnc(C#N)cn3)CC2)C[C@H]1c1ccc(Cl)cc1]

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3S,4R)-4-(4-Chloro-phenyl)-1-(piperidine-4-carbonyl)-pyrrolidin-3-yl]-isopropyl-carbamic acid 4-fluoro-phenyl ester and 5-chloropyrazine-2-carbonitrile as light brown solid. MS m/e: 591.3 [M+H]+.

Example 28

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-isopropyl-carbamic acid 4-fluoro-phenyl ester

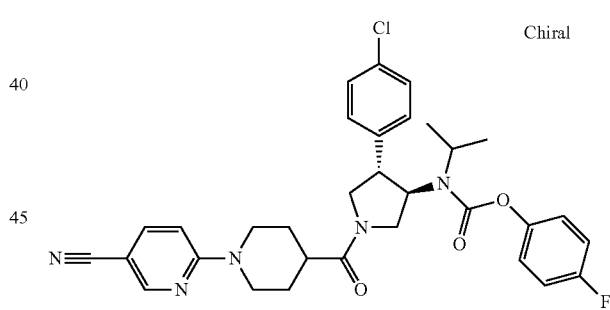

a) [(3R,4S)-4-(4-Chloro-phenyl)-1-(piperidine-4-carbonyl)-pyrrolidin-3-yl]-isopropyl-carbamic acid 4-fluoro-phenyl ester

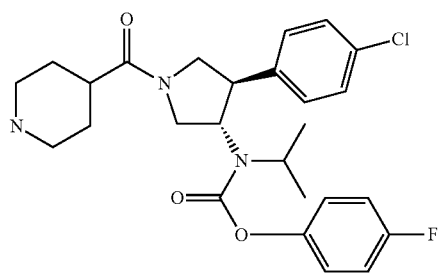 [SMILES: CC(C)N(C(=O)Oc1ccc(F)cc1)[C@@H]1CN(C(=O)C2CCNCC2)C[C@H]1c1ccc(Cl)cc1]

In analogy to the procedure described for the synthesis of [(3R,4S)-4-(4-Chloro-phenyl)-1-(piperidine-4-carbonyl)-pyrrolidin-3-yl]-ethyl-carbamic acid 4-fluoro-phenyl ester the title compound was prepared from 4-{(3S,4R)-3-(4-Chloro-phenyl)-4-[(4-fluoro-phenoxycarbonyl)-isopropyl-amino]-pyrrolidine-1-carbonyl}-piperidine-1-carboxylic acid tert-butyl ester through cleavage of the protecting group with TFA. The title compound was obtained as off-white foam. MS m/e: 488.3 [M+H]⁺.

b) [(3R,4S)-4-(4-Chloro-phenyl)-1-(5'-cyano-3,4,5,6-tetrahydro-2H-[1,2']bipyridinyl-4-carbonyl)-pyrrolidin-3-yl]-isopropyl-carbamic acid 4-fluoro-phenyl ester In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3R,4S)-4-(4-Chloro-phenyl)-1-(piperidine-4-carbonyl)-pyrrolidin-3-yl]-isopropyl-carbamic acid 4-fluoro-phenyl ester and 6-bromonicotinonitrile as off-white solid. MS m/e: 590.2 [M+H]⁺.

Example 29

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-cyclopropyl-carbamic acid 4-fluoro-phenyl ester

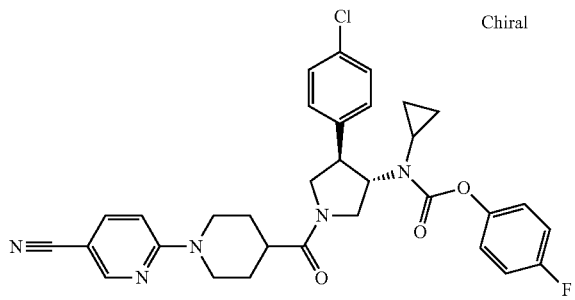 [SMILES: N#Cc1ccc(N2CCC(C(=O)N3C[C@@H](N(C(=O)Oc4ccc(F)cc4)C4CC4)[C@H](c4ccc(Cl)cc4)C3)CC2)nc1]

a) rac-[(3S,4R)-1-Benzyl-4-(4-chloro-phenyl)-pyrrolidin-3-yl]-cyclopropyl-amine

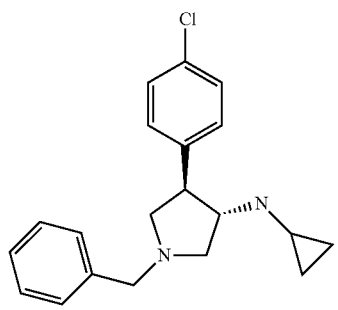 [SMILES: Clc1ccc([C@@H]2CN(Cc3ccccc3)C[C@H]2NC2CC2)cc1]

A mixture of 3.75 g (13.1 mmol) rac-(3S,4R)-1-benzyl-4-(4-chlorophenyl)pyrrolidin-3-amine, 3.14 g (52 mmol) acetic acid and 2.62 g (15 mmol) (1-ethoxycyclopropoxy)trimethylsilane in 15 mL methanol was stirred 1 h at room temperature and 3 h at reflux and evaporated to dryness. The residue was taken up in 35 mL THF and added to a mixture formed from 989 mg (26 mmol) sodium borohydride in 15 mL THF which was treated at 0-5° C. with 3.7 g (26 mmol) boron trifluoride etherate and stirred 1 h. The mixture was stirred at room temperature over night, water and 4N NaOH aq. was added and extracted with ethyl acetate. The organic layer were washed with brine, dried with Na₂SO₄, filtered off and evaporated to dryness. The residue was purified with flash column chromatography on silica eluting with a gradient formed from DCM, methanol and NEt₃. The product containing fractions were evaporated to yield 2.27 g (53%) of the title compound as light brown oil. MS m/e: 327.1 [M+H]⁺.

b) rac-[(3S,4R)-1-Benzyl-4-(4-chloro-phenyl)-pyrrolidin-3-yl]-cyclopropyl-carbamic acid 4-fluoro-phenyl ester

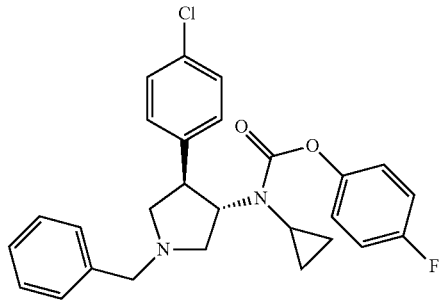 [SMILES: O=C(Oc1ccc(F)cc1)N(C1CC1)[C@@H]1CN(Cc2ccccc2)C[C@H]1c1ccc(Cl)cc1]

A mixture of 2.27 g (6.94 mmol) rac-[(3S,4R)-1-Benzyl-4-(4-chloro-phenyl)-pyrrolidin-3-yl]-cyclopropyl-amine, 987 mg (7.64 mmol) DIPEA, 8.48 mg (0.07 mmol) DMAP and 1.27 g (7.29 mmol) 4-fluorophenyl chloroformate in 40 mL DCM at 0° C. was stirred at room temperature over night and evaporated to dryness. the residue was purified by column chromatography on silica eluting with a gradient formed from TBME and heptane. The product containing fractions were evaporated to yield 1.64 g (51%) of the title compound as colorless viscous oil. MS m/e: 465.1 [M+H]⁺.

c) 4-{(3S,4R)-3-(4-Chloro-phenyl)-4-[cyclopropyl-(4-fluoro-phenoxycarbonyl)-amino]-pyrrolidine-1-carbonyl}-piperidine-1-carboxylic acid tert-butyl ester

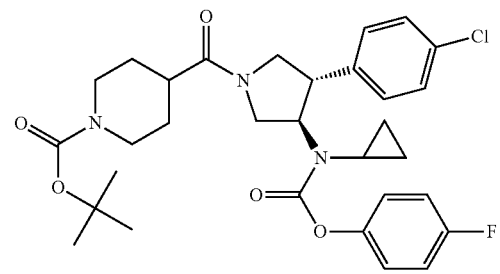 [SMILES: CC(C)(C)OC(=O)N1CCC(C(=O)N2C[C@H](c3ccc(Cl)cc3)[C@@H](N(C(=O)Oc3ccc(F)cc3)C3CC3)C2)CC1]

and

4-{(3R,4S)-3-(4-Chloro-phenyl)-4-[cyclopropyl-(4-fluoro-phenoxycarbonyl)-amino]-pyrrolidine-1-carbonyl}-piperidine-1-carboxylic acid tert-butyl ester

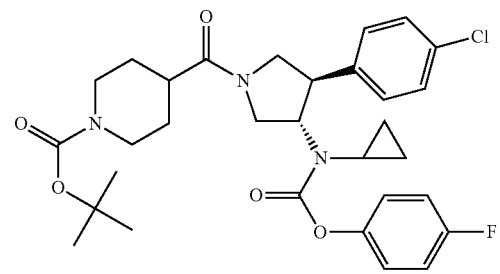 [SMILES: CC(C)(C)OC(=O)N1CCC(C(=O)N2C[C@@H](N(C(=O)Oc3ccc(F)cc3)C3CC3)[C@H](c3ccc(Cl)cc3)C2)CC1]

In analogy to the procedure described for the synthesis of rac-4-{(3R,4S)-3-(4-Chloro-phenyl)-4-[ethyl-(4-fluoro-phenoxycarbonyl)-amino]-pyrrolidine-1-carbonyl}-piperidine-1-carboxylic acid tert-butyl ester the title compounds were prepared from rac-[(3S,4R)-1-Benzyl-4-(4-chloro-phenyl)-pyrrolidin-3-yl]-cyclopropyl-carbamic acid 4-fluoro-phenyl ester by cleavage of the benzyl group and subsequent coupling with 1-(tert-butoxycarbonyl)piperidine-4-carboxylic acid. The resulting rac-4-{(3R,4S)-3-(4-Chloro-phenyl)-4-[cyclopropyl-(4-fluoro-phenoxycarbonyl)-amino]-pyrrolidine-1-carbonyl}-piperidine-1-carboxylic acid tert-butyl ester was subjected to separation by chiral HPLC on CHIRALPAK AD eluting with i-propanol/heptane. After evaporation of the product containing fractions 4-{(3S,4R)-3-(4-Chloro-phenyl)-4-[cyclopropyl-(4-fluoro-phenoxycarbonyl)-amino]-pyrrolidine-1-carbonyl}-piperidine-1-carboxylic acid tert-butyl ester was obtained as light brown foam. MS m/e: 586.3 [M+H]+. 4-{(3R,4S)-3-(4-Chloro-phenyl)-4-[cyclopropyl-(4-fluoro-phenoxycarbonyl)-amino]-pyrrolidine-1-carbonyl}-piperidine-1-carboxylic acid tert-butyl ester was obtained as yellow viscous oil. MS m/e: 586.3 [M+H]+.

d) [(3S,4R)-4-(4-Chloro-phenyl)-1-(piperidine-4-carbonyl)-pyrrolidin-3-yl]-cyclopropyl-carbamic acid 4-fluoro-phenyl ester

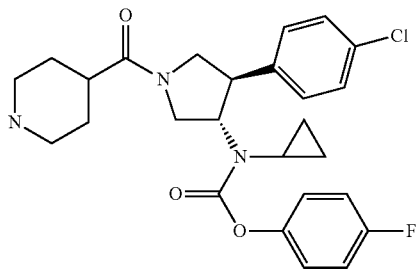 [SMILES: O=C(C1CCNCC1)N1C[C@@H](N(C(=O)Oc2ccc(F)cc2)C2CC2)[C@H](c2ccc(Cl)cc2)C1]

In analogy to the procedure described for the synthesis of [(3R,4S)-4-(4-Chloro-phenyl)-1-(piperidine-4-carbonyl)-pyrrolidin-3-yl]-ethyl-carbamic acid 4-fluoro-phenyl ester the title compound was prepared from 4-{(3R,4S)-3-(4-Chloro-phenyl)-4-[cyclopropyl-(4-fluoro-phenoxycarbonyl)-amino]-pyrrolidine-1-carbonyl}-piperidine-1-carboxylic acid tert-butyl ester through cleavage of the protecting group with TFA. The title compound was obtained as light yellow foam. MS m/e: 486.4 [M+H]+.

e) [(3S,4R)-4-(4-Chloro-phenyl)-1-(5'-cyano-3,4,5,6-tetrahydro-2H-[1,2']bipyridinyl-4-carbonyl)-pyrrolidin-3-yl]-cyclopropyl-carbamic acid 4-fluoro-phenyl ester In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3S,4R)-4-(4-Chloro-phenyl)-1-(piperidine-4-carbonyl)-pyrrolidin-3-yl]-cyclopropyl-carbamic acid 4-fluoro-phenyl ester and 6-bromonicotinonitrile as off-white solid. MS m/e: 588.2 [M+H]+.

Example 30

[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-cyclopropyl-carbamic acid 4-fluoro-phenyl ester

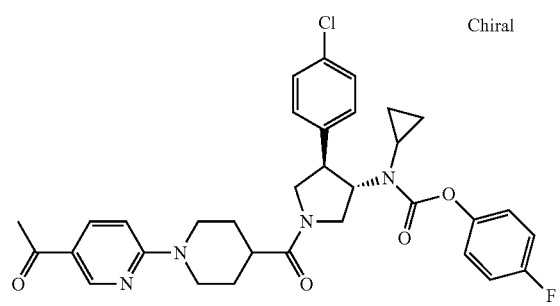 [SMILES: CC(=O)c1ccc(N2CCC(C(=O)N3C[C@@H](N(C(=O)Oc4ccc(F)cc4)C4CC4)[C@H](c4ccc(Cl)cc4)C3)CC2)nc1]

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3S,4R)-4-(4-Chloro-phenyl)-1-(piperidine-4-carbonyl)-pyrrolidin-3-yl]-cyclopropyl-carbamic acid 4-fluoro-phenyl ester and 1-(6-bromopyridin-3-yl)ethanone as off-white solid. MS m/e: 605.3 [M+H]+.

Example 31

[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-cyclopropyl-carbamic acid 4-fluoro-phenyl ester

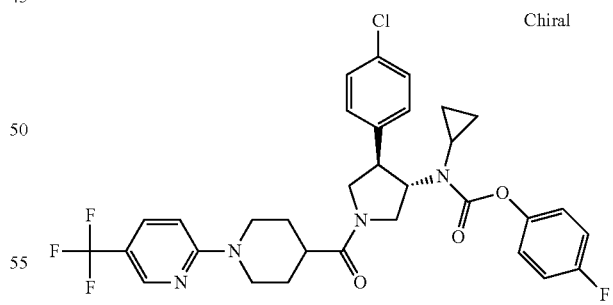

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3S,4R)-4-(4-Chloro-phenyl)-1-(piperidine-4-carbonyl)-pyrrolidin-3-yl]-cyclopropyl-carbamic acid 4-fluoro-phenyl ester and 2-bromo-5-(trifluoromethyl)pyridine as off-white solid. MS m/e: 631.4 [M+H]+.

Example 32

{(3S,4R)-4-(4-Chloro-phenyl)-1-[1-(6-cyano-pyridazin-3-yl)-piperidine-4-carbonyl]-pyrrolidin-3-yl}-cyclopropyl-carbamic acid 4-fluoro-phenyl ester

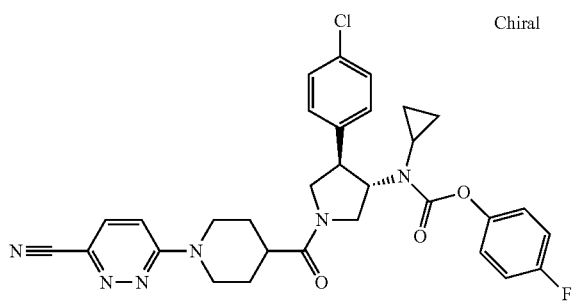 [SMILES: N#Cc1ccc(N2CCC(C(=O)N3C[C@@H](N(C(=O)Oc4ccc(F)cc4)C4CC4)[C@H](c4ccc(Cl)cc4)C3)CC2)nn1]

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3S,4R)-4-(4-Chloro-phenyl)-1-(piperidine-4-carbonyl)-pyrrolidin-3-yl]-cyclopropyl-carbamic acid 4-fluoro-phenyl ester and 6-chloropyridazine-3-carbonitrile as off-white solid. MS m/e: 589.3 [M+H]$^+$.

Example 33

{(3S,4R)-4-(4-Chloro-phenyl)-1-[1-(5-cyano-pyrazin-2-yl)-piperidine-4-carbonyl]-pyrrolidin-3-yl}-cyclopropyl-carbamic acid 4-fluoro-phenyl ester

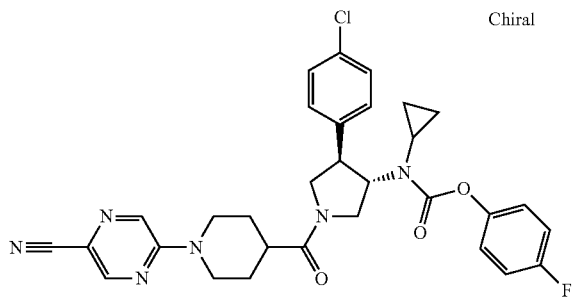 [SMILES: N#Cc1cnc(N2CCC(C(=O)N3C[C@@H](N(C(=O)Oc4ccc(F)cc4)C4CC4)[C@H](c4ccc(Cl)cc4)C3)CC2)cn1]

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3S,4R)-4-(4-Chloro-phenyl)-1-(piperidine-4-carbonyl)-pyrrolidin-3-yl]-cyclopropyl-carbamic acid 4-fluoro-phenyl ester and 5-chloropyrazine-2-carbonitrile as pink solid. MS m/e: 589.3 [M+H]$^+$.

Example 34

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-cyclopropyl-carbamic acid 4-fluoro-phenyl ester

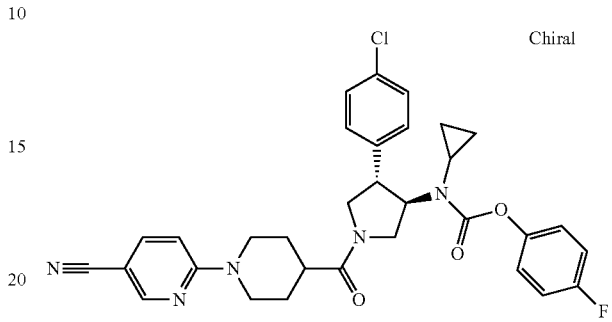

a) [(3R,4S)-4-(4-Chloro-phenyl)-1-(piperidine-4-carbonyl)-pyrrolidin-3-yl]-cyclopropyl-carbamic acid 4-fluoro-phenyl ester

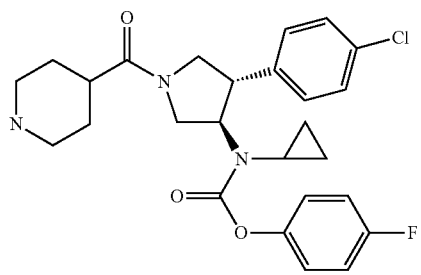 [SMILES: O=C(C1CCNCC1)N1C[C@H](c2ccc(Cl)cc2)[C@@H](N(C(=O)Oc2ccc(F)cc2)C2CC2)C1]

In analogy to the procedure described for the synthesis of [(3R,4S)-4-(4-Chloro-phenyl)-1-(piperidine-4-carbonyl)-pyrrolidin-3-yl]-ethyl-carbamic acid 4-fluoro-phenyl ester the title compound was prepared from 4-{(3S,4R)-3-(4-Chloro-phenyl)-4-[cyclopropyl-(4-fluoro-phenoxycarbonyl)-amino]-pyrrolidine-1-carbonyl}-piperidine-1-carboxylic acid tert-butyl ester through cleavage of the protecting group with TFA. The title compound was obtained as light yellow foam. MS m/e: 486.4 [M+H]$^+$.

b) [(3R,4S)-4-(4-Chloro-phenyl)-1-(5'-cyano-3,4,5,6-tetrahydro-2H-[1,2']bipyridinyl-4-carbonyl)-pyrrolidin-3-yl]-cyclopropyl-carbamic acid 4-fluoro-phenyl ester In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester the title compound was prepared from [(3R,4S)-4-(4-Chloro-phenyl)-1-(piperidine-4-carbonyl)-pyrrolidin-3-yl]-cyclopropyl-carbamic acid 4-fluoro-phenyl ester and 6-bromonicotinonitrile as off-white solid. MS m/e: 588.2 [M+H]$^+$.

Example 35

[(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester

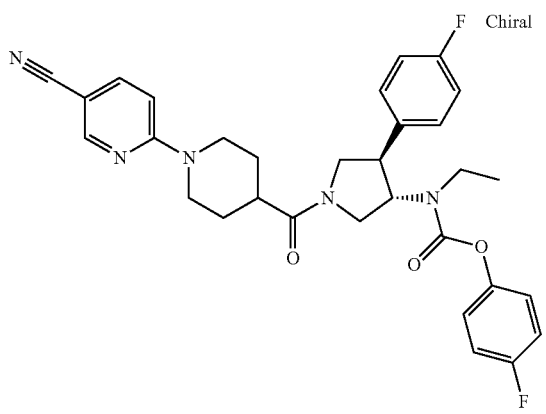 [SMILES: CCN(C(=O)Oc1ccc(F)cc1)[C@@H]1CN(C(=O)C2CCN(c3ccc(C#N)cn3)CC2)C[C@H]1c1ccc(F)cc1]

a) rac-(3S,4R)-1-Benzyl-4-(4-fluoro-phenyl)-pyrrolidin-3-ylamine

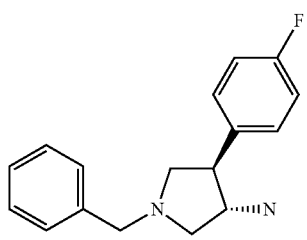 [SMILES: N[C@@H]1CN(Cc2ccccc2)C[C@H]1c1ccc(F)cc1]

In analogy to the procedure described for the synthesis of rac-(3S,4R)-1-Benzyl-4-(3,4-dichloro-phenyl)-pyrrolidin-3-ylamine (example 1, step a & b) the title compound was prepared from N-(methoxymethyl)-N-(phenylmethyl)-N-(trimethylsilyl)methylamine and 1-Fluoro-4-((E)-2-nitro-vinyl)-benzene subsequently reducing the NO₂-function with tin chloride. MS m/e: 271.4 [M+H]⁺.

b) rac-[(3S,4R)-1-Benzyl-4-(4-fluoro-phenyl)-pyrrolidin-3-yl]-ethyl-amine

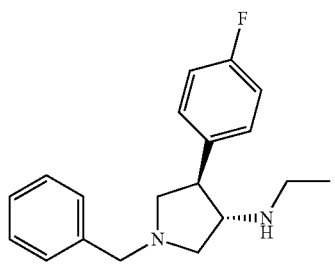 [SMILES: CCN[C@@H]1CN(Cc2ccccc2)C[C@H]1c1ccc(F)cc1]

A mixture of 38 g (141 mmol) rac-(3S,4R)-1-Benzyl-4-(4-fluoro-phenyl)-pyrrolidin-3-ylamine, 7.12 g (162 mmol) acetaldehyde, 12.1 mL acetic acid and 44.7 g (211 mmol) sodium triacetoxyborohydride in 400 mL THF was stirred for 3 h at 0° C. and then warmed to room temperature. Water, Na₂CO₃ aq. and ethyl acetate was added. The organic layer was washed with brine, dried with Na₂SO₄, filtered and evaporated to dryness. The residue was purified by column chromatography on silica eluting with a gradient formed from ethyl acetate, heptane and NEt₃. The product containing fractions were evaporated to yield 18.5 g (44%) of the title compound as brown oil. MS m/e: 299.4 [M+H]⁺.

c) rac-[(3S,4R)-1-Benzyl-4-(4-fluoro-phenyl)-pyrrolidin-3-yl]-ethyl-carbamic acid 4-fluoro-phenyl ester

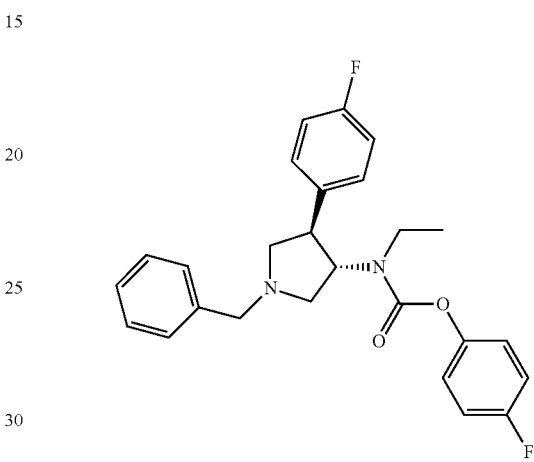

In analogy to the procedure described for the synthesis of rac-{(3S,4R)-4-(3,4-Dichloro-phenyl)-1-[1-(1-methyl cyclopropanecarbonyl)-piperidine-4-carbonyl]-pyrrolidin-3-yl}-ethyl-carbamic acid 4-fluoro-phenyl ester (example 1, step h) the title compound was prepared from rac-[(3S,4R)-1-Benzyl-4-(4-fluoro-phenyl)-pyrrolidin-3-yl]-ethyl-amine and 4-fluorophenyl chloroformate as light brown viscous oil. MS m/e: 437.3 [M+H]⁺.

d) [(3S,4R)-1-Benzyl-4-(4-fluoro-phenyl)-pyrrolidin-3-yl]-ethyl-carbamic acid 4-fluoro-phenyl ester

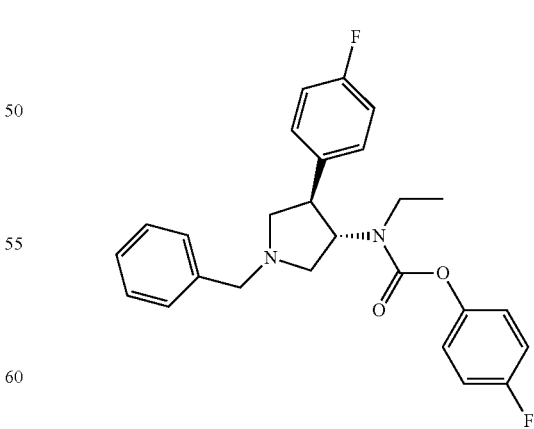

rac-[(3S,4R)-1-Benzyl-4-(4-fluoro-phenyl)-pyrrolidin-3-yl]-ethyl-carbamic acid 4-fluoro-phenyl ester was subjected to separation by column chromatography on Chiralpak AD eluting with hexane and i-propanol. The product containing fractions were evaporated to yield the title compound as light brown viscous oil. MS m/e: 437.3 [M+H]+.
and

[(3R,4S)-1-Benzyl-4-(4-fluoro-phenyl)-pyrrolidin-3-yl]-ethyl-carbamic acid 4-fluoro-phenyl ester

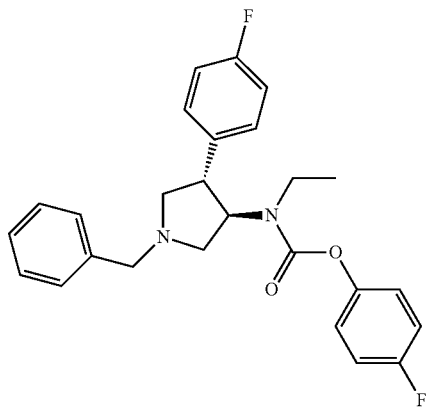 [SMILES: CCN(C(=O)Oc1ccc(F)cc1)[C@H]1CN(Cc2ccccc2)C[C@@H]1c1ccc(F)cc1]

rac-[(3S,4R)-1-Benzyl-4-(4-fluoro-phenyl)-pyrrolidin-3-yl]-ethyl-carbamic acid 4-fluoro-phenyl ester was subjected to separation by column chromatography on Chiralpak AD eluting with hexane and i-propanol. The product containing fractions were evaporated to yield the title compound as light brown viscous oil. MS m/e: 437.3 [M+H]+.

e) Ethyl-[(3S,4R)-4-(4-fluoro-phenyl)-pyrrolidin-3-yl]-carbamic acid 4-fluoro-phenyl ester

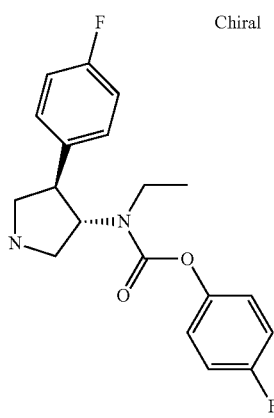

In analogy to the procedure described for the synthesis of rac-(3S,4R)-[4-(3,4-Dichloro-phenyl)-pyrrolidin-3-yl]-carbamic acid tert-butyl ester (example 1, step d) the title compound was prepared from [(3S,4R)-1-Benzyl-4-(4-fluoro-phenyl)-pyrrolidin-3-yl]-ethyl-carbamic acid 4-fluoro-phenyl ester through cleavage of the benzyl protecting group as brown foam. MS m/e: 347.1 [M+H]+.

f) [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester A mixture of 125 mg (0.36 mmol) ethyl-[(3S,4R)-4-(4-fluoro-phenyl)-pyrrolidin-3-yl]-carbamic acid 4-fluoro-phenyl ester, 137 mg (0.36 mmol) HATU, 63 uL (0.36 mmol) DIPEA and 69.4 mg (0.3 mmol) 5'-cyano-3,4,5,6-tetrahydro-2H-[1,2']bipyridinyl-4-carboxylic acid in 4 mL DMF was shaken for 2 h at room temperature. The mixture was subjected to purification by preparative HPLC on reversed phase eluting with a gradient formed from acetonitrile, water and NEt3. The product containing fractions were evaporated to yield 106 mg (63%) of the title compound as off-white solid. MS m/e: 560.2 [M+H]+.

Example 36

[(3S,4R)-1-(5'-Chloro-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester

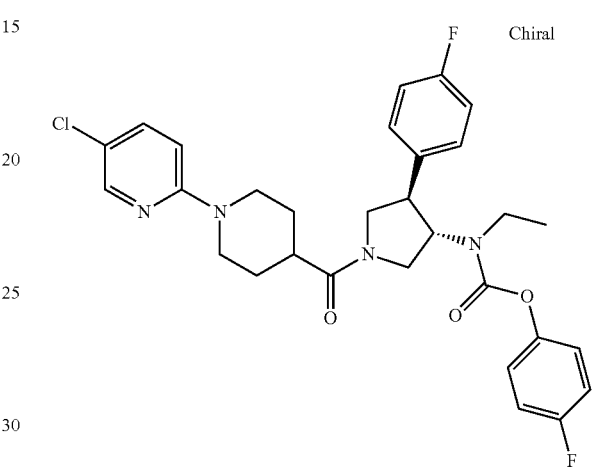

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35) the title compound was prepared from ethyl-[(3S,4R)-4-(4-fluoro-phenyl)-pyrrolidin-3-yl]-carbamic acid 4-fluoro-phenyl ester and 1-(5-chloropyridin-2-yl)piperidine-4-carboxylic acid. MS m/e: 569.3 [M+H]+.

Example 37

Ethyl-[(3S,4R)-4-(4-fluoro-phenyl)-1-(5'-methanesulfonyl-3,4,5,6-tetrahydro-2H-[1,2']bipyridinyl-4-carbonyl)-pyrrolidin-3-yl]-carbamic acid 4-fluoro-phenyl ester

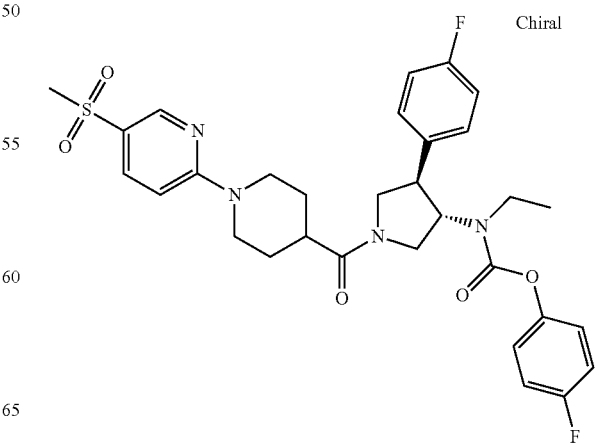

a) 4-[(3S,4R)-3-[Ethyl-(4-fluoro-phenoxycarbonyl)-amino]-4-(4-fluoro-phenyl)-pyrrolidine-1-carbonyl]-piperidine-1-carboxylic acid tert-butyl ester

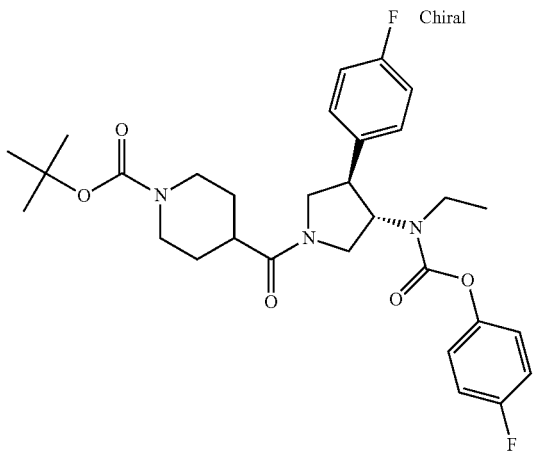 [SMILES: CCN(C(=O)Oc1ccc(F)cc1)[C@@H]1CN(C(=O)C2CCN(C(=O)OC(C)(C)C)CC2)C[C@H]1c1ccc(F)cc1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35) the title compound was prepared from ethyl-[(3S,4R)-4-(4-fluoro-phenyl)-pyrrolidin-3-yl]-carbamic acid 4-fluoro-phenyl ester and 1-(tert-butoxycarbonyl)piperidine-4-carboxylic acid. MS m/e: 558.4 [M+11]⁺.

b) Ethyl-[(3S,4R)-4-(4-fluoro-phenyl)-1-(piperidine-4-carbonyl)-pyrrolidin-3-yl]-carbamic acid 4-fluoro-phenyl ester

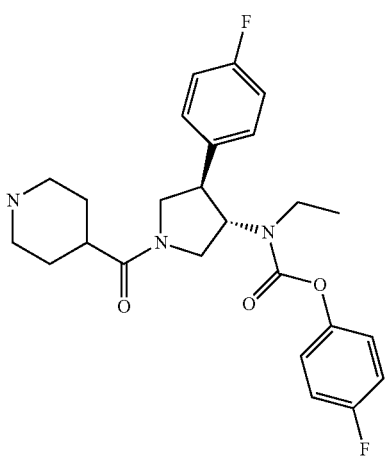 [SMILES: CCN(C(=O)Oc1ccc(F)cc1)[C@@H]1CN(C(=O)C2CCNCC2)C[C@H]1c1ccc(F)cc1]

In analogy to the procedure described for the synthesis of [(3R,4S)-4-(4-Chloro-phenyl)-1-(piperidine-4-carbonyl)-pyrrolidin-3-yl]-ethyl-carbamic acid 4-fluoro-phenyl ester (example 7, step f) the title compound was prepared from 4-[(3S,4R)-3-[Ethyl-(4-fluoro-phenoxycarbonyl)-amino]-4-(4-fluoro-phenyl)-pyrrolidine-1-carbonyl]-piperidine-1-carboxylic acid tert-butyl ester through cleavage of the Boc-group with TFA. MS m/e: 458.4 [M+H]⁺.

c) Ethyl-[(3S,4R)-4-(4-fluoro-phenyl)-1-(5'-methanesulfonyl-3,4,5,6-tetrahydro-2H-[1,2']bipyridinyl-4-carbonyl)-pyrrolidin-3-yl]-carbamic acid 4-fluoro-phenyl ester In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester (example 7, step g) the title compound was prepared from ethyl-[(3S,4R)-4-(4-fluoro-phenyl)-1-(piperidine-4-carbonyl)-pyrrolidin-3-yl]-carbamic acid 4-fluoro-phenyl ester and 2-bromo-5-(methylsulfonyl)pyridine. MS m/e: 613.2 [M+H]⁺.

Example 38

[(3S,4R)-1-(5'-Acetyl-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester

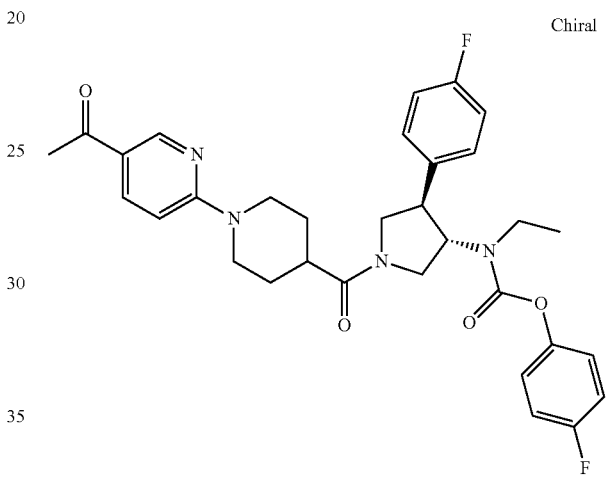

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester (example 7, step g) the title compound was prepared from ethyl-[(3S,4R)-4-(4-fluoro-phenyl)-1-(piperidine-4-carbonyl)-pyrrolidin-3-yl]-carbamic acid 4-fluoro-phenyl ester and 1-(6-bromopyridin-3-yl)ethanone. MS m/e: 577.3 [M+H]⁺.

Example 39

4-{(3R,4S)-3-(4-Chloro-3-fluoro-phenyl)-4-[ethyl-(4-fluoro-phenoxycarbonyl)-amino]-pyrrolidine-1-carbonyl}-piperidine-1-carboxylic acid tert-butyl ester

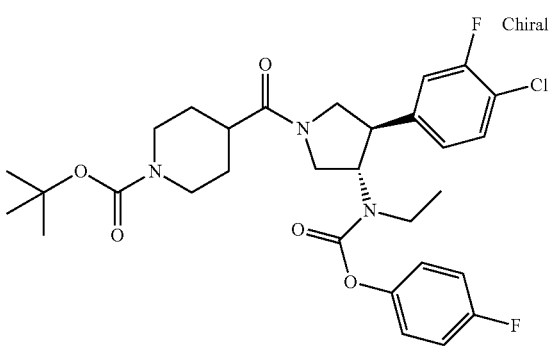 [SMILES: CCN(C(=O)Oc1ccc(F)cc1)[C@@H]1CN(C(=O)C2CCN(C(=O)OC(C)(C)C)CC2)C[C@H]1c1ccc(Cl)c(F)c1]

a) (4-Chloro-3-fluoro-phenyl)-propynoic acid ethyl ester

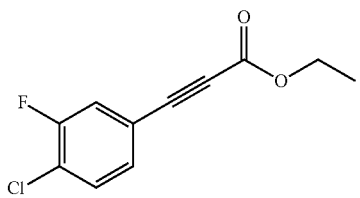

To a mixture of 4-chloro-3-fluoroiodobenzene (74.27 g, 284 mmol) and cesium carbonate (185.0 g, 568 mmol) in tetrahydrofuran (730 mL) was added under an argon atmosphere cuprous iodide (2.16 g, 11.4 mmol) and bis(triphenylphosphine)palladium (II) chloride (3.98 g, 5.7 mmol). Ethyl propiolate (57.0 g, 575 mmol) was added dropwise over a period of 20 min. The resulting dark brown suspension was stirred for 38 h at 35° C., then filtrated over Hyflo® and the residue was washed with tetrahydrofuran (285 ml). The filtrate was evaporated and purification of the residue by chromatography (SiO$_2$, heptane: ethyl acetate=90:10) afforded the title compound (57.1 g, 89%) as a yellow liquid. MS m/e: 226.0 [M]$^+$.

b) 1-Benzyl-4-(4-chloro-3-fluoro-phenyl)-2,5-dihydro-1H-pyrrole-3-carboxylic acid

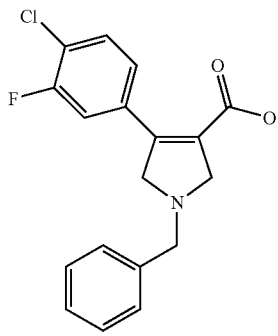

To a solution of (4-chloro-3-fluoro-phenyl)-propynoic acid ethyl ester (57.08 g, 252 mmol) in dichloromethane (240 mL) was added trifluoroacetic acid (1.9 mL, 25.2 mmol). The reaction mixture was cooled with a water bath at ambient temperature and a solution of N-(methoxymethyl)-N-(trimethylsilylmethyl)benzylamine (93.43 g, 378 mmol) in dichloromethane (185 mL) was added dropwise over a period of 3 h. After stirring for 20 h at ambient temperature further N-(methoxymethyl)-N-(trimethylsilylmethyl)benzylamine (15.6 g, 63.0 mmol) in dichloromethane (30 mL) was added and stirring was continued for another 4 h. The solvent was removed and the residue was dissolved in dioxane (540 mL). After addition of water (270 mL) and aqueous sodium hydroxide (32%, 64.8 ml, 700 mmol), it was stirred for 44 h at ambient temperature. After concentration the resulting residue was diluted with water (225 mL) and extracted with tert-butylmethylether (225 mL). The organic layer was washed with water (225 mL) and the aqueous layer was cooled to 5° C. and set to pH=1.5 with aqueous hydrogen chloride (25%, 112 mL). After stirring for 1 h at 5° C., the resulting solid was filtered and washed with water (795 mL) and ethanol (225 mL). Drying gave a light yellow solid which was stirred with ethanol (4 L) for 1 h at 85° C. The resulting suspension was filtered and the filtrate was concentrated. Trituration with tert-butylmethylether (2 L) afforded the title compound (62.34 g, 67%) as an off-white solid. MS m/e: 330.1 [M−H]$^-$.

c) (3R,4R)-1-Benzyl-4-(4-chloro-3-fluoro-phenyl)-pyrrolidine-3-carboxylic acid

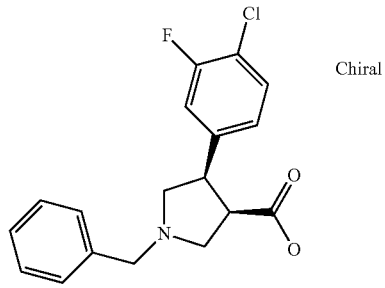 [SMILES: O=C(O)[C@H]1CN(Cc2ccccc2)C[C@H]1c1ccc(Cl)c(F)c1]

An autoclave was charged under argon in a glove box (O$_2$ content<2 ppm) with 1-Benzyl-4-(4-chloro-3-fluoro-phenyl)-2,5-dihydro-1H-pyrrole-3-carboxylic acid (1.00 g, 3.01 mmol), [Ru(OAc)$_2$((S)-2-furyl-MeOBIPHEP)] (9.18 mg, 0.012 mmol) (2-furyl-MeOBIPHEP=(6,6'-dimethoxybiphenyl-2,2'-diyl)bis(di-2-furylphosphine) and methanol (30 mL). The asymmetric hydrogenation was run for 20 h at 30° C. under 40 bar of hydrogen. After the pressure was released, the grey suspension was evaporated to dryness to yield the crude title compound. MS m/e: 332.1 [M−H].

d) (3S,4R)-1-Benzyl-4-(4-chloro-3-fluoro-phenyl)-pyrrolidine-3-carboxylic acid

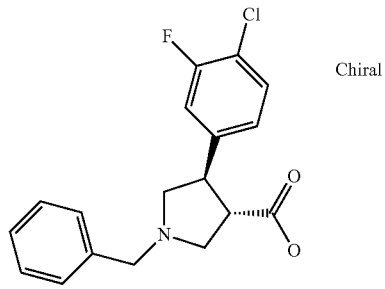 [SMILES: O=C(O)[C@@H]1CN(Cc2ccccc2)C[C@H]1c1ccc(Cl)c(F)c1]

A mixture of 48.8 g (146 mmol) (3R,4R)-1-Benzyl-4-(4-chloro-3-fluoro-phenyl)-pyrrolidine-3-carboxylic acid and 15.6 mL sulfuric acid in 400 mL methanol was heated to reflux for 21 h and evaporated. the residue was diluted with ice-water and extracted with ethyl acetate. the combined organic layers were washed with brine, dried with Na$_2$SO$_4$, filtered and evaporated to dryness. The residue was purified by column chromatography on silica eluting with ethyl acetate and heptane. The intermediate was dissolved in 500 mL methanol and 4.06 mL sodium methoxide (5.4N in methanol) was added and stirred at room temperature overnight. Another 31.3 mL sodium methoxide (5.4N in methanol) was added and stirred for 1 h at room temperature. Water was added and the mixture was stirred for 2 h at room temperature. After evaporation of methanol, water was added and the pH was adjusted to 6-7 with acetic acid. The product precipitated and the mixture was decanted. The organic layer from the extraction with THF and ethyl acetate was washed with brine, dried with Na$_2$SO$_4$, filtered and evaporated to dryness. The residue was washed with hexane and diethyl ether and filtered to yield after drying 44 g (49%) of the title compound as colorless solid. MS m/e: 334.3 [M+H]$^+$.

e) [(3S,4R)-1-Benzyl-4-(4-chloro-3-fluoro-phenyl)-pyrrolidin-3-yl]-carbamic acid tert-butyl ester

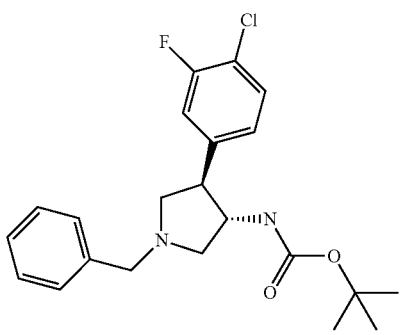 [SMILES: CC(C)(C)OC(=O)N[C@@H]1CN(Cc2ccccc2)C[C@H]1c1ccc(Cl)c(F)c1]

A mixture of 44 g (132 mmol) (3S,4R)-1-Benzyl-4-(4-chloro-3-fluoro-phenyl)-pyrrolidine-3-carboxylic acid, 25.3 mL (145 mmol) DIPEA and 45.3 g (165 mmol) diphenylphosphoryl azide in 600 mL tert.-butanol was heated to reflux for 16 h. After cooling to room temperature the mixture was evaporated to dryness. The residue was adsorbed on isolute HM-N and purified by column chromatography on silica eluting with a gradient formed from heptane and ethyl acetate. The product containing fraction were evaporated to yield 25 g (47%) of the title compound as light brown solid. MS m/e: 405.4 [M+H]$^+$.

f) (3S,4R)-1-Benzyl-4-(4-chloro-3-fluoro-phenyl)-pyrrolidin-3-ylamine

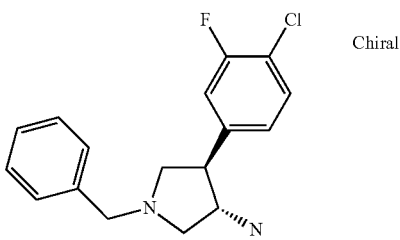 [SMILES: N[C@@H]1CN(Cc2ccccc2)C[C@H]1c1ccc(Cl)c(F)c1]

In analogy to the procedure described for the synthesis of rac-(3S,4R)-[3-Amino-4-(3,4-dichloro-phenyl)-pyrrolidin-1-yl]-[1-(1-methyl-cyclopropanecarbonyl)-piperidin-4-yl]-methanone (example 1, step f) the title compound was prepared from [(3S,4R)-1-Benzyl-4-(4-chloro-3-fluoro-phenyl)-pyrrolidin-3-yl]-carbamic acid tert-butyl ester through cleavage of the Boc-group with TFA. MS m/e: 305.2 [M+H]$^+$.

g) [(3S,4R)-1-Benzyl-4-(4-chloro-3-fluoro-phenyl)-pyrrolidin-3-yl]-ethyl-carbamic acid 4-fluoro-phenyl ester

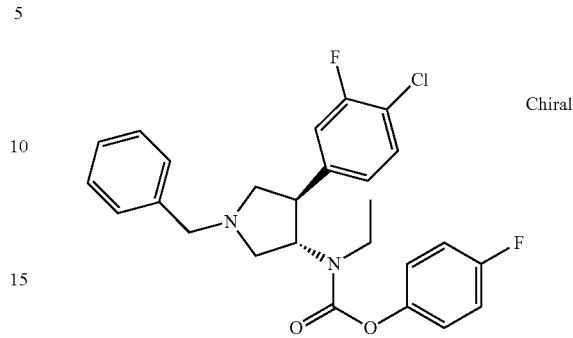

In analogy to the procedure described for the synthesis of rac-{(3S,4R)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester (example 1, step g & h) the title compound was prepared from (3S,4R)-1-Benzyl-4-(4-chloro-3-fluoro-phenyl)-pyrrolidin-3-ylamine through reductive amination with acetaldehyde followed by reaction with 4-fluorophenyl chloroformate to yield the title compound as light brown oil. MS m/e: 471.2 [M+H]$^+$.

h) [(3S,4R)-4-(4-Chloro-3-fluoro-phenyl)-pyrrolidin-3-yl]-ethyl-carbamic acid 4-fluoro-phenyl ester

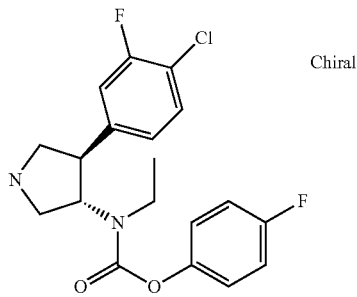 [SMILES: CCN(C(=O)Oc1ccc(F)cc1)[C@@H]1CNC[C@H]1c1ccc(Cl)c(F)c1]

In analogy to the procedure described for the synthesis of rac-(3S,4R)-[4-(3,4-Dichloro-phenyl)-pyrrolidin-3-yl]-carbamic acid tert-butyl ester (example 1, step d) the title compound was prepared from [(3S,4R)-1-Benzyl-4-(4-chloro-3-fluoro-phenyl)-pyrrolidin-3-yl]-ethyl-carbamic acid 4-fluoro-phenyl ester through cleavage of the benzyl-group as brown foam which was used in the consecutive step without further purification. MS m/e: 381.3 [M+H]$^+$.

i) 4-{(3R,4S)-3-(4-Chloro-3-fluoro-phenyl)-4-[ethyl-(4-fluoro-phenoxycarbonyl)-amino]-pyrrolidine-1-carbonyl}-piperidine-1-carboxylic acid tert-butyl ester In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35) the title compound was prepared from [(3S,4R)-4-(4-Chloro-3-fluoro-phenyl)-pyrrolidin-3-yl]-ethyl-carbamic acid 4-fluoro-phenyl ester and 1-(tert-butoxycarbonyl)piperidine-4-carboxylic acid. MS m/e: 592.4 [M+H]$^+$.

Example 40

[(3S,4R)-4-(4-Chloro-3-fluoro-phenyl)-1-(5'-cyano-3,4,5,6-tetrahydro-2H-[1,2']bipyridinyl-4-carbonyl)-pyrrolidin-3-yl]-ethyl-carbamic acid 4-fluoro-phenyl ester

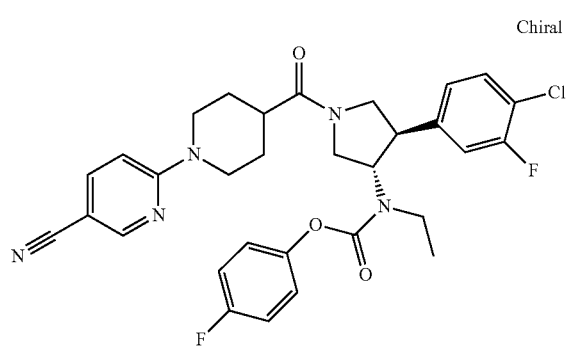 [SMILES: CCN(C(=O)Oc1ccc(F)cc1)[C@@H]1CN(C(=O)C2CCN(c3ccc(C#N)cn3)CC2)C[C@H]1c1ccc(Cl)c(F)c1]

a) [(3S,4R)-4-(4-Chloro-3-fluoro-phenyl)-1-(piperidine-4-carbonyl)-pyrrolidin-3-yl]-ethyl-carbamic acid 4-fluoro-phenyl ester

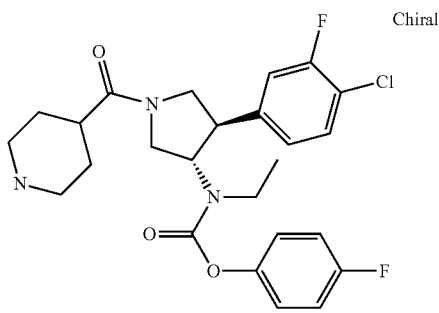 [SMILES: CCN(C(=O)Oc1ccc(F)cc1)[C@@H]1CN(C(=O)C2CCNCC2)C[C@H]1c1ccc(Cl)c(F)c1]

In analogy to the procedure described for the synthesis of [(3R,4S)-4-(4-Chloro-phenyl)-1-(piperidine-4-carbonyl)-pyrrolidin-3-yl]-ethyl-carbamic acid 4-fluoro-phenyl ester (example 7, step f) the title compound was prepared from 4-{(3R,4S)-3-(4-Chloro-3-fluoro-phenyl)-4-[ethyl-(4-fluoro-phenoxycarbonyl)-amino]-pyrrolidine-1-carbonyl}-piperidine-1-carboxylic acid tert-butyl ester through cleavage of the Boc-group with TFA. MS m/e: 492.2 [M+H]$^+$.

b) [(3S,4R)-4-(4-Chloro-3-fluoro-phenyl)-1-(5'-cyano-3,4,5,6-tetrahydro-2H-[1,2']bipyridinyl-4-carbonyl)-pyrrolidin-3-yl]-ethyl-carbamic acid 4-fluoro-phenyl ester In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester (example 7, step g) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 1-(5-cyanopyridin-2-yl)piperidine-4-carboxylic acid. MS m/e: 594.3 [M+H]$^+$.

Example 41

[(3S,4R)-4-(4-Chloro-3-fluoro-phenyl)-1-(5'-chloro-3,4,5,6-tetrahydro-2H-[1,2']bipyridinyl-4-carbonyl)-pyrrolidin-3-yl]-ethyl-carbamic acid 4-fluoro-phenyl ester

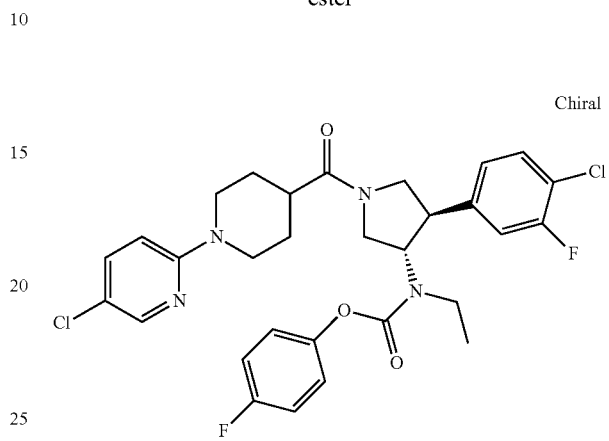

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 1-(5-chloropyridin-2-yl)piperidine-4-carboxylic acid. MS m/e: 603.2 [M+H]$^+$.

Example 42

[(3S,4R)-4-(4-Chloro-3-fluoro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester

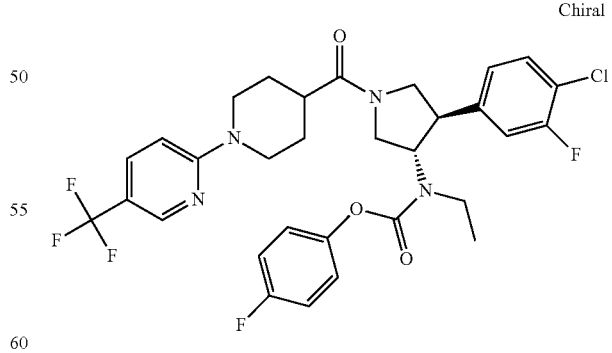

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]- ethyl-carbamic acid 4-fluoro-phenyl ester and 1-(5-(trifluoromethyl)pyridin-2-yl)piperidine-4-carboxylic acid. MS m/e: 637.3 [M+H]⁺.

Example 43

[(3S,4R)-4-(4-Chloro-3-fluoro-phenyl)-1-(6'-cyano-3,4,5,6-tetrahydro-2H-[1,3']bipyridinyl-4-carbonyl)-pyrrolidin-3-yl]-ethyl-carbamic acid 4-fluoro-phenyl ester

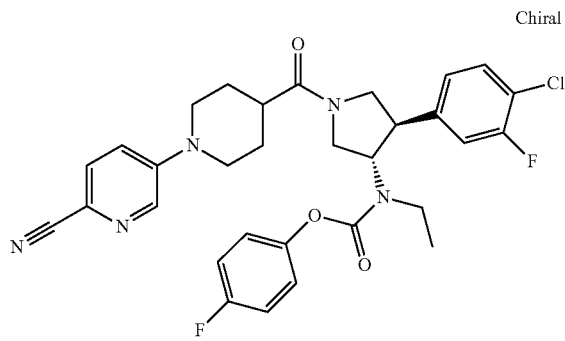 [SMILES: CCN(C(=O)Oc1ccc(F)cc1)[C@@H]1CN(C(=O)C2CCN(c3ccc(C#N)nc3)CC2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 1-(5-(trifluoromethyl)pyridin-2-yl)piperidine-4-carboxylic acid. MS m/e: 594.3 [M+H]⁺.

Example 44

{(3S,4R)-4-(4-Chloro-3-fluoro-phenyl)-1-[1-(1-methyl-cyclopropanecarbonyl)-piperidine-4-carbonyl]-pyrrolidin-3-yl}-ethyl-carbamic acid 4-fluoro-phenyl ester

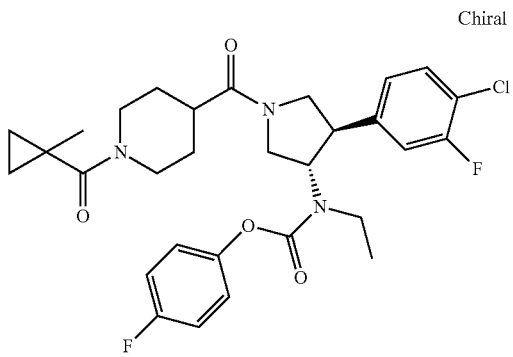 [SMILES: CCN(C(=O)Oc1ccc(F)cc1)[C@@H]1CN(C(=O)C2CCN(C(=O)C3(C)CC3)CC2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 1-(1-methyl-cyclopropanecarbonyl)piperidine-4-carboxylic acid. MS m/e: 574.5 [M+H]⁺.

Example 45

[(3S,4R)-4-(4-Chloro-3-fluoro-phenyl)-1-(4'-cyano-3,4,5,6-tetrahydro-2H-[1,2']bipyridinyl-4-carbonyl)-pyrrolidin-3-yl]-ethyl-carbamic acid 4-fluoro-phenyl ester

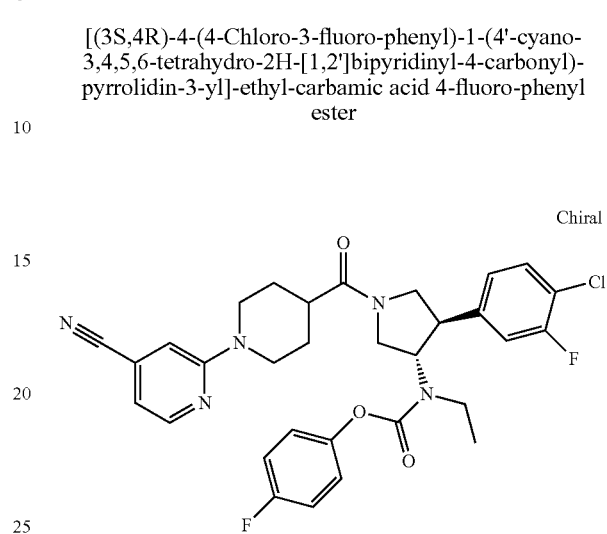

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 1-(4-cyanopyridin-2-yl)piperidine-4-carboxylic acid. MS m/e: 594.3 [M+H]⁺.

Example 46

[(3S,4R)-4-(4-Chloro-3-fluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester

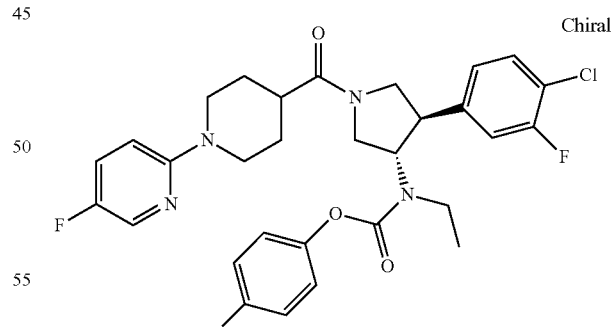

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 1-(5-fluoropyridin-2-yl)piperidine-4-carboxylic acid. MS m/e: 587.2 [M+H]⁺.

Example 47

[(3S,4R)-4-(4-Chloro-3-fluoro-phenyl)-1-(5'-methyl-3,4,5,6-tetrahydro-2H-[1,2']bipyridinyl-4-carbonyl)-pyrrolidin-3-yl]-ethyl-carbamic acid 4-fluoro-phenyl ester

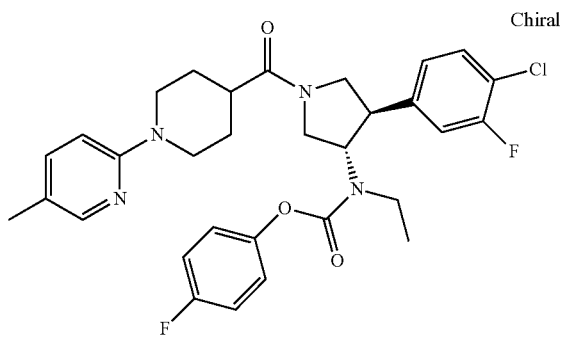 [SMILES: CCN(C(=O)Oc1ccc(F)cc1)[C@@H]1CN(C(=O)C2CCN(c3ccc(C)cn3)CC2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 1-(5-methylpyridin-2-yl)piperidine-4-carboxylic acid. MS m/e: 583.2 [M+H]$^+$.

Example 48

[(3S,4R)-1-(5'-Cyano-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester

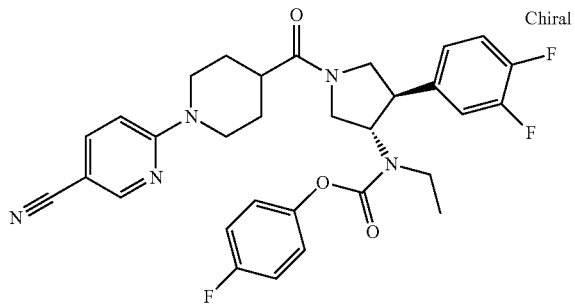 [SMILES: CCN(C(=O)Oc1ccc(F)cc1)[C@@H]1CN(C(=O)C2CCN(c3ccc(C#N)cn3)CC2)C[C@H]1c1ccc(F)c(F)c1]

a) (3,4-Difluoro-phenyl)-propynoic acid ethyl ester

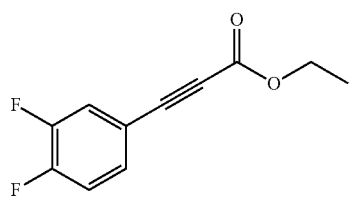

In analogy to the procedure described for the synthesis of (4-Chloro-3-fluoro-phenyl)-propynoic acid ethyl ester (example 39, step a) the title compound was prepared from 3,4-difluoroiodobenzene and ethyl propionate as yellow liquid. MS m/e: 210 [M+H]$^+$.

b) 1-Benzyl-4-(3,4-difluoro-phenyl)-2,5-dihydro-1H-pyrrole-3-carboxylic acid

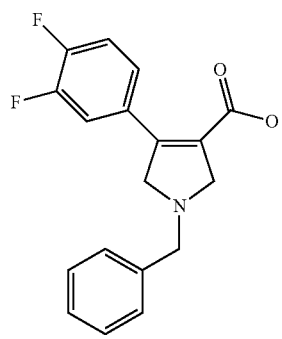 [SMILES: O=C(O)C1=C(c2ccc(F)c(F)c2)CN(Cc2ccccc2)C1]

In analogy to the procedure described for the synthesis of 1-Benzyl-4-(4-chloro-3-fluoro-phenyl)-2,5-dihydro-1H-pyrrole-3-carboxylic acid (example 39, step b) the title compound was prepared from (3,4-Difluoro-phenyl)-propynoic acid ethyl ester and N-(methoxymethyl)-N-(trimethylsilylmethyl)benzylamine. MS m/e: 314.1 [M−H]$^-$.

c) (3R,4R)-1-Benzyl-4-(3,4-difluoro-phenyl)-pyrrolidine-3-carboxylic acid

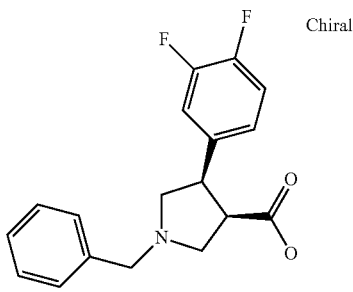 [SMILES: O=C(O)[C@H]1CN(Cc2ccccc2)C[C@H]1c1ccc(F)c(F)c1]

In analogy to the procedure described for the synthesis of (3R,4R)-1-Benzyl-4-(4-chloro-3-fluoro-phenyl)-pyrrolidine-3-carboxylic acid (example 39, step c) the title compound was prepared from 1-Benzyl-4-(3,4-difluoro-phenyl)-2,5-dihydro-1H-pyrrole-3-carboxylic acid through asymmetric hydrogenation.

d) (3S,4R)-1-Benzyl-4-(3,4-difluoro-phenyl)-pyrrolidine-3-carboxylic acid

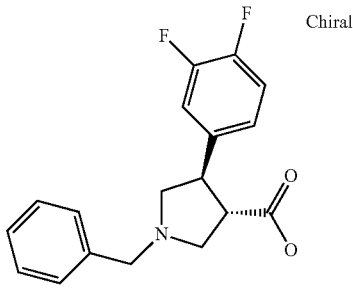 [SMILES: O=C(O)[C@@H]1CN(Cc2ccccc2)C[C@H]1c1ccc(F)c(F)c1]

In analogy to the procedure described for the synthesis of (3S,4R)-1-Benzyl-4-(4-chloro-3-fluoro-phenyl)-pyrrolidine-3-carboxylic acid (example 39, step d) the title compound was prepared from (3R,4R)-1-Benzyl-4-(3,4-difluoro-phenyl)-pyrrolidine-3-carboxylic acid as white solid. MS m/e: 318.1 [M+H]$^+$.

e) [(3S,4R)-1-Benzyl-4-(3,4-difluoro-phenyl)-pyrrolidin-3-yl]-carbamic acid tert-butyl ester

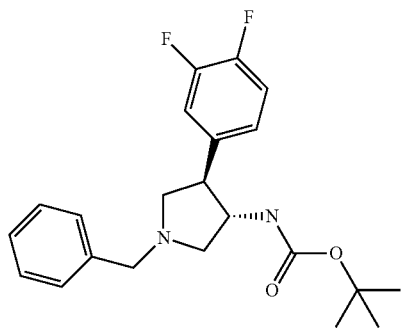 [SMILES: CC(C)(C)OC(=O)N[C@@H]1CN(Cc2ccccc2)C[C@H]1c1ccc(F)c(F)c1]

In analogy to the procedure described for the synthesis of [(3S,4R)-1-Benzyl-4-(4-chloro-3-fluoro-phenyl)-pyrrolidin-3-yl]-carbamic acid tert-butyl ester (example 39, step e) the title compound was prepared from (3S,4R)-1-Benzyl-4-(3,4-difluoro-phenyl)-pyrrolidine-3-carboxylic acid as off-white solid. MS m/e: 389.3 [M+H]$^+$.

f) (3S,4R)-1-Benzyl-4-(3,4-difluoro-phenyl)-pyrrolidin-3-ylamine

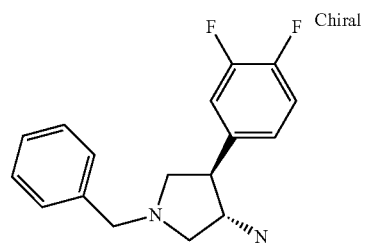 [SMILES: N[C@@H]1CN(Cc2ccccc2)C[C@H]1c1ccc(F)c(F)c1]

In analogy to the procedure described for the synthesis of (3S,4R)-1-Benzyl-4-(4-chloro-3-fluoro-phenyl)-pyrrolidin-3-ylamine (example 39, step f) the title compound was prepared from [(3S,4R)-1-Benzyl-4-(3,4-difluoro-phenyl)-pyrrolidin-3-yl]-carbamic acid tert-butyl ester as brown oil. MS m/e: 289.2 [M+H]$^+$.

g) [(3S,4R)-1-Benzyl-4-(3,4-difluoro-phenyl)-pyrrolidin-3-yl]-ethyl-carbamic acid 4-fluoro-phenyl ester

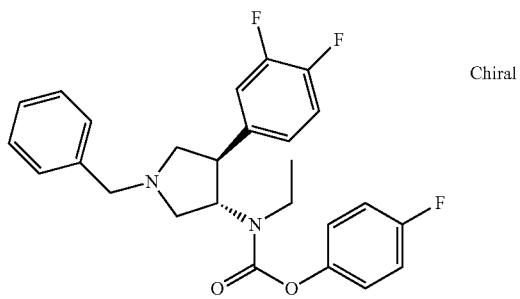 [SMILES: CCN(C(=O)Oc1ccc(F)cc1)[C@@H]1CN(Cc2ccccc2)C[C@H]1c1ccc(F)c(F)c1]

In analogy to the procedure described for the synthesis of [(3S,4R)-1-Benzyl-4-(4-chloro-3-fluoro-phenyl)-pyrrolidin-3-yl]-ethyl-carbamic acid 4-fluoro-phenyl ester (example 39, step g) the title compound was prepared from (3S,4R)-1-Benzyl-4-(3,4-difluoro-phenyl)-pyrrolidin-3-ylamine as light yellow oil. MS m/e: 455.3 [M+H]$^+$.

h) [(3S,4R)-4-(3,4-Difluoro-phenyl)-pyrrolidin-3-yl]-ethyl-carbamic acid 4-fluoro-phenyl ester

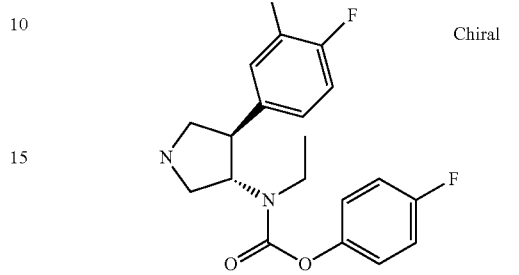

In analogy to the procedure described for the synthesis of [(3S,4R)-4-(4-Chloro-3-fluoro-phenyl)-pyrrolidin-3-yl]-ethyl-carbamic acid 4-fluoro-phenyl ester (example 39, step h) the title compound was prepared from [(3S,4R)-1-Benzyl-4-(3,4-difluoro-phenyl)-pyrrolidin-3-yl]-ethyl-carbamic acid 4-fluoro-phenyl ester as brown foam. MS m/e: 365.3 [M+H]$^+$.

i) [(3S,4R)-1-(5'-Cyano-3,4,5,6-tetrahydro-2H-[1,2'] bipyridinyl-4-carbonyl)-4-(3,4-difluoro-phenyl)-pyrrolidin-3-yl]-ethyl-carbamic acid 4-fluoro-phenyl ester In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35) the title compound was prepared from [(3S,4R)-4-(3,4-Difluoro-phenyl)-pyrrolidin-3-yl]-ethyl-carbamic acid 4-fluoro-phenyl ester and 1-(5-cyanopyridin-2-yl)piperidine-4-carboxylic acid. MS m/e: 578.3 [M+H]$^+$.

Example 49

[(3S,4R)-1-(5'-Chloro-3,4,5,6-tetrahydro-2H-[1,2'] bipyridinyl-4-carbonyl)-4-(3,4-difluoro-phenyl)-pyrrolidin-3-yl]-ethyl-carbamic acid 4-fluoro-phenyl ester

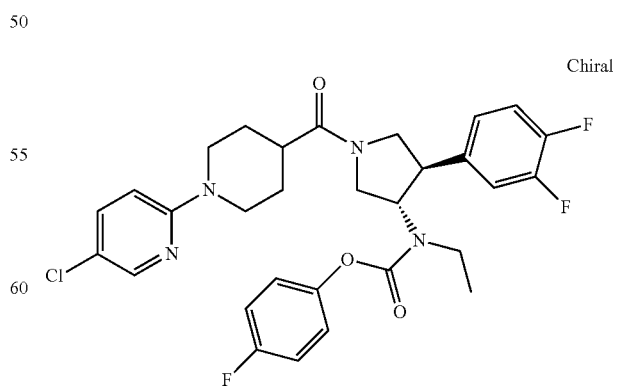

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethylcarbamic acid 4-fluoro-phenyl ester (example 35) the title compound was prepared from [(3S,4R)-4-(3,4-Difluoro-phenyl)-pyrrolidin-3-yl]-ethyl-carbamic acid 4-fluoro-phenyl ester and 1-(5-chloropyridin-2-yl)piperidine-4-carboxylic acid. MS m/e: 587.2 [M+H]⁺.

Example 50

[(3S,4R)-4-(3,4-Difluoro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester

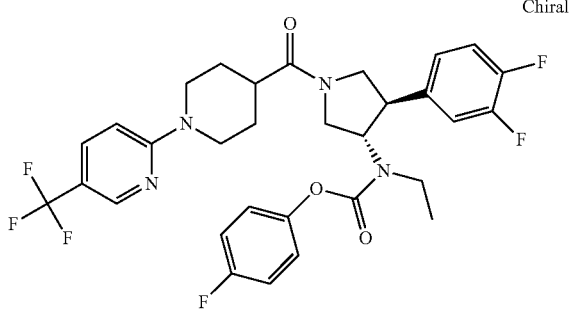 [SMILES: CCN(C(=O)Oc1ccc(F)cc1)[C@@H]1CN(C(=O)C2CCN(c3ccc(C(F)(F)F)cn3)CC2)C[C@H]1c1ccc(F)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Difluoro-phenyl)-pyrrolidin-3-yl]-ethyl-carbamic acid 4-fluoro-phenyl ester and 1-(5-(trifluoromethyl)pyridin-2-yl)piperidine-4-carboxylic acid. MS m/e: 612.4 [M+H]⁺.

Example 51

[(3S,4R)-1-(6'-Cyano-3,4,5,6-tetrahydro-2H-[1,3']bipyridinyl-4-carbonyl)-4-(3,4-difluoro-phenyl)-pyrrolidin-3-yl]-ethyl-carbamic acid 4-fluoro-phenyl ester

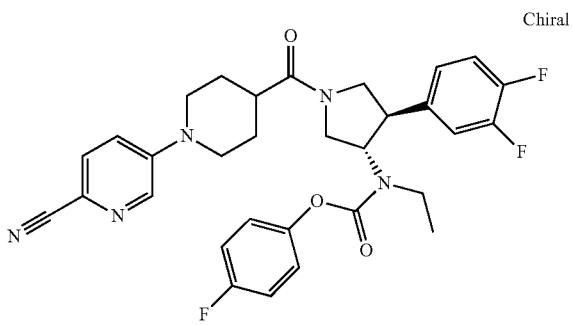 [SMILES: CCN(C(=O)Oc1ccc(F)cc1)[C@@H]1CN(C(=O)C2CCN(c3ccc(C#N)nc3)CC2)C[C@H]1c1ccc(F)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Difluoro-phenyl)-pyrrolidin-3-yl]-ethyl-carbamic acid 4-fluoro-phenyl ester and 1-(6-cyanopyridin-3-yl)piperidine-4-carboxylic acid. MS m/e: 578.3 [M+H]⁺.

Example 52

{(3S,4R)-4-(3,4-Difluoro-phenyl)-1-[1-(1-methyl-cyclopropanecarbonyl)-piperidine-4-carbonyl]-pyrrolidin-3-yl}-ethyl-carbamic acid 4-fluoro-phenyl ester

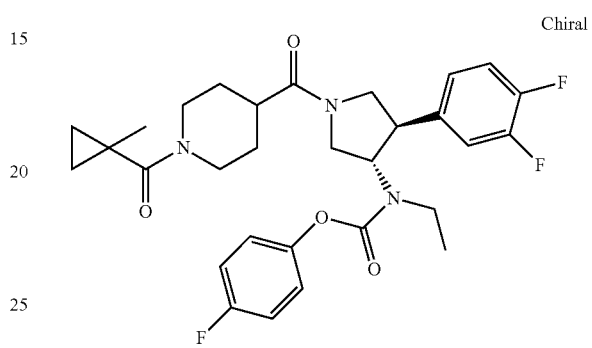

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Difluoro-phenyl)-pyrrolidin-3-yl]-ethyl-carbamic acid 4-fluoro-phenyl ester and 1-(1-methylcyclopropanecarbonyl)piperidine-4-carboxylic acid. MS m/e: 558.3 [M+H]⁺.

Example 53

[(3S,4R)-1-(4'-Cyano-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester

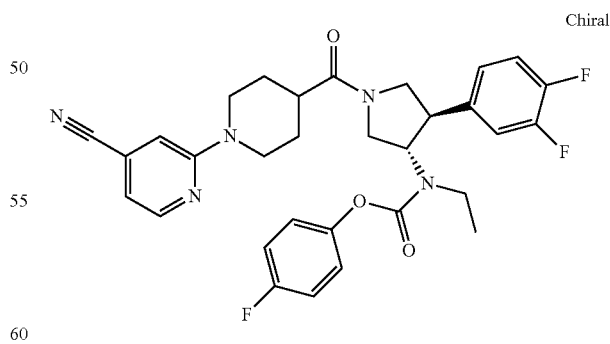

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Difluoro-phenyl)-pyrrolidin-3-yl]-ethyl-carbamic acid 4-fluoro-phenyl ester and 1-(4-cyanopyridin-2-yl)piperidine-4-carboxylic acid. MS m/e: 578.4 [M+H]⁺.

Example 54

[(3S,4R)-4-(3,4-Difluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester

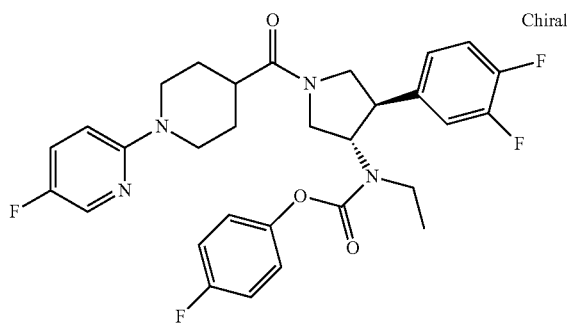 [SMILES: CCN(C(=O)Oc1ccc(F)cc1)[C@@H]1CN(C(=O)C2CCN(c3ccc(F)cn3)CC2)C[C@H]1c1ccc(F)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Difluoro-phenyl)-pyrrolidin-3-yl]ethyl-carbamic acid 4-fluoro-phenyl ester and 1-(5-fluoropyridin-2-yl)piperidine-4-carboxylic acid. MS m/e: 571.4 [M+H]⁺.

Example 55

[(3S,4R)-4-(3,4-Difluoro-phenyl)-1-(5'-methyl-3,4,5,6-tetrahydro-2H-[1,2']bipyridinyl-4-carbonyl)-pyrrolidin-3-yl]-ethyl-carbamic acid 4-fluoro-phenyl ester

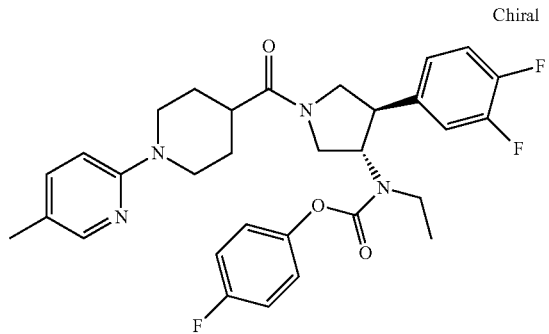 [SMILES: CCN(C(=O)Oc1ccc(F)cc1)[C@@H]1CN(C(=O)C2CCN(c3ccc(C)cn3)CC2)C[C@H]1c1ccc(F)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Difluoro-phenyl)-pyrrolidin-3-yl]-ethyl-carbamic acid 4-fluoro-phenyl ester and 1-(5-methylpyridin-2-yl)piperidine-4-carboxylic acid. MS m/e: 567.4 [M+H]⁺.

Example 56

[(3S,4R)-4-(4-Chloro-3-fluoro-phenyl)-1-(piperidine-4-carbonyl)-pyrrolidin-3-yl]-ethyl-carbamic acid 4-fluoro-phenyl ester

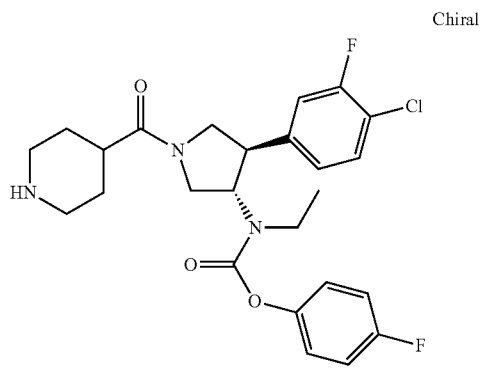 [SMILES: CCN(C(=O)Oc1ccc(F)cc1)[C@@H]1CN(C(=O)C2CCNCC2)C[C@H]1c1ccc(Cl)c(F)c1]

a) 4-{(3R,4S)-3-(4-Chloro-3-fluoro-phenyl)-4-[ethyl-(4-fluoro-phenoxycarbonyl)-amino]-pyrrolidine-1-carbonyl}-piperidine-1-carboxylic acid tert-butyl ester In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Difluoro-phenyl)-pyrrolidin-3-yl]-ethyl-carbamic acid 4-fluoro-phenyl ester and 1-(tert-butoxycarbonyl)piperidine-4-carboxylic acid. MS m/e: 592.4 [M+11]⁺.

b) [(3S,4R)-4-(4-Chloro-3-fluoro-phenyl)-1-(piperidine-4-carbonyl)-pyrrolidin-3-yl]-ethyl-carbamic acid 4-fluoro-phenyl ester In analogy to the procedure described for the synthesis of [(3R,4S)-4-(4-Chloro-phenyl)-1-(piperidine-4-carbonyl)-pyrrolidin-3-yl]-ethyl-carbamic acid 4-fluoro-phenyl ester (example 7, step f) the title compound was prepared from 4-{(3R,4S)-3-(4-Chloro-3-fluoro-phenyl)-4-[ethyl-(4-fluoro-phenoxycarbonyl)-amino]-pyrrolidine-1-carbonyl}-piperidine-1-carboxylic acid tert-butyl ester through cleavage of the Boc-group with TFA. MS m/e: 492.2 [M+H]⁺.

Example 57

{(3S,4R)-4-(4-Chloro-3-fluoro-phenyl)-1-[1-(6-cyano-pyridazin-3-yl)-piperidine-4-carbonyl]-pyrrolidin-3-yl}-ethyl-carbamic acid 4-fluoro-phenyl ester

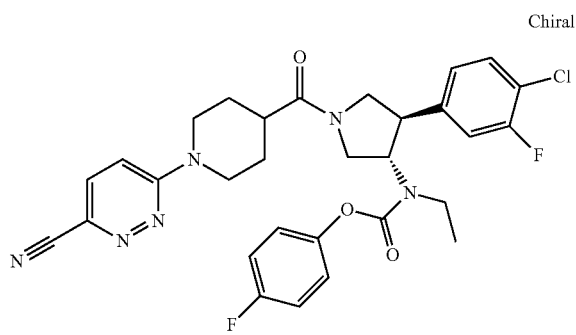 [SMILES: CCN(C(=O)Oc1ccc(F)cc1)[C@@H]1CN(C(=O)C2CCN(c3ccc(C#N)nn3)CC2)C[C@H]1c1ccc(Cl)c(F)c1]

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester (example 7, step g) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 6-chloropyridazine-3-carbonitrile in acetonitrile as off-white solid after purification over silica. MS m/e: 595.4 [M+H]$^+$.

Example 58

[(3S,4R)-1-[1-(6-Cyano-pyridazin-3-yl)-piperidine-4-carbonyl]-4-(3,4-difluoro-phenyl)-pyrrolidin-3-yl]-ethyl-carbamic acid 4-fluoro-phenyl ester

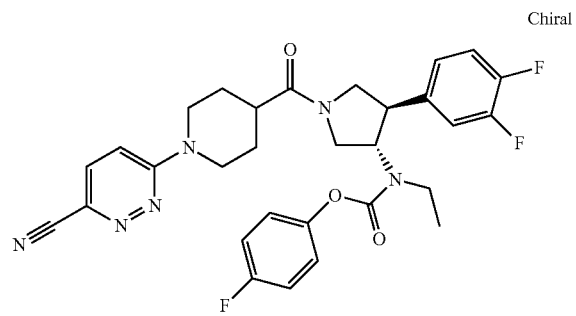 [SMILES: CCN(C(=O)Oc1ccc(F)cc1)[C@@H]1CN(C(=O)C2CCN(c3ccc(C#N)nn3)CC2)C[C@H]1c1ccc(F)c(F)c1]

a) 4-{(3R,4S)-3-(3,4-Difluoro-phenyl)-4-[ethyl-(4-fluoro-phenoxycarbonyl)-amino]-pyrrolidine-1-carbonyl}-piperidine-1-carboxylic acid tert-butyl ester

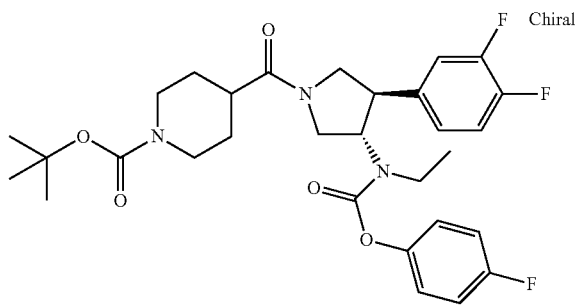 [SMILES: CCN(C(=O)Oc1ccc(F)cc1)[C@@H]1CN(C(=O)C2CCN(C(=O)OC(C)(C)C)CC2)C[C@H]1c1ccc(F)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Difluoro-phenyl)-pyrrolidin-3-yl]-ethyl-carbamic acid 4-fluoro-phenyl ester and 1-(tert-butoxycarbonyl)piperidine-4-carboxylic acid. MS m/e: 576.3 [M+H]$^+$.

b) [(3S,4R)-4-(3,4-Difluoro-phenyl)-1-(piperidine-4-carbonyl)-pyrrolidin-3-yl]-ethyl-carbamic acid 4-fluoro-phenyl ester

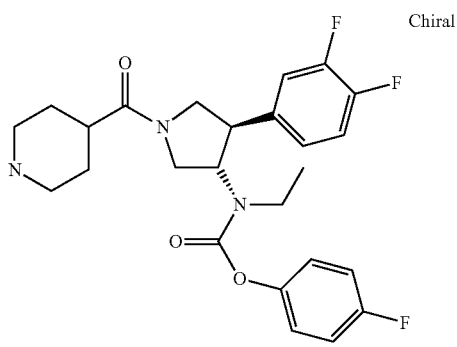

In analogy to the procedure described for the synthesis of [(3R,4S)-4-(4-Chloro-phenyl)-1-(piperidine-4-carbonyl)-pyrrolidin-3-yl]-ethyl-carbamic acid 4-fluoro-phenyl ester (example 7, step f) the title compound was prepared from 4-{(3R,4S)-3-(3,4-Difluoro-phenyl)-4-[ethyl-(4-fluoro-phenoxycarbonyl)-amino]-pyrrolidine-1-carbonyl}-piperidine-1-carboxylic acid tert-butyl ester through cleavage of the Boc-group with TFA. MS m/e: 492.2 [M+H]$^+$.

c) [(3S,4R)-1-[1-(6-Cyano-pyridazin-3-yl)-piperidine-4-carbonyl]-4-(3,4-difluoro-phenyl)-pyrrolidin-3-yl]-ethyl-carbamic acid 4-fluoro-phenyl ester In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester (example 7, step g) the title compound was prepared from [(3S,4R)-4-(3,4-Difluoro-phenyl)-1-(piperidine-4-carbonyl)-pyrrolidin-3-yl]-ethyl-carbamic acid 4-fluoro-phenyl ester and 6-chloropyridazine-3-carbonitrile in acetonitrile as off-white solid after purification over silica. MS m/e: 579.4 [M+H]$^+$.

Example 59

[(3S,4R)-1-(5'-Acetyl-3,4,5,6-tetrahydro-2H-[1,2']bipyridinyl-4-carbonyl)-4-(4-chloro-3-fluoro-phenyl)-pyrrolidin-3-yl]-ethyl-carbamic acid 4-fluoro-phenyl ester

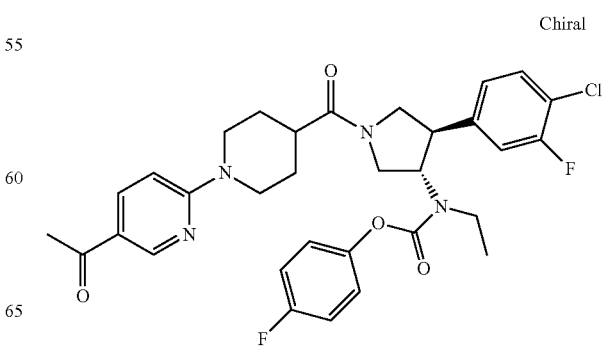

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester (example 7, step g) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 1-(6-bromopyridin-3-yl)ethanone in acetonitrile as off-white solid after purification over silica. MS m/e: 611.3 [M+H]⁺.

Example 60

[(3S,4R)-1-(5'-Acetyl-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester

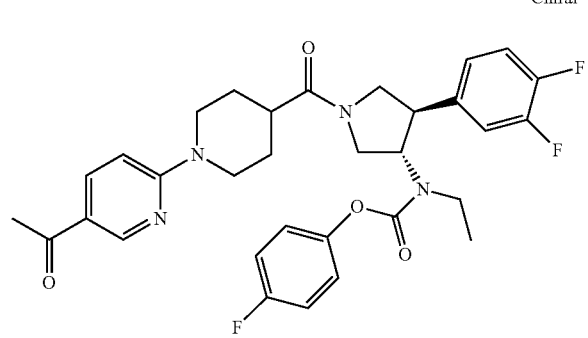

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester (example 7, step g) the title compound was prepared from [(3S,4R)-4-(3,4-Difluoro-phenyl)-1-(piperidine-4-carbonyl)-pyrrolidin-3-yl]-ethyl-carbamic acid 4-fluoro-phenyl ester and 1-(6-bromopyridin-3-yl)ethanone in acetonitrile as off-white solid after purification over silica. MS m/e: 595.4 [M+H]⁺.

Example 61

{(3S,4R)-4-(4-Chloro-3-fluoro-phenyl)-1-[1-(5-cyano-pyrazin-2-yl)-piperidine-4-carbonyl]-pyrrolidin-3-yl}-ethyl-carbamic acid 4-fluoro-phenyl ester

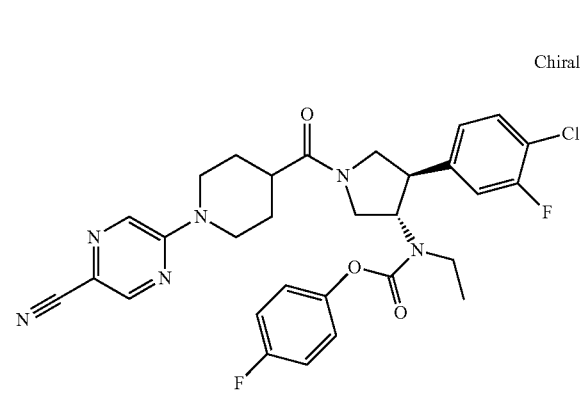 [SMILES: CCN(C(=O)Oc1ccc(F)cc1)[C@@H]1CN(C(=O)C2CCN(c3cnc(C#N)cn3)CC2)C[C@H]1c1ccc(Cl)c(F)c1]

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester (example 7, step g) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 5-bromopyrazine-2-carbonitrile in acetonitrile as dark brown solid after purification over silica. MS m/e: 595.4 [M+H]⁺.

Example 62

[(3S,4R)-1-[1-(5-Cyano-pyrazin-2-yl)-piperidine-4-carbonyl]-4-(3,4-difluoro-phenyl)-pyrrolidin-3-yl]-ethyl-carbamic acid 4-fluoro-phenyl ester

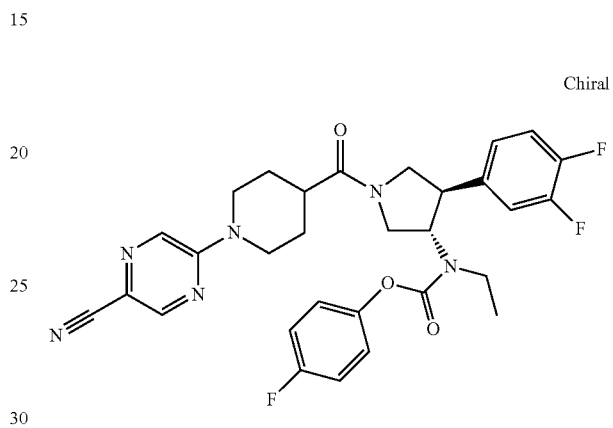

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester (example 7, step g) the title compound was prepared from [(3S,4R)-4-(3,4-Difluoro-phenyl)-1-(piperidine-4-carbonyl)-pyrrolidin-3-yl]-ethyl-carbamic acid 4-fluoro-phenyl ester and 5-bromopyrazine-2-carbonitrile in acetonitrile as dark brown solid after purification over silica. MS m/e: 579.4 [M+H]⁺.

Example 63

[(3S,4R)-4-(4-Chloro-3-fluoro-phenyl)-1-(5'-methanesulfonyl-3,4,5,6-tetrahydro-2H-[1,2']bipyridinyl-4-carbonyl)-pyrrolidin-3-yl]-ethyl-carbamic acid 4-fluoro-phenyl ester

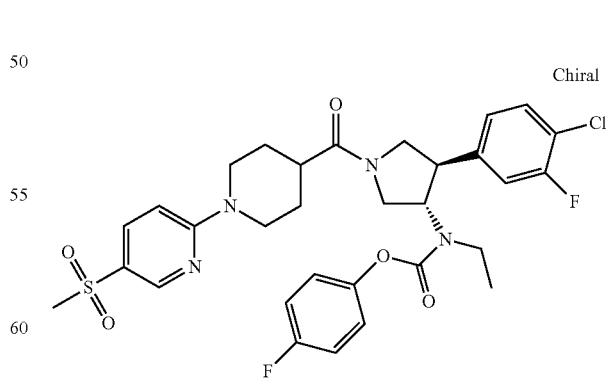

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester (example 7, step g) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 2-bromo-5-(methylsulfonyl)pyridine in acetonitrile as off-white solid after purification over silica. MS m/e: 647.4 [M+H]⁺.

Example 64

[(3S,4R)-4-(3,4-Difluoro-phenyl)-1-(5'-methane-sulfonyl-3,4,5,6-tetrahydro-2H-[1,2']bipyridinyl-4-carbonyl)-pyrrolidin-3-yl]-ethyl-carbamic acid 4-fluoro-phenyl ester

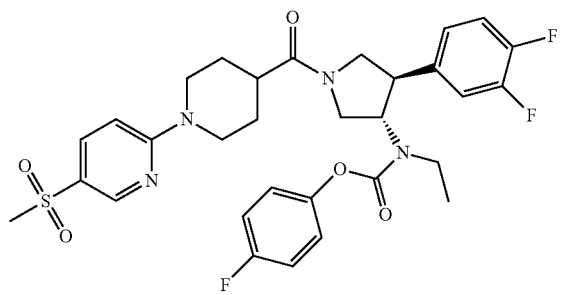

In analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester (example 7, step g) the title compound was prepared from [(3S,4R)-4-(3,4-Difluoro-phenyl)-1-(piperidine-4-carbonyl)-pyrrolidin-3-yl]-ethyl-carbamic acid 4-fluoro-phenyl ester and 2-bromo-5-(methylsulfonyl)pyridine in acetonitrile as dark brown solid after purification over silica. MS m/e: 631.4 [M+H]⁺.

Example 65

{(3S,4R)-4-(4-Chloro-3-fluoro-phenyl)-1-[1-(3-methyl-oxetane-3-carbonyl)-piperidine-4-carbonyl]-pyrrolidin-3-yl}-ethyl-carbamic acid 4-fluoro-phenyl ester

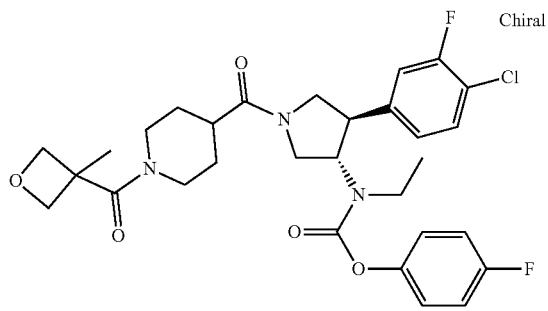 [SMILES: CCN(C(=O)Oc1ccc(F)cc1)[C@@H]1CN(C(=O)C2CCN(C(=O)C3(C)COC3)CC2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 3-methyloxetane-3-carboxylic acid. MS m/e: 590.3 [M+H]⁺.

Example 66

{(3S,4R)-4-(4-Chloro-3-fluoro-phenyl)-1-[1-(3,3-difluoro-cyclobutanecarbonyl)-piperidine-4-carbonyl]-pyrrolidin-3-yl}-ethyl-carbamic acid 4-fluoro-phenyl ester

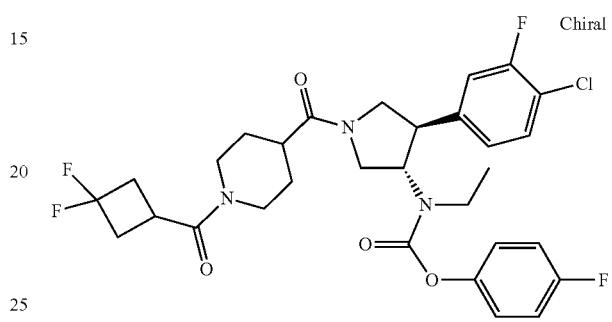

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 3,3-difluoro-cyclobutanecarboxylic acid. MS m/e: 610.2 [M+H]⁺.

Example 67

[(3S,4R)-4-(4-Chloro-3-fluoro-phenyl)-1-(1-cyclobutanecarbonyl-piperidine-4-carbonyl)-pyrrolidin-3-yl]-ethyl-carbamic acid 4-fluoro-phenyl ester

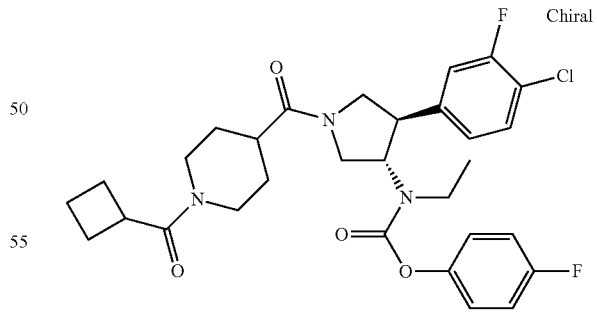

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and cyclobutanecarboxylic acid. MS m/e: 574.5 [M+H]⁺.

Example 68

{(3S,4R)-4-(4-Chloro-3-fluoro-phenyl)-1-[1-(1-trifluoromethyl-cyclobutanecarbonyl)-piperidine-4-carbonyl]-pyrrolidin-3-yl}-ethyl-carbamic acid 4-fluoro-phenyl ester

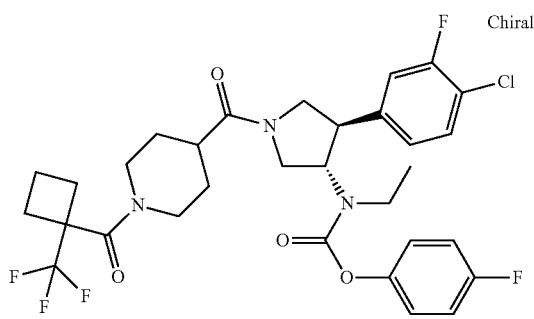 [SMILES: CCN(C(=O)Oc1ccc(F)cc1)[C@@H]1CN(C(=O)C2CCN(C(=O)C3(C(F)(F)F)CCC3)CC2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 1-(trifluoromethyl)cyclobutanecarboxylic acid. MS m/e: 642.3 [M+H]$^+$.

Example 69

{(3S,4R)-4-(4-Chloro-3-fluoro-phenyl)-1-[1-(3-fluoro-cyclobutanecarbonyl)-piperidine-4-carbonyl]-pyrrolidin-3-yl}-ethyl-carbamic acid 4-fluoro-phenyl ester

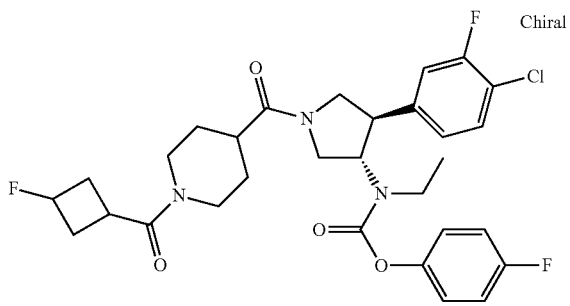 [SMILES: CCN(C(=O)Oc1ccc(F)cc1)[C@@H]1CN(C(=O)C2CCN(C(=O)C3CC(F)C3)CC2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 3-fluorocyclobutanecarboxylic acid. MS m/e: 592.4 [M+H]$^+$.

Example 70

{(3S,4R)-4-(4-Chloro-3-fluoro-phenyl)-1-[1-(2,2-difluoro-cyclopropanecarbonyl)-piperidine-4-carbonyl]-pyrrolidin-3-yl}-ethyl-carbamic acid 4-fluoro-phenyl ester

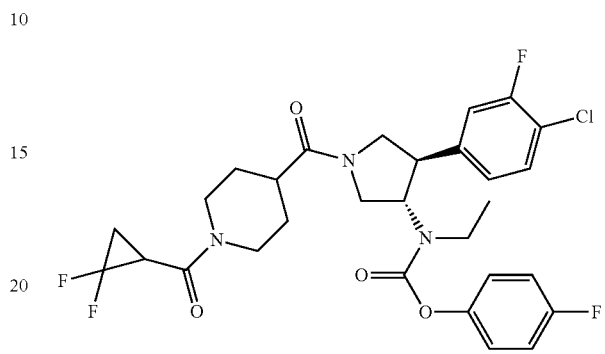

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 2,2-difluoro-cyclopropanecarboxylic acid. MS m/e: 596.3 [M+H]$^+$.

Example 71

{(3S,4R)-4-(4-Chloro-3-fluoro-phenyl)-1-[1-(1-trifluoromethyl-cyclopropanecarbonyl)-piperidine-4-carbonyl]-pyrrolidin-3-yl}-ethyl-carbamic acid 4-fluoro-phenyl ester

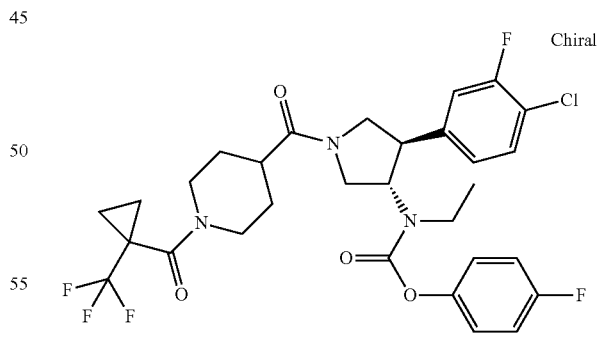

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 1-(trifluoromethyl)cyclopropanecarboxylic acid. MS m/e: 628.4 [M+H]$^+$.

Example 72

{(3S,4R)-4-(4-Chloro-3-fluoro-phenyl)-1-[1-(1-cyano-cyclopropanecarbonyl)-piperidine-4-carbonyl]-pyrrolidin-3-yl}-ethyl-carbamic acid 4-fluoro-phenyl ester

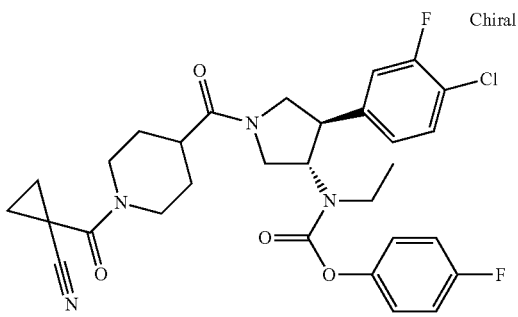 [SMILES: CCN(C(=O)Oc1ccc(F)cc1)[C@@H]1CN(C(=O)C2CCN(C(=O)C3(C#N)CC3)CC2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 1-cyanocyclopropanecarboxylic acid. MS m/e: 585.3 [M+H]+.

Example 73

{(3S,4R)-4-(4-Chloro-3-fluoro-phenyl)-1-[1-(2,2-dimethyl-tetrahydro-pyran-4-carbonyl)-piperidine-4-carbonyl]-pyrrolidin-3-yl}-ethyl-carbamic acid 4-fluoro-phenyl ester

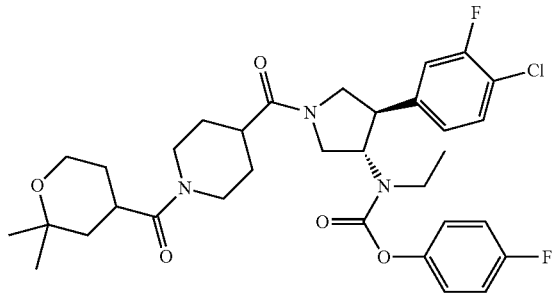 [SMILES: CCN(C(=O)Oc1ccc(F)cc1)[C@@H]1CN(C(=O)C2CCN(C(=O)C3CCOC(C)(C)C3)CC2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 2,2-dimethyltetrahydro-2H-pyran-4-carboxylic acid. MS m/e: 632.5 [M+H]+.

Example 74

{(3S,4R)-4-(4-Chloro-3-fluoro-phenyl)-1-[1-(5-trifluoromethyl-pyridine-2-carbonyl)-piperidine-4-carbonyl]-pyrrolidin-3-yl}-ethyl-carbamic acid 4-fluoro-phenyl ester

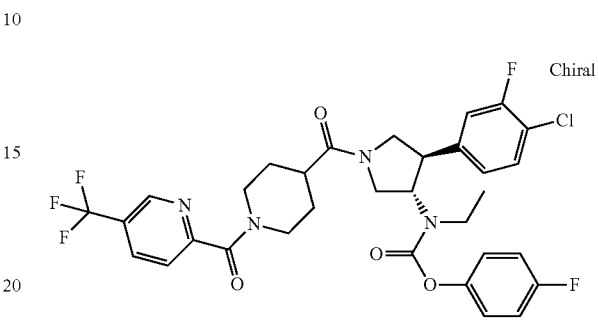

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 5-(trifluoromethyl)picolinic acid. MS m/e: 665.2 [M+H]+.

Example 75

{(3S,4R)-4-(4-Chloro-3-fluoro-phenyl)-1-[1-(5-fluoro-pyridine-2-carbonyl)-piperidine-4-carbonyl]-pyrrolidin-3-yl}-ethyl-carbamic acid 4-fluoro-phenyl ester

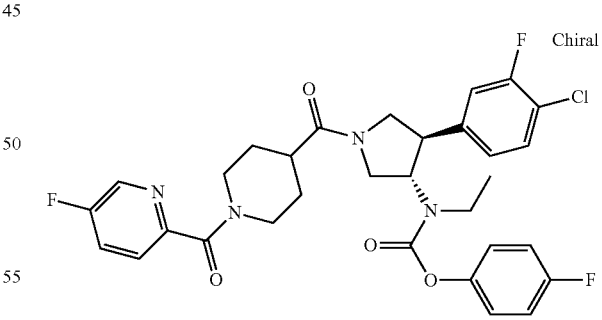

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 5-fluoropicolinic acid. MS m/e: 615.2 [M+H]+.

Example 76

{(3S,4R)-4-(4-Chloro-3-fluoro-phenyl)-1-[1-(4-cyano-benzoyl)-piperidine-4-carbonyl]-pyrrolidin-3-yl}-ethyl-carbamic acid 4-fluoro-phenyl ester

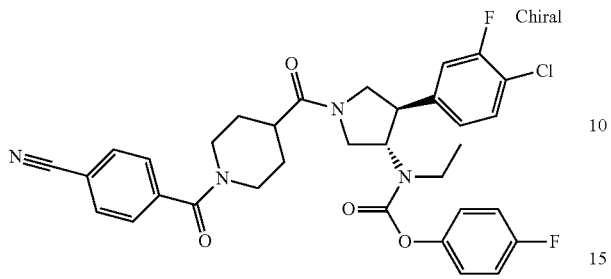

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 4-cyanobenzoic acid. MS m/e: 621.4 [M+H]$^+$.

Example 77

{(3S,4R)-4-(4-Chloro-3-fluoro-phenyl)-1-[1-(4-fluoro-benzoyl)-piperidine-4-carbonyl]-pyrrolidin-3-yl}-ethyl-carbamic acid 4-fluoro-phenyl ester

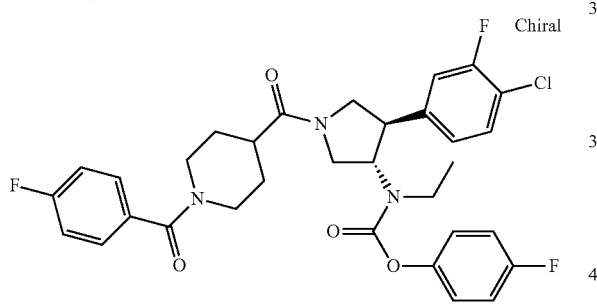

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 4-fluorobenzoic acid. MS m/e: 614.2 [M+H]$^+$.

Example 78

{(3S,4R)-4-(4-Chloro-3-fluoro-phenyl)-1-[1-(5-trifluoromethyl-pyrazine-2-carbonyl)-piperidine-4-carbonyl]-pyrrolidin-3-yl}-ethyl-carbamic acid 4-fluoro-phenyl ester

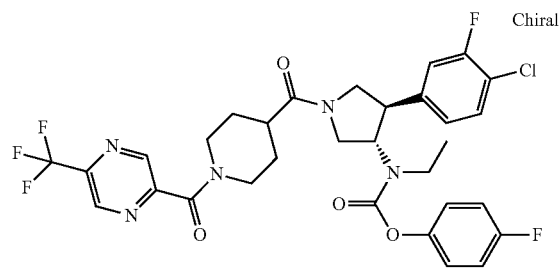 [SMILES: CCN(C(=O)Oc1ccc(F)cc1)[C@@H]1CN(C(=O)C2CCN(C(=O)c3cnc(C(F)(F)F)cn3)CC2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 5-(trifluoromethyl)pyrazine-2-carboxylic acid. MS m/e: 666.2 [M+H]$^+$.

Example 79

{(3S,4R)-4-(4-Chloro-3-fluoro-phenyl)-1-[1-(6-cyano-pyridine-3-carbonyl)-piperidine-4-carbonyl]-pyrrolidin-3-yl}-ethyl-carbamic acid 4-fluoro-phenyl ester

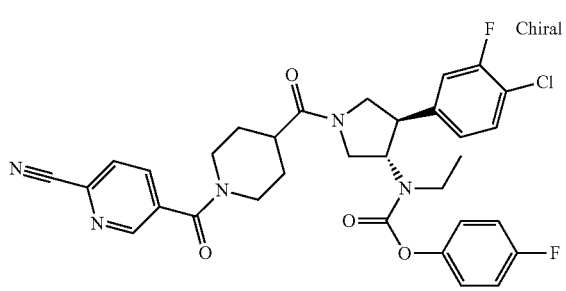 [SMILES: CCN(C(=O)Oc1ccc(F)cc1)[C@@H]1CN(C(=O)C2CCN(C(=O)c3ccc(C#N)nc3)CC2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and 6-cyanonicotinic acid. MS m/e: 622.4 [M+H]$^+$.

Example 80

[(3S,4R)-1-(1-Acetyl-piperidine-4-carbonyl)-4-(4-chloro-3-fluoro-phenyl)-pyrrolidin-3-yl]-ethyl-carbamic acid 4-fluoro-phenyl ester

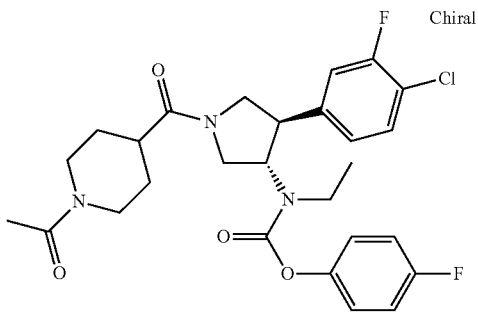 [SMILES: CCN(C(=O)Oc1ccc(F)cc1)[C@@H]1CN(C(=O)C2CCN(C(C)=O)CC2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-1-(piperidine-4-carbonyl)-pyrrolidin-3-yl]-ethyl-carbamic acid 4-fluoro-phenyl ester and acetic acid. MS m/e: 534.2 [M+H]$^+$.

Example 81

[(3S,4R)-4-(4-Chloro-3-fluoro-phenyl)-1-(1-methanesulfonyl-piperidine-4-carbonyl)-pyrrolidin-3-yl]-ethyl-carbamic acid 4-fluoro-phenyl ester

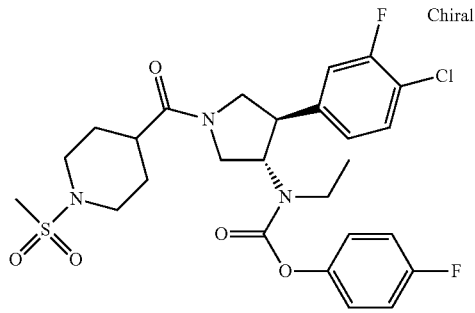 [SMILES: CCN(C(=O)Oc1ccc(F)cc1)[C@@H]1CN(C(=O)C2CCN(S(C)(=O)=O)CC2)C[C@H]1c1ccc(Cl)c(F)c1]

A mixture of 32 mg (0.065 mmol) [(3S,4R)-4-(4-Chloro-3-fluoro-phenyl)-1-(piperidine-4-carbonyl)-pyrrolidin-3-yl]-ethyl-carbamic acid 4-fluoro-phenyl ester, 57 uL (0.325 mmol) DIPEA and 11.2 mg (0.097 mmol) mesyl chloride in 1.5 mL DMF was shaken for 90 min at room temperature. The mixture was subjected to purification by preparative HPLC on reversed phase eluting with a gradient formed from acetonitrile, water and NEt$_3$. The product containing fractions were evaporated to yield 16 mg (43%) of the title compound as off-white solid. MS m/e: 570.4 [M+11]$^+$.

Example 82

[(3S,4R)-1-(1-Acetyl-piperidine-4-carbonyl)-4-(4-chloro-phenyl)-pyrrolidin-3-yl]-ethyl-carbamic acid 4-fluoro-phenyl ester

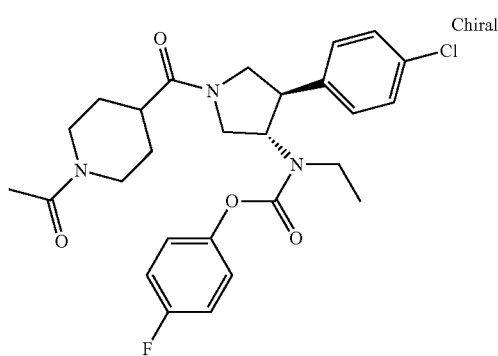 [SMILES: CCN(C(=O)Oc1ccc(F)cc1)[C@@H]1CN(C(=O)C2CCN(C(C)=O)CC2)C[C@H]1c1ccc(Cl)cc1]

a) [(3S,4R)-1-Benzyl-4-(4-chloro-phenyl)-pyrrolidin-3-yl]-ethyl-carbamic acid 4-fluoro-phenyl ester

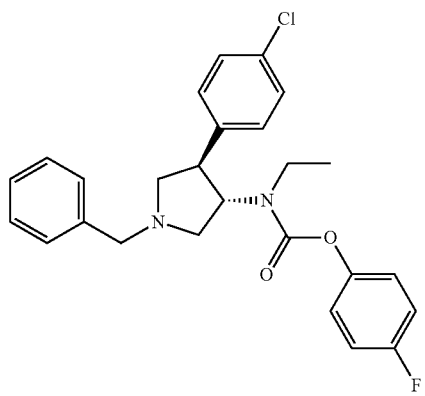 [SMILES: CCN(C(=O)Oc1ccc(F)cc1)[C@@H]1CN(Cc2ccccc2)C[C@H]1c1ccc(Cl)cc1]

The title compound was prepared from rac-[(3S,4R)-1-Benzyl-4-(4-chloro-phenyl)-pyrrolidin-3-yl]-ethyl-carbamic acid 4-fluoro-phenyl ester (example 7, c) through chiral column chromatography on Chiralpak AD. MS m/e: 453.3 [M+H]$^+$.

b) [(3S,4R)-4-(4-Chloro-phenyl)-pyrrolidin-3-yl] ethyl-carbamic acid 4-fluoro-phenyl ester

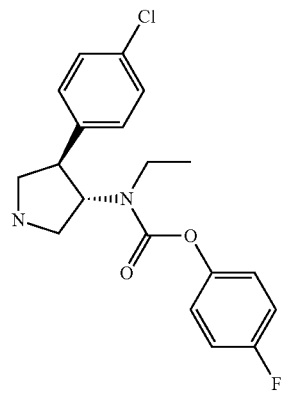 [SMILES: CCN(C(=O)Oc1ccc(F)cc1)[C@@H]1CNC[C@H]1c1ccc(Cl)cc1]

In analogy to the procedure described for the synthesis of d) rac-(3S,4R)-[4-(3,4-Dichloro-phenyl)-pyrrolidin-3-yl]-carbamic acid tert-butyl ester (example 1, d) the title compound was prepared from [(3S,4R)-1-Benzyl-4-(4-chloro-phenyl)-pyrrolidin-3-yl]-ethyl-carbamic acid 4-fluoro-phenyl ester as light brown foam which was used crude in the subsequent step. MS m/e: 363.2 [M+H]$^+$.

c) [(3S,4R)-1-(1-Acetyl-piperidine-4-carbonyl)-4-(4-chloro-phenyl)-pyrrolidin-3-yl]-ethyl-carbamic acid 4-fluoro-phenyl ester In analogy to the procedure described for the synthesis of [(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester (example 20) the title compound was prepared from [(3S,4R)-4-(4-Chloro-phenyl)-pyrrolidin-3-yl]ethyl-carbamic acid 4-fluoro-phenyl ester and 1-acetylpiperidine-4-carboxylic acid. MS m/e: 516.2 [M+H]$^+$.

Example 83

{(3S,4R)-4-(4-Chloro-3-fluoro-phenyl)-1-[5'-(1-hydroxy-1-methyl-ethyl)-3,4,5,6-tetrahydro-2H-[1,2']bipyridinyl-4-carbonyl]-pyrrolidin-3-yl}-ethyl-carbamic acid 4-fluoro-phenyl ester

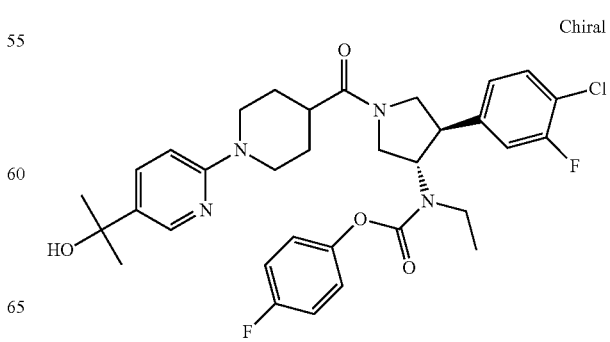

A mixture of 142 mg (0.23 mmol) [(3S,4R)-1-(5'-Acetyl-3,4,5,6-tetrahydro-2H-[1,2]bipyridinyl-4-carbonyl)-4-(4-chloro-3-fluoro-phenyl)-pyrrolidin-3-yl]-ethyl-carbamic acid 4-fluoro-phenyl ester (example 59) and 0.097 mL (0.29 mmol) methylmagnesium iodide (3M) in 5 mL was stirred from 0° to 15° C. during 90 min and quenched at 0° C. with NH$_4$Cl (aq.). The mixture was extracted with ethyl acetate and the combined organic layers were dried with Na$_2$SO$_4$ and evaporated. The residue was subjected to preparative HPLC on reversed phase eluting with a gradient formed from acetonitrile, water and NEt$_3$. The product containing fractions were evaporated to yield 19 mg (13%) of the title compound as white solid. MS m/e: 627.2 [M+11]$^+$.

Example 84

{(3S,4R)-4-(4-Chloro-phenyl)-1-[1-(3-methyl-oxetane-3-carbonyl)-piperidine-4-carbonyl]-pyrrolidin-3-yl}-ethyl-carbamic acid 2-fluoro-phenyl ester

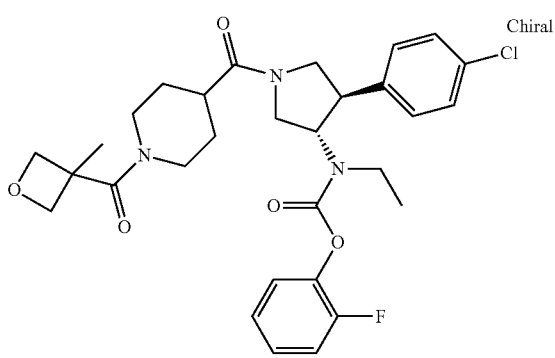 [SMILES: CCN(C(=O)Oc1ccccc1F)[C@@H]1CN(C(=O)C2CCN(C(=O)C3(C)COC3)CC2)C[C@H]1c1ccc(Cl)cc1]

a) rac-[(3S,4R)-1-Benzyl-4-(4-chloro-phenyl)-pyrrolidin-3-yl]-ethyl-carbamic acid 2-fluoro-phenyl ester

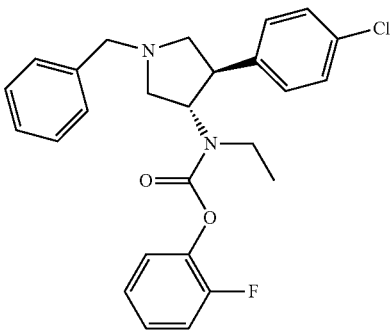 [SMILES: CCN(C(=O)Oc1ccccc1F)[C@@H]1CN(Cc2ccccc2)C[C@H]1c1ccc(Cl)cc1]

In analogy to the procedure described for the synthesis of rac-[(3S,4R)-1-Benzyl-4-(4-chloro-phenyl)-pyrrolidin-3-yl]-ethyl-carbamic acid 4-fluoro-phenyl ester (example 7, c) the title compound was prepared from rac-(3S,4R)-1-benzyl-4-(4-chloro-phenyl)-pyrrolidin-3-ylamine through reductive amination with acetaldehyde and subsequent reaction with 2-fluorophenyl chloroformate as light yellow oil. MS m/e: 453.1 [M+H]$^+$.

b) [(3S,4R)-1-Benzyl-4-(4-chloro-phenyl)-pyrrolidin-3-yl]-ethyl-carbamic acid 2-fluoro-phenyl ester

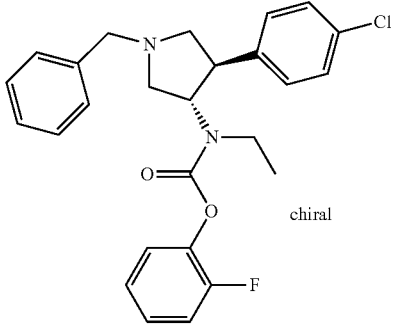 [SMILES: CCN(C(=O)Oc1ccccc1F)[C@@H]1CN(Cc2ccccc2)C[C@H]1c1ccc(Cl)cc1]

The title compound was prepared from rac-[(3S,4R)-1-Benzyl-4-(4-chloro-phenyl)-pyrrolidin-3-yl]-ethyl-carbamic acid 2-fluoro-phenyl ester through chiral column chromatography on Chiralpak AD. MS m/e: 453.1 [M+H]$^+$.

c) [(3S,4R)-4-(4-Chloro-phenyl)-pyrrolidin-3-yl] ethyl-carbamic acid 2-fluoro-phenyl ester

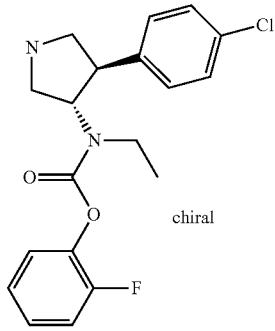 [SMILES: CCN(C(=O)Oc1ccccc1F)[C@@H]1CNC[C@H]1c1ccc(Cl)cc1]

In analogy to the procedure described for the synthesis of d) rac-(3S,4R)-[4-(3,4-Dichloro-phenyl)-pyrrolidin-3-yl]-carbamic acid tert-butyl ester (example 1, d) the title compound was prepared from [(3S,4R)-1-Benzyl-4-(4-chloro-phenyl)-pyrrolidin-3-yl]-ethyl-carbamic acid 2-fluoro-phenyl ester as light brown foam which was used crude in the subsequent step. MS m/e: 363.3 [M+H]$^+$.

d) [(3S,4R)-4-(4-Chloro-phenyl)-1-(piperidine-4-carbonyl)-pyrrolidin-3-yl]-ethyl-carbamic acid 2-fluoro-phenyl ester

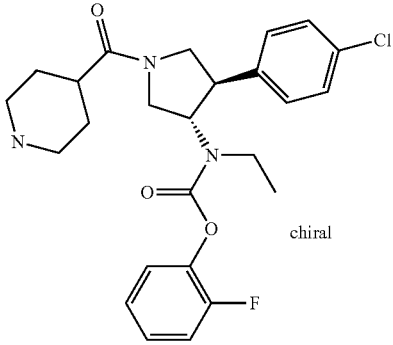 [SMILES: CCN(C(=O)Oc1ccccc1F)[C@@H]1CN(C(=O)C2CCNCC2)C[C@H]1c1ccc(Cl)cc1]

In analogy to the procedure described for the synthesis of [(3R,4S)-4-(4-Chloro-phenyl)-1-(piperidine-4-carbonyl)-pyrrolidin-3-yl]-ethyl-carbamic acid 4-fluoro-phenyl ester (example 7, f) the title compound was prepared from [(3S,4R)-4-(4-Chloro-phenyl)-pyrrolidin-3-yl]-ethyl-carbamic acid 2-fluoro-phenyl ester and 1-(tert-butoxycarbonyl)piperidine-4-carboxylic acid (coupling according to example 7, d) and subsequent removal of the Boc-protecting group (example 7, e) as light yellow foam. MS m/e: 474.2 [M+H]$^+$.

e) {(3S,4R)-4-(4-Chloro-phenyl)-1-[1-(3-methyl-oxetane-3-carbonyl)-piperidine-4-carbonyl]-pyrrolidin-3-yl}-ethyl-carbamic acid 2-fluoro-phenyl ester In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 2-fluoro-phenyl ester and 1-(1-methylcyclopropanecarbonyl)piperidine-4-carboxylic acid. MS m/e: 572.2 [M+H]$^+$.

Example 85

{(3S,4R)-4-(4-Chloro-phenyl)-1-[1-(1-cyano-cyclopropanecarbonyl)-piperidine-4-carbonyl]-pyrrolidin-3-yl}-ethyl-carbamic acid 2-fluoro-phenyl ester

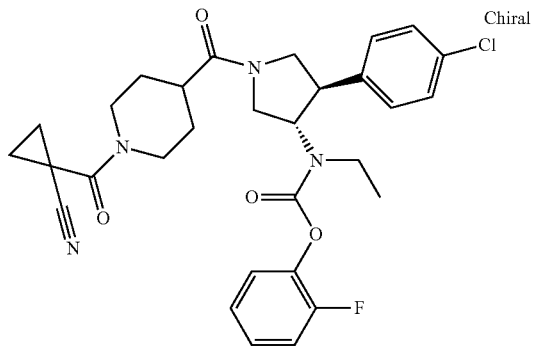 [SMILES: CCN(C(=O)Oc1ccccc1F)[C@@H]1CN(C(=O)C2CCN(C(=O)C3(C#N)CC3)CC2)C[C@H]1c1ccc(Cl)cc1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 2-fluoro-phenyl ester and 1-cyanocyclopropanecarboxylic acid. MS m/e: 567.3 [M+H]$^+$.

Example 86

{(3S,4R)-4-(4-Chloro-phenyl)-1-[1-(5-trifluoromethyl-pyridine-2-carbonyl)-piperidine-4-carbonyl]-pyrrolidin-3-yl}-ethyl-carbamic acid 2-fluoro-phenyl ester

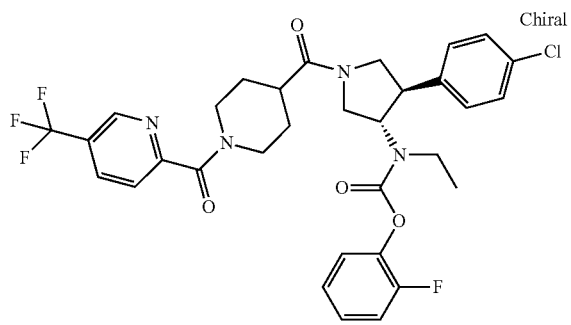 [SMILES: CCN(C(=O)Oc1ccccc1F)[C@@H]1CN(C(=O)C2CCN(C(=O)c3ccc(C(F)(F)F)cn3)CC2)C[C@H]1c1ccc(Cl)cc1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 2-fluoro-phenyl ester and 5-(trifluoromethyl) picolinic acid. MS m/e: 647.7 [M+H]$^+$.

Example 87

[(3S,4R)-4-(4-Chloro-phenyl)-1-(1-cyclobutanecarbonyl-piperidine-4-carbonyl)-pyrrolidin-3-yl]-ethyl-carbamic acid 4-fluoro-phenyl ester

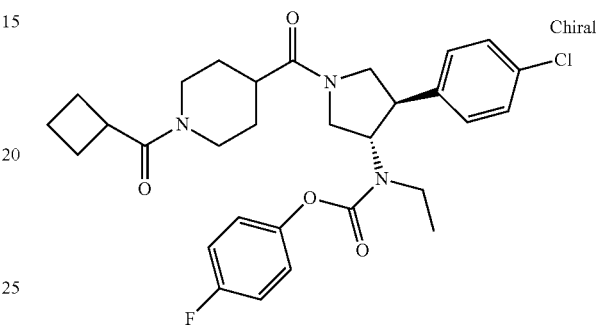

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and cyclobutanecarboxylic acid. MS m/e: 556.2 [M+H]$^+$.

Example 88

{(3S,4R)-4-(4-Chloro-phenyl)-1-[1-(3-methyl-oxetane-3-carbonyl)-piperidine-4-carbonyl]-pyrrolidin-3-yl}-ethyl-carbamic acid 4-fluoro-phenyl ester

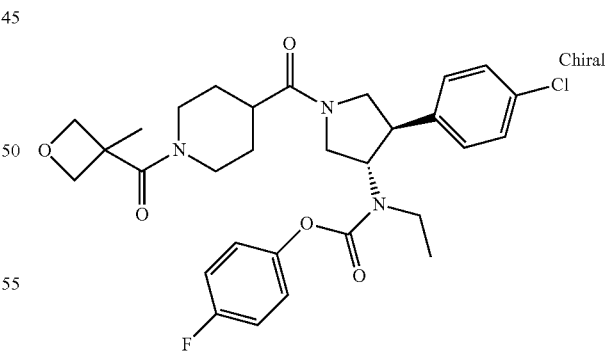

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 3-methyloxetane-3-carboxylic acid. MS m/e: 572.2 [M+H]$^+$.

Example 89

{(3S,4R)-4-(4-Chloro-phenyl)-1-[1-(3-fluoro-cyclobutanecarbonyl)-piperidine-4-carbonyl]-pyrrolidin-3-yl}-ethyl-carbamic acid 4-fluoro-phenyl ester

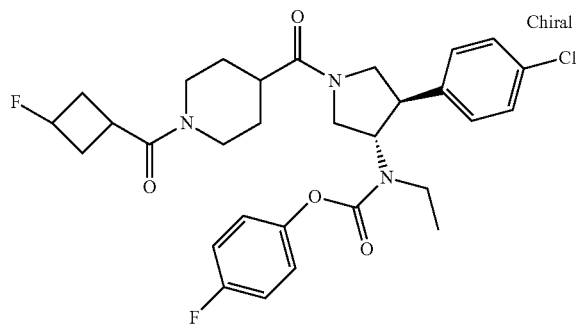 [SMILES: CCN(C(=O)Oc1ccc(F)cc1)[C@@H]1CN(C(=O)C2CCN(C(=O)C3CC(F)C3)CC2)C[C@H]1c1ccc(Cl)cc1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 3-fluorocyclobutanecarboxylic acid. MS m/e: 574.2 [M+H]$^+$.

Example 90

{(3S,4R)-4-(4-Chloro-phenyl)-1-[1-(3,3-difluoro-cyclobutanecarbonyl)-piperidine-4-carbonyl]-pyrrolidin-3-yl}-ethyl-carbamic acid 4-fluoro-phenyl ester

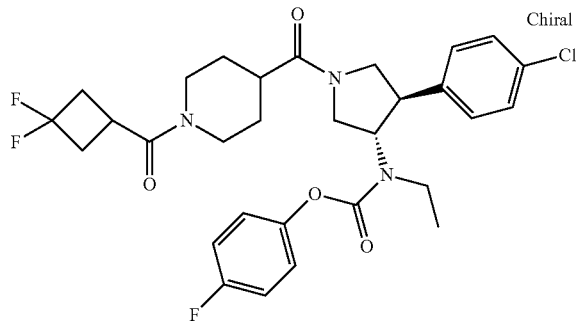 [SMILES: CCN(C(=O)Oc1ccc(F)cc1)[C@@H]1CN(C(=O)C2CCN(C(=O)C3CC(F)(F)C3)CC2)C[C@H]1c1ccc(Cl)cc1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 3,3-difluorocyclobutanecarboxylic acid. MS m/e: 592.3 [M+H]$^+$.

Example 91

{(3S,4R)-4-(4-Chloro-phenyl)-1-[1-(3-methoxy-cyclobutanecarbonyl)-piperidine-4-carbonyl]-pyrrolidin-3-yl}-ethyl-carbamic acid 4-fluoro-phenyl ester

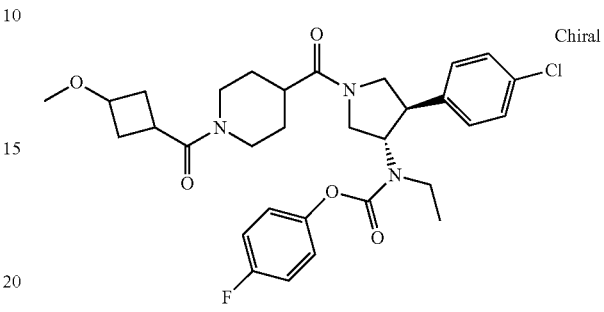

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 3-methoxycyclobutanecarboxylic acid. MS m/e: 586.2 [M+H]$^+$.

Example 92

{(3S,4R)-4-(4-Chloro-phenyl)-1-[1-(1-trifluoromethyl-cyclobutanecarbonyl)-piperidine-4-carbonyl]-pyrrolidin-3-yl}-ethyl-carbamic acid 4-fluoro-phenyl ester

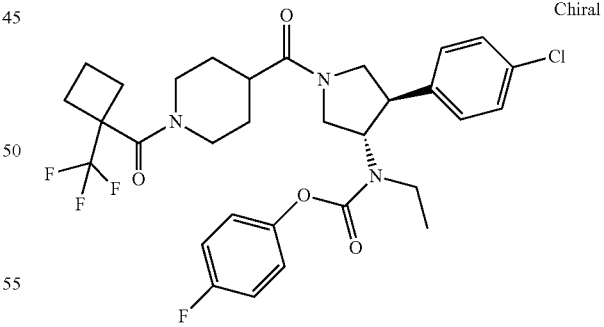

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 1-(trifluoromethyl)cyclobutanecarboxylic acid. MS m/e: 624.1 [M+H]$^+$.

Example 93

{(3S,4R)-4-(4-Chloro-phenyl)-1-[1-(2-cyano-acetyl)-piperidine-4-carbonyl]-pyrrolidin-3-yl}-ethyl-carbamic acid 4-fluoro-phenyl ester

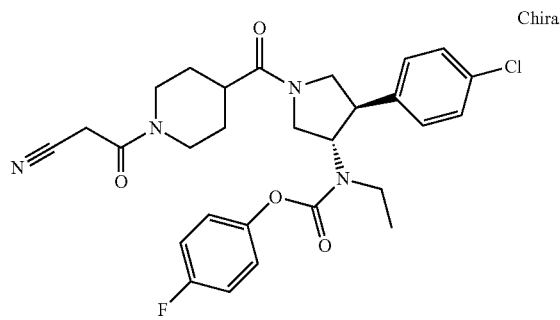 [SMILES: CCN(C(=O)Oc1ccc(F)cc1)[C@@H]1CN(C(=O)C2CCN(C(=O)CC#N)CC2)C[C@H]1c1ccc(Cl)cc1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 2-cyanoacetic acid. MS m/e: 541.3 [M+H]$^+$.

Example 94

{(3S,4R)-4-(4-Chloro-phenyl)-1-[1-(1-cyano-cyclopropanecarbonyl)-piperidine-4-carbonyl]-pyrrolidin-3-yl}-ethyl-carbamic acid 4-fluoro-phenyl ester

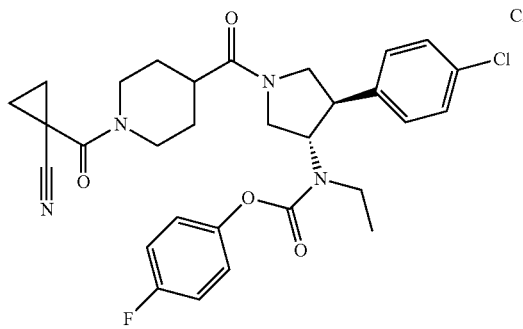

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 1-cyanocyclopropanecarboxylic acid. MS m/e: 567.3 [M+H]$^+$.

Example 95

{(3S,4R)-4-(4-Chloro-phenyl)-1-[1-(1-trifluoromethyl-cyclopropanecarbonyl)-piperidine-4-carbonyl]-pyrrolidin-3-yl}-ethyl-carbamic acid 4-fluoro-phenyl ester

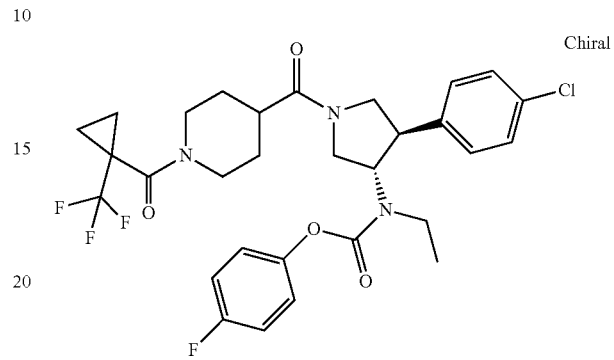

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 1-(trifluoromethyl)cyclopropanecarboxylic acid. MS m/e: 610.2 [M+H]$^+$.

Example 96

{(3S,4R)-4-(4-Chloro-phenyl)-1-[1-(2,2-difluoro-cyclopropanecarbonyl)-piperidine-4-carbonyl]-pyrrolidin-3-yl}-ethyl-carbamic acid 4-fluoro-phenyl ester

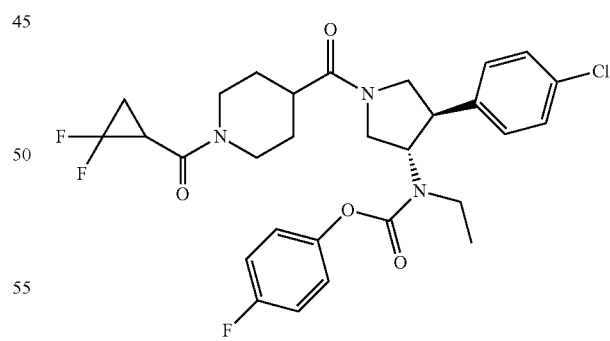

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 2,2-difluorocyclopropanecarboxylic acid. MS m/e: 578.3 [M+H]$^+$.

Example 97

{(3S,4R)-4-(4-Chloro-phenyl)-1-[1-(tetrahydro-pyran-4-carbonyl)-piperidine-4-carbonyl]-pyrrolidin-3-yl}-ethyl-carbamic acid 4-fluoro-phenyl ester

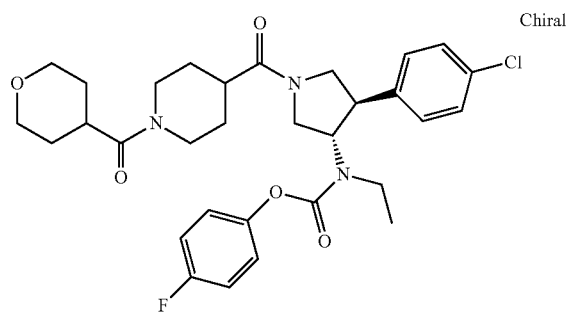 [SMILES: CCN(C(=O)Oc1ccc(F)cc1)[C@@H]1CN(C(=O)C2CCN(C(=O)C3CCOCC3)CC2)C[C@H]1c1ccc(Cl)cc1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and tetrahydro-2H-pyran-4-carboxylic acid. MS m/e: 586.3 [M+H]⁺.

Example 98

{(3S,4R)-4-(4-Chloro-phenyl)-1-[1-(2,2-dimethyl-tetrahydro-pyran-4-carbonyl)-piperidine-4-carbonyl]-pyrrolidin-3-yl}-ethyl-carbamic acid 4-fluoro-phenyl ester

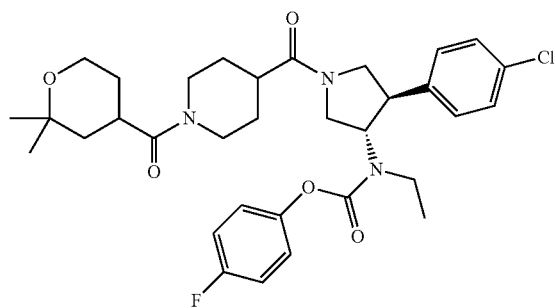 [SMILES: CCN(C(=O)Oc1ccc(F)cc1)[C@@H]1CN(C(=O)C2CCN(C(=O)C3CCOC(C)(C)C3)CC2)C[C@H]1c1ccc(Cl)cc1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 2,2-dimethyltetrahydro-2H-pyran-4-carboxylic acid. MS m/e: 614.2 [M+H]⁺.

Example 99

{(3S,4R)-4-(4-Chloro-phenyl)-1-[1-(1-methoxymethyl-cyclopropanecarbonyl)-piperidine-4-carbonyl]-pyrrolidin-3-yl}-ethyl-carbamic acid 4-fluoro-phenyl ester

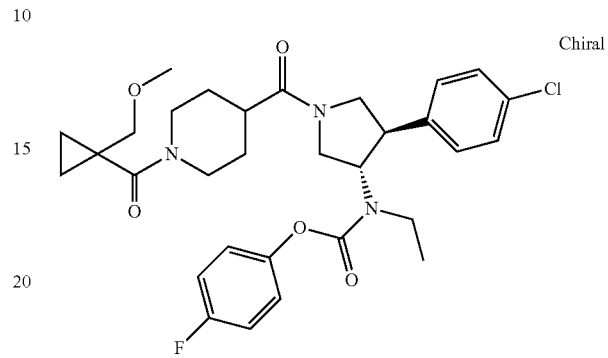

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 1-(methoxymethyl)cyclopropanecarboxylic acid. MS m/e: 586.3 [M+H]⁺.

Example 100

{(3S,4R)-4-(4-Chloro-phenyl)-1-[1-(2,2-dimethyl-cyclopropanecarbonyl)-piperidine-4-carbonyl]-pyrrolidin-3-yl}-ethyl-carbamic acid 4-fluoro-phenyl ester

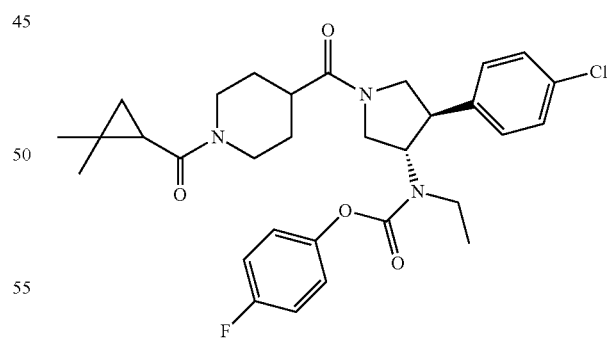

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 2,2-dimethylcyclopropanecarboxylic acid. MS m/e: 570.2 [M+H]⁺.

Example 101

{(3S,4R)-4-(4-Chloro-phenyl)-1-[1-(5-trifluoromethyl-pyridine-2-carbonyl)-piperidine-4-carbonyl]-pyrrolidin-3-yl}-ethyl-carbamic acid 4-fluoro-phenyl ester

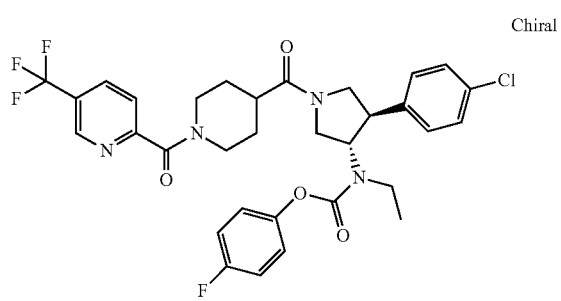 [SMILES: CCN(C(=O)Oc1ccc(F)cc1)[C@@H]1CN(C(=O)C2CCN(C(=O)c3ccc(C(F)(F)F)cn3)CC2)C[C@H]1c1ccc(Cl)cc1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 5-(trifluoromethyl)picolinic acid. MS m/e: 647.3 [M+H]$^+$.

Example 102

{(3S,4R)-4-(4-Chloro-phenyl)-1-[1-(5-fluoro-pyridine-2-carbonyl)-piperidine-4-carbonyl]-pyrrolidin-3-yl}-ethyl-carbamic acid 4-fluoro-phenyl ester

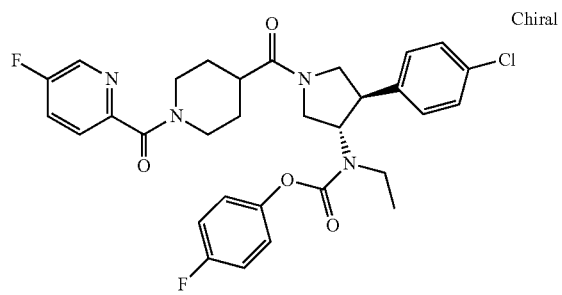 [SMILES: CCN(C(=O)Oc1ccc(F)cc1)[C@@H]1CN(C(=O)C2CCN(C(=O)c3ccc(F)cn3)CC2)C[C@H]1c1ccc(Cl)cc1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 5-fluoropicolinic acid. MS m/e: 597.2 [M+H]$^+$.

Example 103

{(3S,4R)-4-(4-Chloro-phenyl)-1-[1-(6-oxo-piperidine-3-carbonyl)-piperidine-4-carbonyl]-pyrrolidin-3-yl}-ethyl-carbamic acid 4-fluoro-phenyl ester

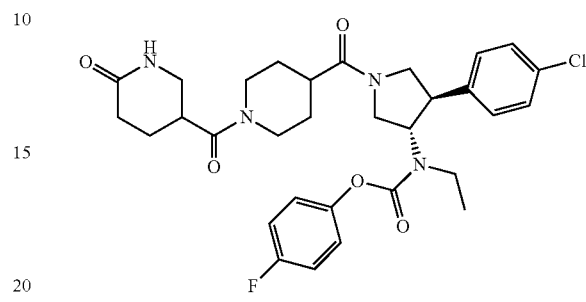

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 6-oxopiperidine-3-carboxylic acid. MS m/e: 599.2 [M+H]$^+$.

Example 104

{(3S,4R)-4-(4-Chloro-phenyl)-1-[1-(1-isopropyl-6-oxo-piperidine-3-carbonyl)-piperidine-4-carbonyl]-pyrrolidin-3-yl}-ethyl-carbamic acid 4-fluoro-phenyl ester

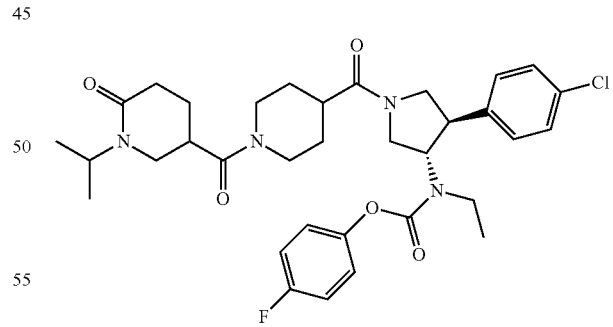

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-1-(piperidine-4-carbonyl)-pyrrolidin-3-yl]-ethyl-carbamic acid 4-fluoro-phenyl ester and 1-isopropyl-6-oxopiperidine-3-carboxylic acid. MS m/e: 641.4 [M+H]$^+$.

Example 105

[(3S,4R)-4-(4-Chloro-3-fluoro-phenyl)-1-(1-isopropyl-6-oxo-piperidine-3-carbonyl)-pyrrolidin-3-yl]-ethyl-carbamic acid 4-fluoro-phenyl ester

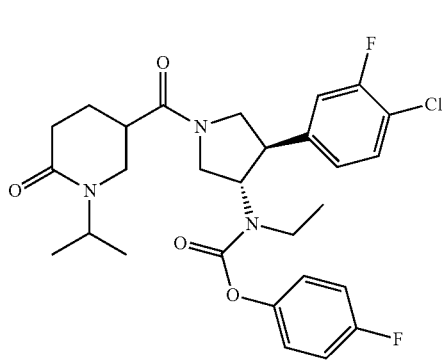 [SMILES: CCN(C(=O)Oc1ccc(F)cc1)[C@@H]1CN(C(=O)C2CCC(=O)N(C(C)C)C2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-pyrrolidin-3-yl]-ethyl-carbamic acid 4-fluoro-phenyl ester (example 39, h) and 1-isopropyl-6-oxopiperidine-3-carboxylic acid. MS m/e: 548.3 [M+H]⁺.

Example 106

{(3S,4R)-4-(3,4-Difluoro-phenyl)-1-[1-((S)-4-oxo-azetidine-2-carbonyl)-piperidine-4-carbonyl]-pyrrolidin-3-yl}-ethyl-carbamic acid 4-fluoro-phenyl ester

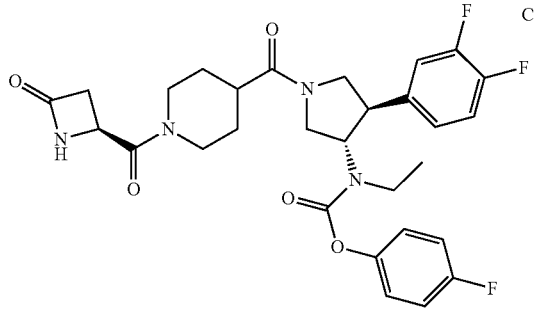

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Difluoro-phenyl)-1-(piperidine-4-carbonyl)-pyrrolidin-3-yl]-ethyl-carbamic acid 4-fluoro-phenyl ester (example 58, b) and (S)-4-oxoazetidine-2-carboxylic acid. MS m/e: 573.2 [M+H]⁺.

Example 107

{(3S,4R)-4-(3,4-Difluoro-phenyl)-1-[1-(6-oxo-piperidine-3-carbonyl)-piperidine-4-carbonyl]-pyrrolidin-3-yl}-ethyl-carbamic acid 4-fluoro-phenyl ester

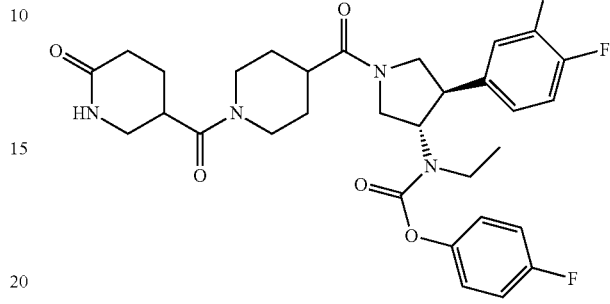

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Difluoro-phenyl)-1-(piperidine-4-carbonyl)-pyrrolidin-3-yl]-ethyl-carbamic acid 4-fluoro-phenyl ester (example 58, b) and 6-oxopiperidine-3-carboxylic acid. MS m/e: 601.3 [M+H]⁺.

Example 108

{(3S,4R)-4-(4-Chloro-phenyl)-1-[5'-(1-hydroxy-ethyl)-3,4,5,6-tetrahydro-2H-[1,2]bipyridinyl-4-carbonyl]-pyrrolidin-3-yl}-ethyl-carbamic acid 4-fluoro-phenyl ester

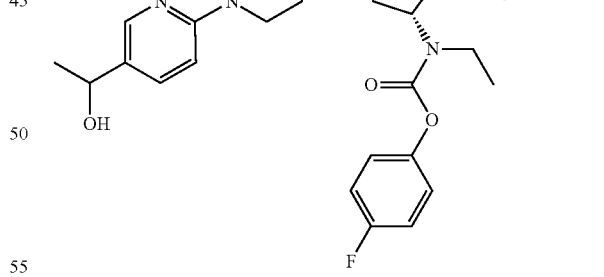

A mixture of 62 mg (0.15 mmol) [(3S,4R)-1-(5'-Acetyl-3,4,5,6-tetrahydro-2H-[1,2]bipyridinyl-4-carbonyl)-4-(4-chloro-phenyl)-pyrrolidin-3-yl]-ethyl-carbamic acid 4-fluoro-phenyl ester (example 14) and 3.95 mg (0.105 mmol) sodium borohydride in 2 mL THF/0.2 mL MeOH was stirred at room temperature for 45 minutes. Water was added and the mixture was extracted with ethyl acetate. The combined organic layers were dried with Na₂SO₄, filtered and evaporated to dryness to yield 58 mg (93%) of the title compound as off-white solid. MS m/e: 595.2 [M+H]⁺.

Example 109

[(3S,4R)-1-(5'-Carbamoyl-3,4,5,6-tetrahydro-2H-[1,2']bipyridinyl-4-carbonyl)-4-(4-chloro-3-fluoro-phenyl)-pyrrolidin-3-yl]-ethyl-carbamic acid 4-fluoro-phenyl ester

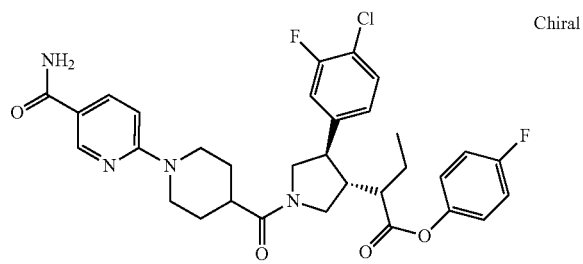 [SMILES: CCC(C(=O)Oc1ccc(F)cc1)[C@@H]1CN(C(=O)C2CCN(c3ccc(C(N)=O)cn3)CC2)C[C@H]1c1ccc(Cl)c(F)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-3-fluoro-phenyl)-pyrrolidin-3-yl]-ethyl-carbamic acid 4-fluoro-phenyl ester (example 39, h) and 1-[5-(aminocarbonyl)pyridine-2-yl]piperidine-4-carboxylic acid. MS m/e: 612.3 [M+H]+.

Example 110

[(3S,4R)-4-(4-Chloro-phenyl)-1-(5'-chloro-3,4,5,6-tetrahydro-2H-[1,2']bipyridinyl-4-carbonyl)-pyrrolidin-3-yl]-ethyl-carbamic acid 4-fluoro-phenyl ester

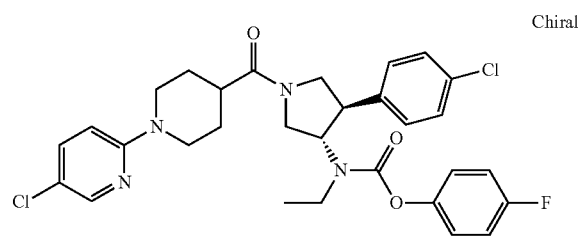 [SMILES: CCN(C(=O)Oc1ccc(F)cc1)[C@@H]1CN(C(=O)C2CCN(c3ccc(Cl)cn3)CC2)C[C@H]1c1ccc(Cl)cc1]

a) [(3S,4R)-1-Benzyl-4-(4-chloro-phenyl)-pyrrolidin-3-yl]-carbamic acid tert-butyl ester

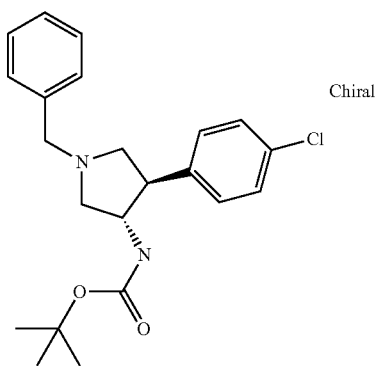 [SMILES: CC(C)(C)OC(=O)N[C@@H]1CN(Cc2ccccc2)C[C@H]1c1ccc(Cl)cc1]

In analogy to the procedure described for the synthesis of [(3S,4R)-1-Benzyl-4-(3,4-difluoro-phenyl)-pyrrolidin-3-yl]-carbamic acid tert-butyl ester (example 48, e) the title compound was prepared following the sequence as described in example 48, b to e starting from ethyl 3-(4-chlorophenyl) propiolate and N-(methoxymethyl)-N-(trimethylsilylmethyl)benzylamine as off-white solid. MS m/e: 387.3 [M+H]+.

b) [(3S,4R)-1-Benzyl-4-(4-chloro-phenyl)-pyrrolidin-3-yl]-ethyl-carbamic acid tert-butyl ester

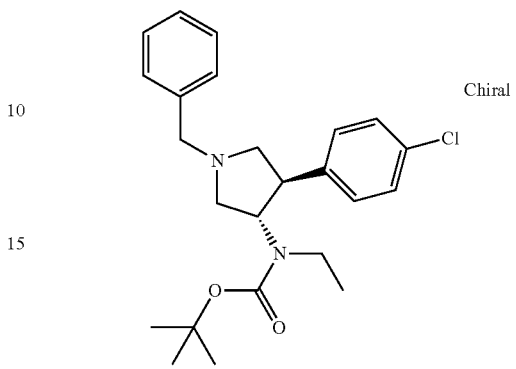

A mixture of 4.2 g (10.9 mmol) [(3S,4R)-1-Benzyl-4-(4-chloro-phenyl)-pyrrolidin-3-yl]-carbamic acid tert-butyl ester, 521 mg (13 mmol) NaH (60%) and 2.54 g (16.3 mmol) iodoethane in 40 mL DMF was stirred for 1 h at 60° C. and evaporated to dryness. The residue was taken up in ethyl acetate and water and extracted further with ethyl acetate. The combined organic layers were washed with brine, dried with Na2SO4, filtered and evaporated to dryness. The residue was purified by column chromatography on silica eluting with a gradient formed from ethyl acetate and heptane to yield after evaporation of the product containing fractions 2.5 g (55%) of the title compound as light yellow viscous oil. MS m/e: 415.3 [M+H]+.

c) [(3S,4R)-4-(4-Chloro-phenyl)-pyrrolidin-3-yl]-ethyl-carbamic acid 4-fluoro-phenyl ester

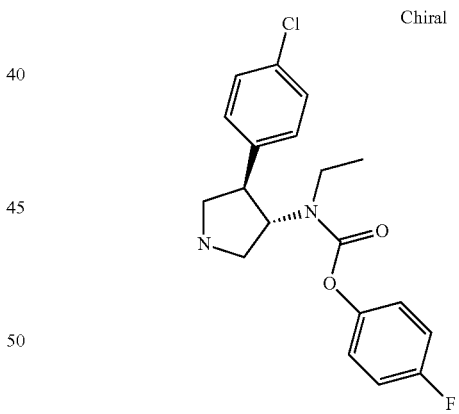

In analogy to the procedure described for rac-(3S,4R)-[3-Amino-4-(3,4-dichloro-phenyl)-pyrrolidin-1-yl]-[1-(1-methyl-cyclopropanecarbonyl)-piperidin-4-yl]-methanone (example 1, f) the Boc protecting group was removed. The liberated amine was reacted to the respective carbamate in analogy to the procedure described for the synthesis of rac-{(3S,4R)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester (example 1, h). The benzyl protecting group was removed in analogy to the procedure described for rac-(3S,4R)-[4-(3,4-Dichloro-phenyl)-pyrrolidin-3-yl]-carbamic acid tert-butyl ester (example 1, d) to yield the title compound as amorphous crude brown foam. MS m/e: 363.3 [M+H]+.

d) [(3S,4R)-4-(4-Chloro-phenyl)-1-(5'-chloro-3,4,5,6-tetrahydro-2H-[1,2']bipyridinyl-4-carbonyl)-pyrrolidin-3-yl]-ethyl-carbamic acid 4-fluoro-phenyl ester In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-pyrrolidin-3-yl]-ethyl-carbamic acid 4-fluoro-phenyl ester and 1-(5-chloropyridine-2-yl)piperidine-4-carboxylic acid. MS m/e: 585.2 [M+H]$^+$.

Example 111

[(3S,4R)-1-(5'-Carbamoyl-3,4,5,6-tetrahydro-2H-[1,2']bipyridinyl-4-carbonyl)-4-(4-chloro-phenyl)-pyrrolidin-3-yl]-ethyl-carbamic acid 4-fluoro-phenyl ester

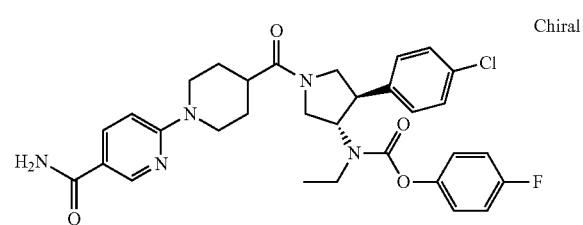 [SMILES: CCN(C(=O)Oc1ccc(F)cc1)[C@@H]1CN(C(=O)C2CCN(c3ccc(C(N)=O)cn3)CC2)C[C@H]1c1ccc(Cl)cc1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(4-Chloro-phenyl)-pyrrolidin-3-yl]ethyl-carbamic acid 4-fluoro-phenyl ester and 1-[5-(aminocarbonyl)pyridine-2-yl]piperidine-4-carboxylic acid. MS m/e: 594.3 [M+H]$^+$.

Example 112

[(3S,4R)-4-(3,4-Dichloro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester

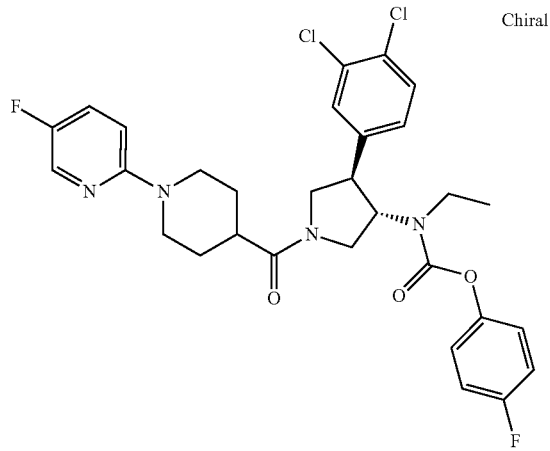 [SMILES: CCN(C(=O)Oc1ccc(F)cc1)[C@@H]1CN(C(=O)C2CCN(c3ccc(F)cn3)CC2)C[C@H]1c1ccc(Cl)c(Cl)c1]

a) [(3S,4R)-4-(3,4-Dichloro-phenyl)-pyrrolidin-3-yl]-ethyl-carbamic acid 4-fluoro-phenyl ester

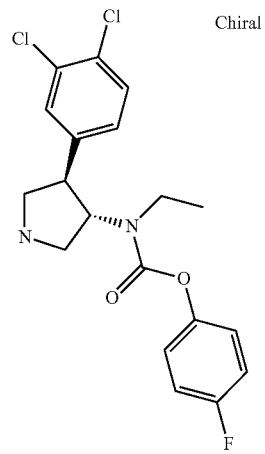 [SMILES: CCN(C(=O)Oc1ccc(F)cc1)[C@@H]1CNC[C@H]1c1ccc(Cl)c(Cl)c1]

In analogy to the procedure described for the synthesis of [(3S,4R)-4-(4-Chloro-phenyl)-pyrrolidin-3-yl]-ethyl-carbamic acid 4-fluoro-phenyl ester (example 110, c) the title compound was prepared following the same sequence of transformations described in example 110 starting from ethyl 3-(3,4-dichlorophenyl)propiolate and N-(methoxymethyl)-N-(trimethylsilylmethyl)benzylamine as amorphous crude brown foam.

b) [(3S,4R)-4-(3,4-Dichloro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Dichloro-phenyl)-pyrrolidin-3-yl]-ethyl-carbamic acid 4-fluoro-phenyl ester and 1-(5-fluoropyridin-2-yl)piperidine-4-carboxylic acid. MS m/e: 603.2 [M+H]$^+$.

Example 113

[(3S,4R)-1-(5'-Chloro-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester

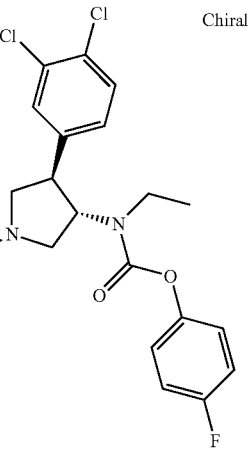

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Dichlorophenyl)-pyrrolidin-3-yl]-ethyl-carbamic acid 4-fluoro-phenyl ester and 1-(5-chloropyridin-2-yl)piperidine-4-carboxylic acid. MS m/e: 619.3 [M+H]$^+$.

Example 114

[(3S,4R)-4-(3,4-Dichloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluorophenyl ester

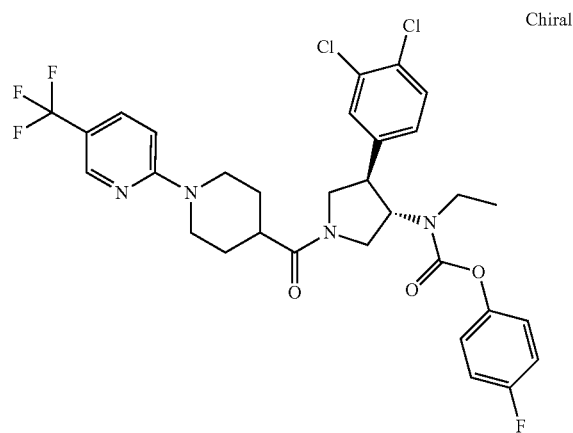 [SMILES: CCN(C(=O)Oc1ccc(F)cc1)[C@@H]1CN(C(=O)C2CCN(c3ccc(C(F)(F)F)cn3)CC2)C[C@H]1c1ccc(Cl)c(Cl)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Dichlorophenyl)-pyrrolidin-3-yl]-ethyl-carbamic acid 4-fluoro-phenyl ester and 1-(5-(trifluoromethyl)pyridin-2-yl)piperidine-4-carboxylic acid. MS m/e: 653.2 [M+H]$^+$.

Example 115

[(3S,4R)-1-(5'-Carbamoyl-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester

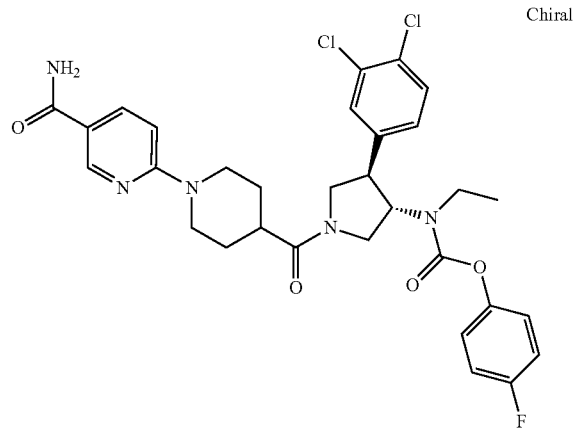 [SMILES: CCN(C(=O)Oc1ccc(F)cc1)[C@@H]1CN(C(=O)C2CCN(c3ccc(C(N)=O)cn3)CC2)C[C@H]1c1ccc(Cl)c(Cl)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Dichlorophenyl)-pyrrolidin-3-yl]-ethyl-carbamic acid 4-fluoro-phenyl ester and 1-(5-carbamoylpyridin-2-yl)piperidine-4-carboxylic acid. MS m/e: 628.4 [M+H]$^+$.

Example 116

[(3S,4R)-1-(5'-Acetyl-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester

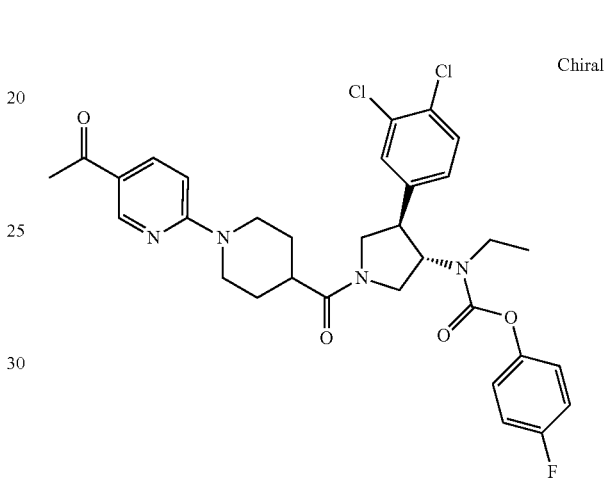

a) 4-{(3R,4S)-3-(3,4-Dichloro-phenyl)-4-[ethyl-(4-fluoro-phenoxycarbonyl)-amino]-pyrrolidine-1-carbonyl}-piperidine-1-carboxylic acid tert-butyl ester

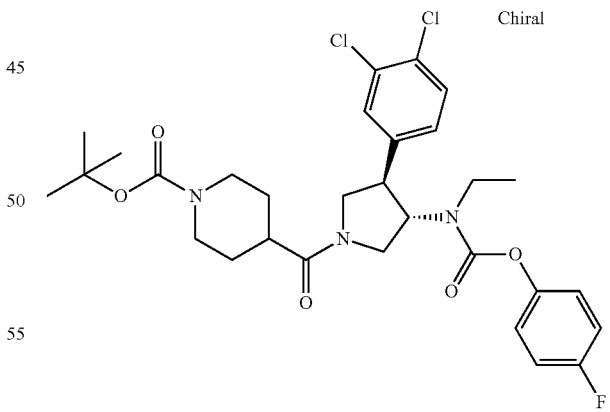

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3,4-Dichlorophenyl)-pyrrolidin-3-yl]-ethyl-carbamic acid 4-fluoro-phenyl ester and 1-(tert-butoxycarbonyl)piperidine-4-carboxylic acid. MS m/e: 608.0 [M+H]$^+$.

b) [(3S,4R)-1-(5'-Acetyl-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester After removal of the Boc-protecting group under acidic conditions, in analogy to the procedure described for the synthesis of {(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester (example 7, g) the title compound was prepared from [(3S,4R)-4-(3,4-Dichloro-phenyl)-1-(piperidine-4-carbonyl)-pyrrolidin-3-yl]-ethyl-carbamic acid 4-fluoro-phenyl ester and 5-acetyl-2-bromopyridine as off-white foam. MS m/e: 627.3 [M+H]+.

Example 117

[(3S,4R)-4-(3-Chloro-4-fluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester

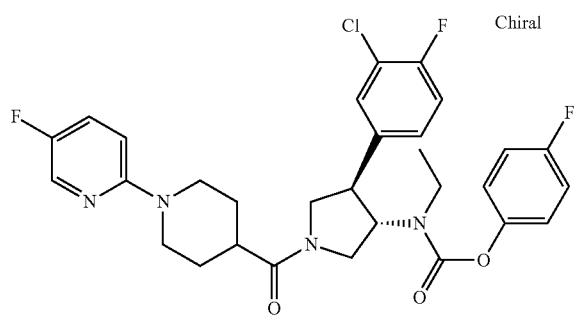

a) [(3S,4R)-4-(3-Chloro-4-fluoro-phenyl)-pyrrolidin-3-yl]-ethyl-carbamic acid 4-fluoro-phenyl ester

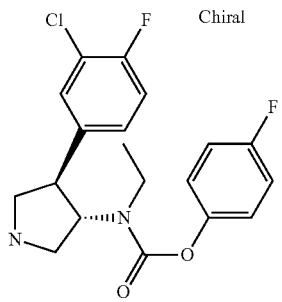

In analogy to the procedure described for the synthesis of [(3S,4R)-4-(4-Chloro-phenyl)-pyrrolidin-3-yl]-ethyl-carbamic acid 4-fluoro-phenyl ester (example 110, c) the title compound was prepared following the same sequence of transformations described in example 110 starting from (3-Chloro-4-fluoro-phenyl)-propynoic acid ethyl ester (prepared in analogy to (4-Chloro-3-fluoro-phenyl)-propynoic acid ethyl ester (example 39, step a)) and N-(methoxymethyl)-N-(trimethylsilylmethyl)benzylamine as amorphous crude brown solid.

b) [(3S,4R)-4-(3-Chloro-4-fluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3-Chloro-4-fluoro-phenyl)-pyrrolidin-3-yl]-ethyl-carbamic acid 4-fluoro-phenyl ester and 1-(5-fluoropyridin-2-yl)piperidine-4-carboxylic acid. MS m/e: 587.1 [M+H]+.

Example 118

[(3S,4R)-4-(3-Chloro-4-fluoro-phenyl)-1-(5'-chloro-3,4,5,6-tetrahydro-2H-[1,2']bipyridinyl-4-carbonyl)-pyrrolidin-3-yl]-ethyl-carbamic acid 4-fluoro-phenyl ester

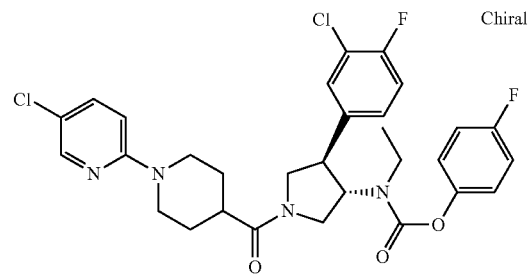 [SMILES: "Chiral" ; CCN(C(=O)Oc1ccc(F)cc1)[C@@H]1CN(C(=O)C2CCN(c3ccc(Cl)cn3)CC2)C[C@H]1c1ccc(F)c(Cl)c1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3-Chloro-4-fluoro-phenyl)-pyrrolidin-3-yl]-ethyl-carbamic acid 4-fluoro-phenyl ester and 1-(5-chloropyridin-2-yl)piperidine-4-carboxylic acid. MS m/e: 603.2 [M+H]+.

Example 119

[(3S,4R)-4-(3-Chloro-4-fluoro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester

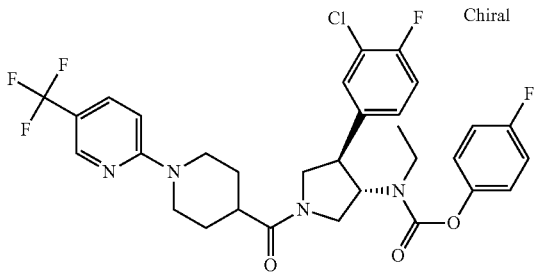

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethylcarbamic acid 4-fluoro-phenyl ester (example 35, step f) the title compound was prepared from [(3S,4R)-4-(3-Chloro-4-fluoro-phenyl)-pyrrolidin-3-yl]-ethyl-carbamic acid 4-fluoro-phenyl ester and 1-(5-(trifluoromethyl)pyridin-2-yl)piperidine-4-carboxylic acid. MS m/e: 637.3 [M+H]+.

Example 120

[(3S,4R)-1-(5'-Acetyl-3,4,5,6-tetrahydro-2H-[1,2'] bipyridinyl-4-carbonyl)-4-(3-chloro-4-fluoro-phenyl)-pyrrolidin-3-yl]-ethyl-carbamic acid 4-fluoro-phenyl ester

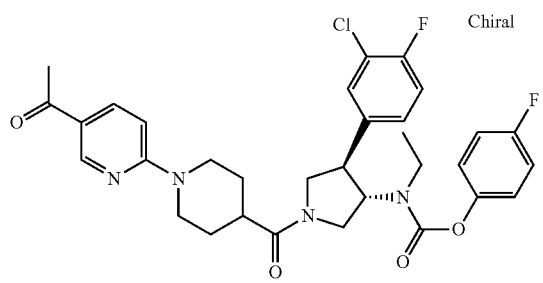

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was prepared from [(3S,4R)-4-(3-Chloro-4-fluoro-phenyl)-pyrrolidin-3-yl]-ethyl-carbamic acid 4-fluoro-phenyl ester and 1-(5-acetylpyridin-2-yl)piperidine-4-carboxylic acid. MS m/e: 611.3 [M+H]+.

Example 121

{(3S,4R)-4-(4-Chloro-phenyl)-1-[1-((S)-4-oxo-azetidine-2-carbonyl)-piperidine-4-carbonyl]-pyrrolidin-3-yl}-ethyl-carbamic acid 4-fluoro-phenyl ester

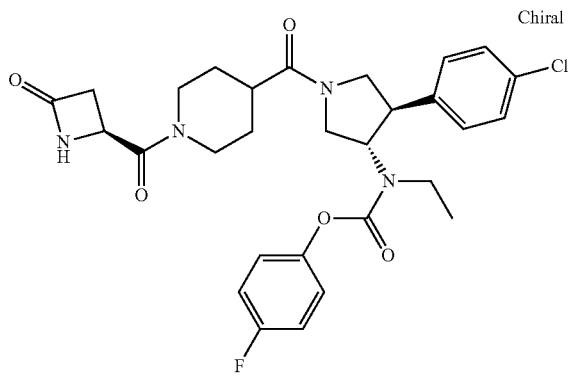 [SMILES: CCN(C(=O)Oc1ccc(F)cc1)[C@@H]1CN(C(=O)C2CCN(C(=O)[C@@H]3CC(=O)N3)CC2)C[C@H]1c1ccc(Cl)cc1]

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the title compound was from [(3S,4R)-4-(4-Chloro-phenyl)-pyrolidin-3-yl]-ethyl-carbamic acid 4-fluoro-phenyl ester and (S)-4-oxoazetidine-2-carboxylic acid. MS m/e: 571.2 [M+H]+.

Example 122

[(3S,4R)-1-[5'-(2-Diethylamino-acetyl)-3,4,5,6-tetrahydro-2H-[1,2']bipyridinyl-4-carbonyl]-4-(4-fluoro-phenyl)-pyrrolidin-3-yl]-ethyl-carbamic acid 4-fluoro-phenyl ester

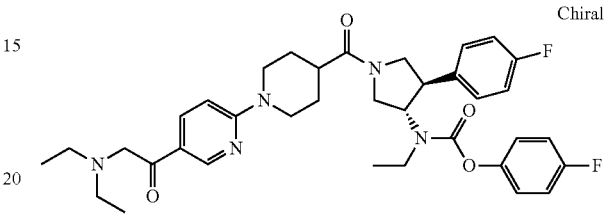

A mixture of 0.17 g (0.285 mmol) [(3S,4R)-1-(5'-Acetyl-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 38) and 84.3 mg (0.295 mmol) 5,5-dibromobarbituric acid in 10 mL dioxane was heated to 85° C. for 40 h. At room temperature 0.216 g (2.95 mmol) diethylamine was added and heated to 45° C. for 2 h and evaporated. the residue was taken up in methanol and subjected to preparative HPLC on reversed phase eluting with a gradient formed from acetonitrile, water and NEt3. The product containing fractions were evaporated to yield 49 mg (26%) of the title compound as light brown solid. MS m/e: 648.3 [M+H]+.

Example 123

Acetic acid 4-{(3R,4S)-3-(4-chloro-phenyl)-4-[ethyl-(4-fluoro-phenoxycarbonyl)-amino]-pyrrolidine-1-carbonyl}-3,4,5,6-tetrahydro-2H-[1,2']bipyridinyl-5'-yl ester

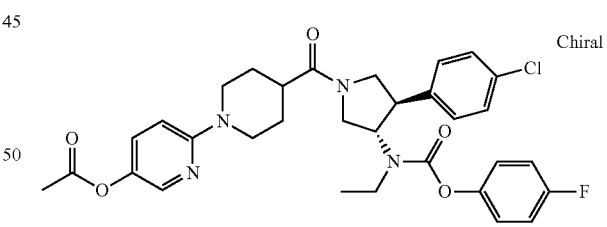

In analogy to the procedure described for the synthesis of [(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester (example 35, step f) the intermediate was prepared from [(3S,4R)-4-(4-Chloro-phenyl)-pyrrolidin-3-yl]-ethyl-carbamic acid 4-fluoro-phenyl ester and 1-(5-hydroxypyridin-2-yl)piperidine-4-carboxylic acid. Afterwards, acetyl chloride was added and stirring was continued for 30 min at room temperature. The mixture was directly subjected to preparative HPLC on reversed phase eluting with a gradient formed from acetonitrile, water and NEt3. The product containing fractions were evaporated to yield the title compound as off-white solid. MS m/e: 608.2 [M+H]+.

Experimental Procedure

The compounds were investigated in accordance with the tests given hereinafter

[$^3$H]SR142801 Competition Binding Assay hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 mM at 4° C., the pellets were resuspended in the 50 mM Tris-HCl, 4 mM MnCl$_2$, 1 µM phosphoramidon, 0.1% BSA binding buffer at pH 7.4 to a final assay concentration of 5 µg protein/well. For inhibition experiments, membranes were incubated with [$^3$H]SR142801 at a concentration equal to K$_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Canberra Packard S.A., Zürich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). IC$_{50}$ values were derived from the inhibition curve and the affinity constant (K$_i$) values were calculated using the Cheng-Prussoff equation $K_i=IC_{50}/(1+[L]/K_D)$ where [L] is the concentration of radioligand and K$_D$ is its dissociation constant at the receptor, derived from the saturation isotherm. All experiments were performed in duplicate and the mean±standard error (SEM) of the individual K$_i$ values was calculated.

The results of all specific compounds with a hNK-3 receptor affinity in µM were shown in the following table 1.

TABLE 1

| Example | Data K$_i$ [µM] |
|---|---|
| 1 | 0.001 |
| 2 | 0.046 |
| 3 | 0.276 |
| 4 | 0.01 |
| 5 | 0.002 |
| 6 | 0.062 |
| 7 | 0.089 |
| 8 | 0.055 |
| 9 | 0.138 |
| 10 | 0.065 |
| 11 | 0.036 |
| 12 | 0.023 |
| 13 | 0.008 |
| 14 | 0.003 |
| 15 | 0.008 |
| 16 | 0.002 |
| 17 | 0.002 |
| 18 | 0.002 |
| 19 | 0.088 |
| 20 | 0.003 |
| 21 | 0.002 |
| 22 | 0.025 |
| 23 | 0.021 |
| 24 | 0.062 |
| 25 | 0.112 |
| 26 | 0.046 |
| 27 | 0.047 |
| 28 | 0.05 |
| 29 | 0.012 |
| 30 | 0.035 |
| 31 | 0.057 |
| 32 | 0.052 |
| 33 | 0.048 |
| 34 | 0.116 |
| 35 | 0.004 |
| 36 | 0.01 |
| 37 | 0.008 |
| 38 | 0.007 |
| 39 | 0.004 |
| 40 | 0.0007 |
| 41 | 0.0006 |
| 42 | 0.002 |
| 43 | 0.0003 |
| 44 | 0.002 |
| 45 | 0.003 |
| 46 | 0.001 |
| 47 | 0.002 |
| 48 | 0.002 |
| 49 | 0.005 |
| 50 | 0.009 |
| 51 | 0.002 |
| 52 | 0.015 |
| 53 | 0.016 |
| 54 | 0.007 |
| 55 | 0.009 |
| 56 | 0.267 |
| 57 | 0.0007 |
| 58 | 0.005 |
| 59 | 0.0005 |
| 60 | 0.004 |
| 61 | 0.0008 |
| 62 | 0.006 |
| 63 | 0.0007 |
| 64 | 0.005 |
| 65 | 0.003 |
| 66 | 0.001 |
| 67 | 0.002 |
| 68 | 0.002 |
| 69 | 0.002 |
| 70 | 0.004 |
| 71 | 0.004 |
| 72 | 0.002 |
| 73 | 0.003 |
| 74 | 0.012 |
| 75 | 0.003 |
| 76 | 0.017 |
| 77 | 0.004 |
| 78 | 0.005 |
| 79 | 0.008 |
| 80 | 0.002 |
| 81 | 0.029 |
| 82 | 0.0082 |
| 83 | 0.0038 |
| 84 | 0.0298 |
| 85 | 0.0233 |
| 86 | 0.0707 |
| 87 | 0.0021 |
| 88 | 0.0056 |
| 89 | 0.0033 |
| 90 | 0.0024 |
| 91 | 0.0065 |
| 92 | 0.0066 |
| 93 | 0.0071 |
| 94 | 0.0078 |
| 95 | 0.0061 |
| 96 | 0.0034 |
| 97 | 0.0044 |
| 98 | 0.0047 |
| 99 | 0.0047 |
| 100 | 0.0036 |
| 101 | 0.0425 |
| 102 | 0.0082 |
| 103 | 0.0326 |
| 104 | 0.0176 |
| 105 | 0.0312 |
| 106 | 0.066 |

TABLE 1-continued

| Example | Data $K_i$ [μM] |
|---|---|
| 107 | 0.1312 |
| 108 | 0.0047 |
| 109 | 0.0017 |
| 110 | 0.0048 |
| 111 | 0.0074 |
| 112 | 0.0008 |
| 113 | 0.0005 |
| 114 | 0.0016 |
| 115 | 0.0009 |
| 116 | 0.0005 |
| 117 | 0.0033 |
| 118 | 0.0018 |
| 119 | 0.0037 |
| 120 | 0.0017 |
| 121 | 0.0169 |
| 122 | 0.0696 |
| 123 | 0.006 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Example A

Tablets of the following composition are manufactured in the usual manner:

| | mg/tablet |
|---|---|
| Active substance | 5 |
| Lactose | 45 |
| Corn starch | 15 |
| Micro crystalline cellulose | 34 |
| Magnesium stearate | 1 |
| Tablet weight | 100 |

Example B

Capsules of the following composition are manufactured:

| | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelantine capsules.

Example C

Suppositories of the following composition are manufactured:

| | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The invention claimed is:
1. A compound of formula I

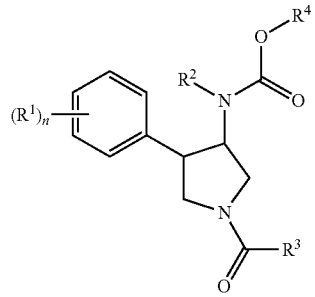

wherein
$R^1$ is hydrogen, halogen, cyano, lower alkyl or lower alkyl substituted by halogen;

n is 1, 2 or 3, wherein when n is 2 or 3, each $R^1$ is the same or different;
$R^2$ is $C_{2-7}$-alkyl or $C_{3-6}$-cycloalkyl;
$R^3$ is the group

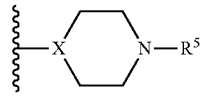

wherein
X is CH or N;
$R^5$ is hydrogen, —C(O)-lower alkyl, —C(O)O-lower alkyl, $S(O)_2$-lower alkyl, —C(O)CH$_2$O-lower alkyl, —C(O)—CH$_2$—CN, or is
—C(O)-cycloalkyl, cycloalkyl, or —CH$_2$-cycloalkyl,
wherein the cycloalkyl groups are optionally substituted by lower alkyl, —CH$_2$—O-lower alkyl, lower alkoxy, CF$_3$, halogen or cyano, or is
—C(O)-heterocycloalkyl, heterocycloalkyl, —C(O)-heteroaryl, heteroaryl, —C(O)-aryl, or aryl,
which heterocycloalkyl, heteroaryl or aryl groups are optionally substituted by halogen, lower alkyl, =O, lower alkoxy, lower alkyl substituted by halogen, lower alkyl substituted by hydroxy, —C(O)—CH$_2$—N(di-lower alkyl), C(O)NH-lower alkyl, C(O)NH$_2$, —O—C(O)-lower alkyl, C(O)-lower alkyl, $S(O)_2$-lower alkyl or cyano;
$R^4$ is aryl, which is optionally substituted by halogen, hydroxy, lower alkyl, lower alkyl substituted by halogen, $S(O)_2$-lower alkyl, cyano or by lower alkoxy;
or a pharmaceutically active salt thereof.

2. The compound of claim 1, wherein $R^4$ is aryl substituted by halogen.

3. The compound of claim 2, wherein aryl is phenyl.

4. The compound of claim 1, having formula Ia

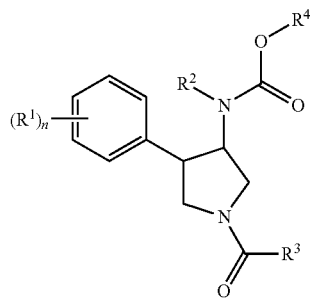

wherein
$R^1$ is halogen;
n is 1, 2 or 3, wherein when n is 2 or 3, each halogen is the same or different;
$R^2$ is $C_{2-7}$-alkyl or $C_{3-6}$-cycloalkyl;
$R^3$ is the group

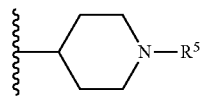

wherein
$R^5$ is hydrogen, —C(O)-lower alkyl, —C(O)O-lower alkyl, $S(O)_2$-lower alkyl, —C(O)—CH$_2$—CN, or is
—C(O)-cycloalkyl,
wherein the cycloalkyl groups are optionally substituted by lower alkyl, —CH$_2$—O-lower alkyl, lower alkoxy, CF$_3$, halogen or cyano, or is
—C(O)-heterocycloalkyl, —C(O)-heteroaryl, heteroaryl, or —C(O)-aryl,
which heterocycloalkyl, heteroaryl or aryl groups are optionally substituted by halogen, lower alkyl, =O, lower alkyl substituted by halogen, lower alkyl substituted by hydroxy, —C(O)—CH$_2$—N(di-lower alkyl), C(O)NH$_2$, —O—C(O)-lower alkyl, C(O)-lower alkyl, $S(O)_2$-lower alkyl or cyano;
$R^4$ is aryl, which is optionally substituted by halogen,
or a pharmaceutically active salt thereof.

5. The compound of claim 1, selected from the group consisting of
rac-{(3S,4R)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester;
rac-{(3S,4R)-4-(3,4-Dichloro-phenyl)-1-[1-(1-methyl-cyclopropanecarbonyl)-piperidine-4-carbonyl]-pyrrolidin-3-yl}-isopropyl-carbamic acid 4-fluoro-phenyl ester;
rac-{(3S,4R)-4-(3,4-Dichloro-phenyl)-1-[1-(1-methyl-cyclopropanecarbonyl)-piperidine-4-carbonyl]-pyrrolidin-3-yl}-isobutyl-carbamic acid 4-fluoro-phenyl ester;
rac-{(3S,4R)-4-(3,4-Dichloro-phenyl)-1-[1-(1-methyl-cyclopropanecarbonyl)-piperidine-4-carbonyl]-pyrrolidin-3-yl}-cyclopropyl-carbamic acid 4-fluoro-phenyl ester;
{(3S,4R)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester;
{(3R,4S)-4-(3,4-Dichloro-phenyl)-1-[1-(1-methyl-cyclopropanecarbonyl)-piperidine-4-carbonyl]-pyrrolidin-3-yl}-ethyl-carbamic acid 4-fluoro-phenyl ester;
{(3R,4S)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester;
[(3R,4S)-1-(5'-Acetyl-3,4,5,6-tetrahydro-2H-[1,2']bipyridinyl-4-carbonyl)-4-(4-chloro-phenyl)-pyrrolidin-3-yl]-ethyl-carbamic acid 4-fluoro-phenyl ester;
[(3R,4S)-4-(4-Chloro-phenyl)-1-(4'-cyano-3,4,5,6-tetrahydro-2H-[1,2']bipyridinyl-4-carbonyl)-pyrrolidin-3-yl]-ethyl-carbamic acid 4-fluoro-phenyl ester;
[(3R,4S)-4-(4-Chloro-phenyl)-1-(5'-methanesulfonyl-3,4,5,6-tetrahydro-2H-[1,2']bipyridinyl-4-carbonyl)-pyrrolidin-3-yl]-ethyl-carbamic acid 4-fluoro-phenyl ester;
{(3R,4S)-4-(4-Chloro-phenyl)-1-[1-(5-cyano-pyrazin-2-yl)-piperidine-4-carbonyl]-pyrrolidin-3-yl}-ethyl-carbamic acid 4-fluoro-phenyl ester; and
{(3R,4S)-4-(4-Chloro-phenyl)-1-[1-(6-cyano-pyridazin-3-yl)-piperidine-4-carbonyl]-pyrrolidin-3-yl}-ethyl-carbamic acid 4-fluoro-phenyl ester.

6. The compound of claim 1, selected from the group consisting of
{(3S,4R)-4-(4-Chloro-phenyl)-1-[1-(5-cyano-pyrimidin-2-yl)-piperidine-4-carbonyl]-pyrrolidin-3-yl}-ethyl-carbamic acid 4-fluoro-phenyl ester;
[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-ethyl-carbamic acid 4-fluoro-phenyl ester;
[(3S,4R)-4-(4-Chloro-phenyl)-1-(4'-cyano-3,4,5,6-tetrahydro-2H-[1,2']bipyridinyl-4-carbonyl)-pyrrolidin-3-yl]-ethyl-carbamic acid 4-fluoro-phenyl ester;
[(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-ethyl-carbamic acid 4-fluoro-phenyl ester;

{(3S,4R)-4-(4-Chloro-phenyl)-1-[1-(5-cyano-pyrazin-2-yl)-piperidine-4-carbonyl]-pyrrolidin-3-yl}-ethyl-carbamic acid 4-fluoro-phenyl ester;

{(3S,4R)-4-(4-Chloro-phenyl)-1-[1-(6-cyano-pyridazin-3-yl)-piperidine-4-carbonyl]-pyrrolidin-3-yl}-ethyl-carbamic acid 4-fluoro-phenyl ester;

[(3R,4S)-4-(4-Chloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-ethyl-carbamic acid 4-fluoro-phenyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-isopropyl-carbamic acid 4-fluoro-phenyl ester; and

[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-isopropyl-carbamic acid 4-fluoro-phenyl ester.

7. The compound of claim 1, selected from the group consisting of

[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-isopropyl-carbamic acid 4-fluoro-phenyl ester;

{(3S,4R)-4-(4-Chloro-phenyl)-1-[1-(6-cyano-pyridazin-3-yl)-piperidine-4-carbonyl]-pyrrolidin-3-yl}-isopropyl-carbamic acid 4-fluoro-phenyl ester;

{(3S,4R)-4-(4-Chloro-phenyl)-1-[1-(5-cyano-pyrazin-2-yl)-piperidine-4-carbonyl]-pyrrolidin-3-yl}-isopropyl-carbamic acid 4-fluoro-phenyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-isopropyl-carbamic acid 4-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-cyclopropyl-carbamic acid 4-fluoro-phenyl ester;

[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-cyclopropyl-carbamic acid 4-fluoro-phenyl ester;

[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-cyclopropyl-carbamic acid 4-fluoro-phenyl ester;

{(3S,4R)-4-(4-Chloro-phenyl)-1-[1-(6-cyano-pyridazin-3-yl)-piperidine-4-carbonyl]-pyrrolidin-3-yl}-cyclopropyl-carbamic acid 4-fluoro-phenyl ester;

{(3S,4R)-4-(4-Chloro-phenyl)-1-[1-(5-cyano-pyrazin-2-yl)-piperidine-4-carbonyl]-pyrrolidin-3-yl}-cyclopropyl-carbamic acid 4-fluoro-phenyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-cyclopropyl-carbamic acid 4-fluoro-phenyl ester;

[(3S,4R)-1-(5'-Cyano-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester; and

[(3S,4R)-1-(5'-Chloro-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester.

8. The compound of claim 1, selected from the group consisting of

Ethyl-[(3S,4R)-4-(4-fluoro-phenyl)-1-(5'-methanesulfonyl-3,4,5,6-tetrahydro-2H-[1,2]bipyridinyl-4-carbonyl)-pyrrolidin-3-yl]-carbamic acid 4-fluoro-phenyl ester;

[(3S,4R)-1-(5'-Acetyl-3,4,5,6-tetrahydro-2H-[1,2']bipyridinyl-4-carbonyl)-4-(4-fluoro-phenyl)-pyrrolidin-3-yl]-ethyl-carbamic acid 4-fluoro-phenyl ester;

4-{(3R,4S)-3-(4-Chloro-3-fluoro-phenyl)-4-[ethyl-(4-fluoro-phenoxycarbonyl)-amino]-pyrrolidine-1-carbonyl}-piperidine-1-carboxylic acid tert-butyl ester;

[(3S,4R)-4-(4-Chloro-3-fluoro-phenyl)-1-(5'-cyano-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-3-fluoro-phenyl)-1-(5'-chloro-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-3-fluoro-phenyl)-1-(5'-trifluoromethyl-3,4,5,6-tetrahydro-2H-[1,2']bipyridinyl-4-carbonyl)-pyrrolidin-3-yl]ethyl-carbamic acid 4-fluoro-phenyl ester;

[(3S,4R)-4-(4-Chloro-3-fluoro-phenyl)-1-(6'-cyano-3,4,5,6-tetrahydro-2H-[1,3]bipyridinyl-4-carbonyl)-pyrrolidin-3-yl]-ethyl-carbamic acid 4-fluoro-phenyl ester;

{(3S,4R)-4-(4-Chloro-3-fluoro-phenyl)-1-[1-(1-methyl-cyclopropanecarbonyl)-piperidine-4-carbonyl]-pyrrolidin-3-yl}-ethyl-carbamic acid 4-fluoro-phenyl ester;

[(3S,4R)-4-(4-Chloro-3-fluoro-phenyl)-1-(4'-cyano-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-3-fluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-3-fluoro-phenyl)-1-(5'-methyl-3,4,5,6-tetrahydro-2H-[1,2']bipyridinyl-4-carbonyl)-pyrrolidin-3-yl]-ethyl-carbamic acid 4-fluoro-phenyl ester; and

[(3S,4R)-1-(5'-Cyano-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester.

9. The compound of claim 1, selected from the group consisting of

[(3S,4R)-1-(5'-Chloro-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester;

[(3S,4R)-4-(3,4-Difluoro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-1-(6'-Cyano-3,4,5,6-tetrahydro-2H[1,3']bipyridinyl-4-carbonyl)-4-(3,4-difluoro-phenyl)-pyrrolidin-3-yl]-ethyl-carbamic acid 4-fluoro-phenyl ester;

{(3S,4R)-4-(3,4-Difluoro-phenyl)-1-[1-(1-methyl-cyclopropanecarbonyl)-piperidine-4-carbonyl]-pyrrolidin-3-yl}-ethyl-carbamic acid 4-fluoro-phenyl ester;

[(3S,4R)-1-(4'-Cyano-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester;

[(3S,4R)-4-(3,4-Difluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(3,4-Difluoro-phenyl)-1-(5'-methyl-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(4-Chloro-3-fluoro-phenyl)-1-(piperidine-4-carbonyl)-pyrrolidin-3-yl]-ethyl-carbamic acid 4-fluoro-phenyl ester;

{(3S,4R)-4-(4-Chloro-3-fluoro-phenyl)-1-[1-(6-cyano-pyridazin-3-yl)-piperidine-4-carbonyl]-pyrrolidin-3-yl}-ethyl-carbamic acid 4-fluoro-phenyl ester;

[(3S,4R)-1-[1-(6-Cyano-pyridazin-3-yl)-piperidine-4-carbonyl]-4-(3,4-difluoro-phenyl)-pyrrolidin-3-yl]-ethyl-carbamic acid 4-fluoro-phenyl ester;

[(3S,4R)-1-(5'-Acetyl-3,4,5,6-tetrahydro-2H-[1,2']bipyridinyl-4-carbonyl)-4-(4-chloro-3-fluoro-phenyl)-pyrrolidin-3-yl]-ethyl-carbamic acid 4-fluoro-phenyl ester; and

[(3S,4R)-1-(5'-Acetyl-3,4,5,6-tetrahydro-2H-[1,2']bipyridinyl-4-carbonyl)-4-(3,4-difluoro-phenyl)-pyrrolidin-3-yl]-ethyl-carbamic acid 4-fluoro-phenyl ester.

10. The compound of claim 1, selected from the group consisting of

{(3S,4R)-4-(4-Chloro-3-fluoro-phenyl)-1-[1-(5-cyano-pyrazin-2-yl)-piperidine-4-carbonyl]-pyrrolidin-3-yl}-ethyl-carbamic acid 4-fluoro-phenyl ester;

[(3S,4R)-1-[1-(5-Cyano-pyrazin-2-yl)-piperidine-4-carbonyl]-4-(3,4-difluoro-phenyl)-pyrrolidin-3-yl]-ethyl-carbamic acid 4-fluoro-phenyl ester;

[(3S,4R)-4-(4-Chloro-3-fluoro-phenyl)-1-(5'-methanesulfonyl-3,4,5,6-tetrahydro-2H-[1,2]bipyridinyl-4-carbonyl)-pyrrolidin-3-yl]-ethyl-carbamic acid 4-fluoro-phenyl ester;

[(3S,4R)-4-(3,4-Difluoro-phenyl)-1-(5'-methanesulfonyl-3,4,5,6-tetrahydro-2H-[1,2']bipyridinyl-4-carbonyl)-pyrrolidin-3-yl]-ethyl-carbamic acid 4-fluoro-phenyl ester;

{(3S,4R)-4-(4-Chloro-3-fluoro-phenyl)-1-[1-(3-methyl-oxetane-3-carbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(3,3-difluoro-cyclobutanecarbonyl)-piperidine-4-carbonyl]-pyrrolidin-3-yl}-ethyl-carbamic acid 4-fluoro-phenyl ester;

[(3S,4R)-4-(4-Chloro-3-fluoro-phenyl)-1-(1-cyclobutanecarbonyl-piperidine-4-carbonyl)-pyrrolidin-3-yl]-ethyl-carbamic acid 4-fluoro-phenyl ester;

{(3S,4R)-4-(4-Chloro-3-fluoro-phenyl)-1-[1-(1-trifluoromethyl-cyclobutanecarbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(3-fluoro-cyclobutanecarbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(2,2-difluoro-cyclopropanecarbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(1-trifluoromethyl-cyclopropanecarbonyl)-piperidine-4-carbonyl]-pyrrolidin-3-yl}-ethyl-carbamic acid 4-fluoro-phenyl ester; and {(3S,4R)-4-(4-Chloro-3-fluoro-phenyl)-1-[1-(1-cyano-cyclopropanecarbonyl)-piperidine-4-carbonyl]-pyrrolidin-3-yl}-ethyl-carbamic acid 4-fluoro-phenyl ester.

11. The compound of claim 1, selected from the group consisting of

{(3S,4R)-4-(4-Chloro-3-fluoro-phenyl)-1-[1-(2,2-dimethyl-tetrahydro-pyran-4-carbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(5-trifluoromethyl-pyridine-2-carbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(5-fluoro-pyridine-2-carbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(4-cyano-benzoyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(4-fluoro-benzoyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(5-trifluoromethyl-pyrazine-2-carbonyl)-piperidine-4-carbonyl]-pyrrolidin-3-yl}-ethyl-carbamic acid 4-fluoro-phenyl ester;

{(3S,4R)-4-(4-Chloro-3-fluoro-phenyl)-1-[1-(6-cyano-pyridine-3-carbonyl)-piperidine-4-carbonyl]-pyrrolidin-3-yl}-ethyl-carbamic acid 4-fluoro-phenyl ester;

[(3S,4R)-1-(1-Acetyl-piperidine-4-carbonyl)-4-(4-chloro-3-fluoro-phenyl)-pyrrolidin-3-yl]-ethyl-carbamic acid 4-fluoro-phenyl ester;

[(3S,4R)-4-(4-Chloro-3-fluoro-phenyl)-1-(1-methanesulfonyl-piperidine-4-carbonyl)-pyrrolidin-3-yl]-ethyl-carbamic acid 4-fluoro-phenyl ester;

[(3S,4R)-1-(1-Acetyl-piperidine-4-carbonyl)-4-(4-chloro-phenyl)-pyrrolidin-3-yl]-ethyl-carbamic acid 4-fluoro-phenyl ester;

{(3S,4R)-4-(4-Chloro-3-fluoro-phenyl)-1-[5'-(1-hydroxy-1-methyl-ethyl)-3,4,5,6-tetrahydro-2H-[1,2]bipyridinyl-4-carbonyl]-pyrrolidin-3-yl}-ethyl-carbamic acid 4-fluoro-phenyl ester; and {(3S,4R)-4-(4-Chloro-phenyl)-1-[1-(3-methyl-oxetane-3-carbonyl)-piperidine-4-carbonyl]-pyrrolidin-3-yl}-ethyl-carbamic acid 2-fluoro-phenyl ester.

12. The compound of claim 1, selected from the group consisting of

{(3S,4R)-4-(4-Chloro-phenyl)-1-[1-(1-cyano-cyclopropanecarbonyl)-piperidine-4-carbonyl]-pyrrolidin-3-yl}-ethyl-carbamic acid 2-fluoro-phenyl ester;

{(3S,4R)-4-(4-Chloro-phenyl)-1-[1-(5-trifluoromethyl-pyridine-2-carbonyl)-piperidine-4-carbonyl]-pyrrolidin-3-yl}-ethyl-carbamic acid 2-fluoro-phenyl ester;

[(3S,4R)-4-(4-Chloro-phenyl)-1-(1-cyclobutanecarbonyl-piperidine-4-carbonyl)-pyrrolidin-3-yl]-ethyl-carbamic acid 4-fluoro-phenyl ester;

{(3S,4R)-4-(4-Chloro-phenyl)-1-[1-(3-methyl-oxetane-3-carbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(3-fluoro-cyclobutanecarbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(3,3-difluoro-cyclobutanecarbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(3-methoxy-cyclobutanecarbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(1-trifluoromethyl-cyclobutanecarbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(2-cyano-acetyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(1-cyano-cyclopropanecarbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(1-trifluoromethyl-cyclopropanecarbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(2,2-difluoro-cyclopropanecarbonyl)-piperidine-4-carbonyl]-pyrrolidin-3-yl}-ethyl-carbamic acid 4-fluoro-phenyl ester; and {(3S,4R)-4-(4-Chloro-phenyl)-1-[1-(tetrahydro-pyran-4-carbonyl)-piperidine-4-carbonyl]-pyrrolidin-3-yl}-ethyl-carbamic acid 4-fluoro-phenyl ester.

13. The compound of claim 1, selected from the group consisting of

{(3S,4R)-4-(4-Chloro-phenyl)-1-[1-(2,2-dimethyl-tetrahydro-pyran-4-carbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(1-methoxymethyl-cyclopropanecarbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(2,2-dimethyl-cyclopropanecarbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(5-trifluoromethyl-pyridine-2-carbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(5-fluoro-pyridine-2-carbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(6-oxo-piperidine-3-carbonyl)-piperidine-4-carbonyl]-pyrrolidin-3-yl}-ethyl-carbamic acid 4-fluoro-phenyl ester;

{(3S,4R)-4-(4-Chloro-phenyl)-1-[1-(1-isopropyl-6-oxo-piperidine-3-carbonyl)-piperidine-4-carbonyl]-pyrrolidin-3-yl}-ethyl-carbamic acid 4-fluoro-phenyl ester;

[(3S,4R)-4-(4-Chloro-3-fluoro-phenyl)-1-(1-isopropyl-6-oxo-piperidine-3-carbonyl)-pyrrolidin-3-yl]-ethyl-carbamic acid 4-fluoro-phenyl ester;

{(3S,4R)-4-(3,4-Difluoro-phenyl)-1-[1-((S)-4-oxo-azetidine-2-carbonyl)-piperidine-4-carbonyl]-pyrrolidin-3-yl}-ethyl-carbamic acid 4-fluoro-phenyl ester;

{(3S,4R)-4-(3,4-Difluoro-phenyl)-1-[1-(6-oxo-piperidine-3-carbonyl)-piperidine-4-carbonyl]-pyrrolidin-3-yl}-ethyl-carbamic acid 4-fluoro-phenyl ester;

{(3S,4R)-4-(4-Chloro-phenyl)-1-[5'-(1-hydroxy-ethyl)-3,4,5,6-tetrahydro-2H-[1,2']bipyridinyl-4-carbonyl]-pyrrolidin-3-yl}-ethyl-carbamic acid 4-fluoro-phenyl ester;

[(3S,4R)-1-(5'-Carbamoyl-3,4,5,6-tetrahydro-2H-[1,2']bipyridinyl-4-carbonyl)-4-(4-chloro-3-fluoro-phenyl)-pyrrolidin-3-yl]-ethyl-carbamic acid 4-fluoro-phenyl ester; and

[(3S,4R)-4-(4-Chloro-phenyl)-1-(5'-chloro-3,4,5,6-tetrahydro-2H-[1,2']bipyridinyl-4-carbonyl)-pyrrolidin-3-yl]-ethyl-carbamic acid 4-fluoro-phenyl ester.

14. The compound of claim 1, selected from the group consisting of

[(3S,4R)-1-(5'-Carbamoyl-3,4,5,6-tetrahydro-2H-[1,2']bipyridinyl-4-carbonyl)-4-(4-chloro-phenyl)-pyrrolidin-3-yl]-ethyl-carbamic acid 4-fluoro-phenyl ester;

[(3S,4R)-4-(3,4-Dichloro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-1-(5'-Chloro-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester;

[(3S,4R)-4-(3,4-Dichloro-phenyl)-1-(5'-trifluoromethyl-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-1-(5'-Carbamoyl-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester;

[(3S,4R)-1-(5'-Acetyl-3,4,5,6-tetrahydro-2H-[1,2']bipyridinyl-4-carbonyl)-4-(3,4-dichloro-phenyl)-pyrrolidin-3-yl]-ethyl-carbamic acid 4-fluoro-phenyl ester;

[(3S,4R)-4-(3-Chloro-4-fluoro-phenyl)-1-(5'-fluoro-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(3-Chloro-4-fluoro-phenyl)-1-(5'-chloro-3,4,5,6-tetrahydro-2H-[1,2']bipyridinyl-4-carbonyl)-pyrrolidin-3-yl]-ethyl-carbamic acid 4-fluoro-phenyl ester;

[(3S,4R)-4-(3-Chloro-4-fluoro-phenyl)-1-(5'-trifluoromethyl-3,4,5,6-tetrahydro-2H-[1,2]bipyridinyl-4-carbonyl)-pyrrolidin-3-yl]-ethyl-carbamic acid 4-fluoro-phenyl ester;

[(3S,4R)-1-(5'-Acetyl-3,4,5,6-tetrahydro-2H-[1,2']bipyridinyl-4-carbonyl)-4-(3-chloro-4-fluoro-phenyl)-pyrrolidin-3-yl]-ethyl-carbamic acid 4-fluoro-phenyl ester;

[(3S,4R)-4-(4-Chloro-phenyl)-1-[1-((S)-4-oxo-azetidine-2-carbonyl)-piperidine-4-carbonyl]-pyrrolidin-3-yl]-ethyl-carbamic acid 4-fluoro-phenyl ester;

[(3S,4R)-1-[5'-(2-Diethylamino-acetyl)-3,4,5,6-tetrahydro-2H-[1,2']bipyridinyl-4-carbonyl]-4-(4-fluoro-phenyl)-pyrrolidin-3-yl]-ethyl-carbamic acid 4-fluoro-phenyl ester, and acetic acid 4-{(3R,4S)-3-(4-chloro-phenyl)-4-[ethyl-(4-fluoro-phenoxycarbonyl)-amino]-pyrrolidine-1-carbonyl}-3,4,5,6-tetrahydro-2H-[1,2']bipyridinyl-5'-yl ester.

15. A pharmaceutical composition comprising a therapeutically effective amount of a compound of formula I

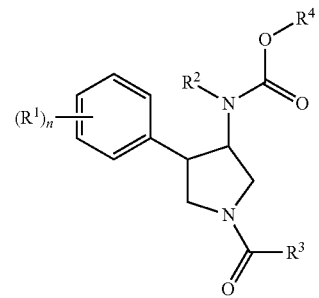

wherein

R¹ is hydrogen, halogen, cyano, lower alkyl or lower alkyl substituted by halogen;

n is 1, 2 or 3, wherein when n is 2 or 3, each R¹ is the same or different;

R² is $C_{2-7}$-alkyl or $C_{3-6}$-cycloalkyl;

R³ is the group

wherein

X is CH or N;

R⁵ is hydrogen, —C(O)-lower alkyl, —C(O)O-lower alkyl, S(O)₂-lower alkyl, —C(O)CH₂O-lower alkyl, —C(O)—CH₂—CN, or is —C(O)-cycloalkyl, cycloalkyl, or —CH₂-cycloalkyl, wherein the cycloalkyl groups are optionally substituted by lower alkyl, —CH₂—O-lower alkyl, lower alkoxy, CF₃, halogen or cyano, or is —C(O)-heterocycloalkyl, heterocycloalkyl, —C(O)-heteroaryl, heteroaryl, —C(O)-aryl, or aryl,
which heterocycloalkyl, heteroaryl or aryl groups are optionally substituted by halogen, lower alkyl, =O, lower alkoxy, lower alkyl substituted by halogen, lower alkyl substituted by hydroxy, —C(O)—$CH_2$—N(di-lower alkyl), C(O)NH-lower alkyl, C(O)$NH_2$, —O—C(O)-lower alkyl, C(O)-lower alkyl, S(O)$_2$-lower alkyl or cyano;

$R^4$ is aryl, which is optionally substituted by halogen, hydroxy, lower alkyl, lower alkyl substituted by halogen, S(O)$_2$-lower alkyl, cyano or by lower alkoxy;

or a pharmaceutically active salt thereof
and a pharmaceutically acceptable carrier.

* * * * *